(12) United States Patent
Ziv et al.

(10) Patent No.: US 10,964,075 B2
(45) Date of Patent: Mar. 30, 2021

(54) GATING WITH ANATOMICALLY VARYING DURATIONS

(71) Applicant: Spectrum Dynamics LLC, Orangeburg, NY (US)

(72) Inventors: Omer Ziv, Rechovot (IL); Ran Ravhon, Kiryat-Bialik (IL); Eli Dichterman, Haifa (IL); Leonid Gluhovsky, Haifa (IL); Shlomo Ben-Haim, Geneva (CH); Benny Rousso, Rishon-LeZion (IL)

(73) Assignee: Spectrum Dynamics LLC, Orangeburg, NY (US)

(*) Notice: Subject to any disclaimer, the term of this patent is extended or adjusted under 35 U.S.C. 154(b) by 25 days.

(21) Appl. No.: 15/294,737

(22) Filed: Oct. 16, 2016

(65) Prior Publication Data

US 2017/0039738 A1    Feb. 9, 2017

Related U.S. Application Data

(63) Continuation of application No. 12/087,150, filed as application No. PCT/IL2006/001511 on Dec. 28, (Continued)

(30) Foreign Application Priority Data

Oct. 10, 2005   (IL) .......................................... 171346
Nov. 27, 2005   (IL) .......................................... 172349

(51) Int. Cl.
*G06T 11/00* (2006.01)
*A61B 6/03* (2006.01)
(Continued)

(52) U.S. Cl.
CPC ............ *G06T 11/006* (2013.01); *A61B 5/055* (2013.01); *A61B 5/7289* (2013.01); *A61B 6/032* (2013.01);
(Continued)

(58) Field of Classification Search
None
See application file for complete search history.

(56) References Cited

U.S. PATENT DOCUMENTS

| 630,611 A | 8/1899 | Knapp et al. |
| 2,776,377 A | 1/1957 | Anger |

(Continued)

FOREIGN PATENT DOCUMENTS

| DE | 1516429 | 12/1969 |
| DE | 19814199 | 10/1999 |

(Continued)

OTHER PUBLICATIONS

Zaidi, H., et al. "Fuzzy clustering-based segmented attenuation correction in whole-body PET imaging." Physics in Medicine & Biology 47.7 (2002): 1143.*

(Continued)

*Primary Examiner* — Zhengxi Liu

(57) ABSTRACT

A method for reconstructing a radioactive emission image of an overall volume having first and second volumetric regions, each volumetric region having respectively independent dynamic characteristics. The method comprises the following steps: a) obtaining radioactive emissions from the overall volume, including the volumetric regions, b) reconstructing an initial radioactive emission image of the volumetric region according to the radioactive emissions, c) segmenting the initial radioactive emission image to delineate the first and second volumetric regions, and d) separately reconstructing the first and the second volumetric (Continued)

regions according to the respectively independent dynamic characteristics.

29 Claims, 32 Drawing Sheets
(19 of 32 Drawing Sheet(s) Filed in Color)

Related U.S. Application Data 2006, now Pat. No. 9,470,801, and a continuation of application No. 11/607,075, filed on Dec. 1, 2006, now Pat. No. 8,094,894, and a continuation of application No. PCT/IL2006/001291, filed on Nov. 9, 2006, and a continuation of application No. PCT/IL2006/000834, filed on Jul. 19, 2006, and a continuation of application No. PCT/IL2006/000840, filed on Jul. 19, 2006, and a continuation of application No. PCT/IL2006/000562, filed on May 11, 2006, and a continuation of application No. PCT/IL2006/000059, filed on Jan. 15, 2006, and a continuation of application No. 12/084,559, filed as application No. PCT/IL2006/001291 on Nov. 9, 2006, now Pat. No. 7,705,316, which is a continuation-in-part of application No. PCT/IL2006/000840, filed on Jul. 19, 2006, and a continuation-in-part of application No. PCT/IL2006/000834, filed on Jul. 19, 2006, and a continuation-in-part of application No. PCT/IL2006/000562, filed on May 11, 2006, and a continuation-in-part of application No. PCT/IL2006/000059, filed on Jan. 15, 2006, and a continuation-in-part of application No. PCT/IL2005/001215, filed on Nov. 16, 2005, and a continuation-in-part of application No. PCT/IL2005/001173, filed on Nov. 9, 2005, which is a continuation-in-part of application No. PCT/IL2005/000575, filed on Jun. 1, 2005, and a continuation-in-part of application No. PCT/IL2005/000572, filed on Jun. 1, 2005, and a continuation-in-part of application No. PCT/IL2005/000048, filed on Jan. 13, 2005, said application No. 12/084,559 is a continuation-in-part of application No. 11/034,007, filed on Jan. 13, 2005, now Pat. No. 7,176,466.

(60) Provisional application No. 60/816,970, filed on Jun. 28, 2006, provisional application No. 60/800,846, filed on May 17, 2006, provisional application No. 60/800,845, filed on May 17, 2006, provisional application No. 60/799,688, filed on May 11, 2006, provisional application No. 60/763,458, filed on Jan. 31, 2006, provisional application No. 60/754,199, filed on Dec. 28, 2005, provisional application No. 60/750,597, filed on Dec. 15, 2005, provisional application No. 60/750,334, filed on Dec. 15, 2005, provisional application No. 60/750,287, filed on Dec. 13, 2005, provisional application No. 60/741,440, filed on Dec. 2, 2005, provisional application No. 60/720,652, filed on Sep. 27, 2005, provisional application No. 60/720,541, filed on Sep. 27, 2005, provisional application No. 60/720,034, filed on Sep. 26, 2005, provisional application No. 60/702,979, filed on Jul. 28, 2005, provisional application No. 60/700,753, filed on Jul. 20, 2005, provisional application No. 60/700,752, filed on Jul. 20, 2005, provisional application No. 60/700,318, filed on Jul. 19, 2005, provisional application No. 60/700,317, filed on Jul. 19, 2005, provisional application No. 60/700,299, filed on Jul. 19, 2005, provisional application No. 60/691,780, filed on Jun. 20, 2005, provisional application No. 60/675,892, filed on Apr. 29, 2005, provisional application No. 60/648,690, filed on Feb. 2, 2005, provisional application No. 60/648,385, filed on Feb. 1, 2005, provisional application No. 60/640,215, filed on Jan. 3, 2005, provisional application No. 60/636,088, filed on Dec. 16, 2004, provisional application No. 60/635,630, filed on Dec. 14, 2004, provisional application No. 60/632,515, filed on Dec. 3, 2004, provisional application No. 60/632,236, filed on Dec. 2, 2004, provisional application No. 60/630,561, filed on Nov. 26, 2004, provisional application No. 60/628,105, filed on Nov. 17, 2004, provisional application No. 60/625,971, filed on Nov. 9, 2004, provisional application No. 60/575,369, filed on Jun. 1, 2004, provisional application No. 60/535,830, filed on Jan. 13, 2004.

(51) Int. Cl.
*G01T 1/161* (2006.01)
*G01T 1/24* (2006.01)
*G06T 7/62* (2017.01)
*A61B 5/055* (2006.01)
*A61B 5/00* (2006.01)
*A61B 6/00* (2006.01)
*A61B 8/13* (2006.01)
*A61B 8/08* (2006.01)
*G01T 1/164* (2006.01)
*G06T 7/00* (2017.01)

(52) U.S. Cl.
CPC .............. *A61B 6/037* (2013.01); *A61B 6/503* (2013.01); *A61B 6/5288* (2013.01); *A61B 8/13* (2013.01); *A61B 8/5284* (2013.01); *G01T 1/161* (2013.01); *G01T 1/1644* (2013.01); *G01T 1/243* (2013.01); *G01T 1/247* (2013.01); *G01T 1/249* (2013.01); *G06T 7/0012* (2013.01); *G06T 7/62* (2017.01); *G06T 2207/10088* (2013.01); *G06T 2207/10108* (2013.01); *G06T 2207/10116* (2013.01); *G06T 2207/10132* (2013.01); *G06T 2207/10136* (2013.01); *G06T 2207/30048* (2013.01)

(56) References Cited

U.S. PATENT DOCUMENTS

| | | |
|---|---|---|
| 3,340,866 A | 9/1967 | Noeller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluznikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |

(56) References Cited

U.S. PATENT DOCUMENTS

| | | |
|---|---|---|
| 4,364,377 A | 12/1982 | Smith |
| 4,383,327 A | 5/1983 | Kruger |
| 4,476,381 A | 10/1984 | Rubin |
| 4,492,119 A | 1/1985 | Dulapa et al. |
| 4,503,331 A | 5/1985 | Kovacs, Jr. et al. |
| 4,521,688 A | 6/1985 | Yin |
| 4,529,882 A | 7/1985 | Lee |
| H12 H | 1/1986 | Bennett et al. |
| 4,580,054 A | 4/1986 | Shimoni |
| 4,584,478 A | 4/1986 | Genna et al. |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledly |
| 4,938,230 A | 7/1990 | Machek et al. |
| 4,951,653 A | 8/1990 | Fly et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,877 A | 12/1991 | Mohiuddin et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,142,557 A | 8/1992 | Toker et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,338,936 A | 8/1994 | Gullberg et al. |
| 5,349,190 A | 9/1994 | Hines et al. |
| 5,350,355 A | 9/1994 | Sklar |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,396,531 A | 3/1995 | Hartley |
| 5,399,868 A | 3/1995 | Jones et al. |
| 5,404,293 A | 4/1995 | Weng et al. |
| 5,415,181 A | 5/1995 | Hofgrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misik et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,524,622 A | 6/1996 | Wilson |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,630,034 A | 5/1997 | Oikawa et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,250 A | 11/1997 | Curley et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |

(56) References Cited

U.S. PATENT DOCUMENTS

| | | |
|---|---|---|
| 5,716,595 A | 2/1998 | Goldenberg |
| 5,717,212 A | 2/1998 | Fulton et al. |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,799,111 A | 8/1998 | Guissin |
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,008 A | 9/1998 | Dekel et al. |
| 5,810,742 A | 9/1998 | Pearlman |
| 5,811,814 A | 9/1998 | Leone et al. |
| 5,813,985 A | 9/1998 | Carroll |
| 5,818,050 A | 10/1998 | Dilmanian et al. |
| 5,821,541 A | 10/1998 | Tuemer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 6/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,324,418 B1 | 1/2001 | Crowley et al. |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Turner |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |

(56) References Cited

U.S. PATENT DOCUMENTS

| | | |
|---|---|---|
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,257 B1 | 5/2002 | Gagnon et al. |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Turner |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,592,520 B1 | 3/2003 | Peszynski et al. |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,574,304 B1 | 6/2003 | Hsieh et al. |
| 6,575,930 B1 | 6/2003 | Trombley, III et al. |
| 6,576,918 B1 | 6/2003 | Fu et al. |
| 6,583,420 B1 | 6/2003 | Nelson et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,591,127 B1 | 7/2003 | McKinnon |
| 6,589,158 B2 | 8/2003 | Winkler |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engleson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,809,321 B2 | 10/2004 | Rempel |
| 6,813,868 B2 | 11/2004 | Baldwin et al. |

(56) References Cited

U.S. PATENT DOCUMENTS

| | | |
|---|---|---|
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Turner |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,009,183 B2 | 3/2006 | Wainer et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,102,138 B2 | 3/2006 | Belvis et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,145,986 B2 | 12/2006 | Wear et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,291,841 B2 | 11/2007 | Nelson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charon et al. |
| 7,470,896 B2 | 12/2008 | Pawlak et al. |
| 7,490,085 B2 | 2/2009 | Walker et al. |
| 7,495,225 B2 | 2/2009 | Hefetz et al. |
| 7,502,499 B2 | 3/2009 | Grady |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,671,331 B2 | 3/2010 | Hefez |
| 7,671,340 B2 | 3/2010 | Uribe et al. |
| 7,672,491 B2 | 3/2010 | Krishnan et al. |
| 7,680,240 B2 | 3/2010 | Manjeshwar et al. |
| 7,705,316 B2 | 4/2010 | Rousso et al. |
| 7,734,331 B2 | 6/2010 | Dhawale et al. |
| 7,826,889 B2 | 11/2010 | David et al. |
| 7,831,024 B2 | 11/2010 | Metzler et al. |
| 7,835,927 B2 | 11/2010 | Schlotterbeck et al. |
| 7,872,235 B2 | 1/2011 | Rousso et al. |
| 7,894,650 B2 | 2/2011 | Weng et al. |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,158,951 B2 | 4/2012 | Bal et al. |
| 8,163,661 B2 | 4/2012 | Akiyoshi et al. |
| 8,204,500 B2 | 6/2012 | Weintraub et al. |
| 8,338,788 B2 | 12/2012 | Zilberstein et al. |
| 8,440,168 B2 | 5/2013 | Yang et al. |
| 8,489,176 B1 | 7/2013 | Ben-David et al. |
| 8,565,860 B2 | 10/2013 | Kimchy et al. |
| 8,620,046 B2 | 12/2013 | Nagler et al. |
| 8,909,325 B2 | 12/2014 | Kimchy et al. |
| 2001/0016029 A1 | 8/2001 | Turner |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 | 11/2002 | Kaushikkar et al. |
| 2002/0168317 A1 | 11/2002 | Daighighian et al. |
| 2002/0172405 A1 | 11/2002 | Schultz |
| 2002/0179843 A1 | 12/2002 | Tanaka et al. |
| 2002/0183645 A1 | 12/2002 | Nachaliel |
| 2002/0188197 A1 | 12/2002 | Bishop et al. |
| 2002/0191734 A1 | 12/2002 | Kojima et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Tumer |
| 2003/0013950 A1* | 1/2003 | Rollo .................. G01T 1/1647 600/407 |
| 2003/0013966 A1 | 1/2003 | Barnes et al. |
| 2003/0139661 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0136912 A1 | 6/2003 | Juni |
| 2003/0135388 A1 | 7/2003 | Martucci et al. |
| 2003/0144322 A1 | 7/2003 | Kozikowski et al. |
| 2003/0147887 A1 | 8/2003 | Wang et al. |
| 2003/0158481 A1 | 8/2003 | Stotzka et al. |
| 2003/0174804 A1 | 9/2003 | Bulkes et al. |
| 2003/0178559 A1 | 9/2003 | Hamill et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 | 11/2003 | Tanaka |
| 2003/0215124 A1 | 11/2003 | Li |
| 2003/0216631 A1 | 11/2003 | Bloch et al. |
| 2003/0219149 A1 | 11/2003 | Vailaya et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0021065 A1 | 2/2004 | Weber |
| 2004/0044282 A1 | 3/2004 | Mixon et al. |

(56) References Cited

U.S. PATENT DOCUMENTS

| | | |
|---|---|---|
| 2004/0051368 A1 | 3/2004 | Caputo et al. |
| 2004/0054248 A1 | 3/2004 | Kimchy et al. |
| 2004/0054278 A1 | 3/2004 | Kimchy et al. |
| 2004/0065838 A1 | 4/2004 | Tumer |
| 2004/0075058 A1 | 4/2004 | Blevis et al. |
| 2004/0081623 A1 | 4/2004 | Eriksen et al. |
| 2004/0082918 A1 | 4/2004 | Evans et al. |
| 2004/0084340 A1 | 5/2004 | Morelle et al. |
| 2004/0086437 A1 | 5/2004 | Jackson et al. |
| 2004/0101176 A1 | 5/2004 | Mendonca et al. |
| 2004/0101177 A1 | 5/2004 | Zahlmann et al. |
| 2004/0116807 A1 | 6/2004 | Amrami et al. |
| 2004/0120557 A1 | 6/2004 | Sabol |
| 2004/0122311 A1 | 6/2004 | Cosman |
| 2004/0125918 A1 | 7/2004 | Shanmugavel et al. |
| 2004/0138557 A1 | 7/2004 | Le et al. |
| 2004/0143449 A1 | 7/2004 | Behrenbruch et al. |
| 2004/0144925 A1 | 7/2004 | Stoddart et al. |
| 2004/0153128 A1 | 8/2004 | Suresh et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |
| 2004/0195512 A1 | 10/2004 | Crosetto |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2004/0258201 A1 | 12/2004 | Hayashida |
| 2004/0263865 A1 | 12/2004 | Pawlak et al. |
| 2005/0001170 A1 | 1/2005 | Juni |
| 2005/0006589 A1 | 1/2005 | Young et al. |
| 2005/0020898 A1 | 1/2005 | Vosniak et al. |
| 2005/0020915 A1 | 1/2005 | Bellardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0113960 A1 | 5/2005 | Karau et al. |
| 2005/0117029 A1 | 6/2005 | Shiomi |
| 2005/0121505 A1 | 6/2005 | Metz et al. |
| 2005/0123183 A1* | 6/2005 | Schleyer ............... G06T 11/005 382/131 |
| 2005/0131270 A1 | 6/2005 | Weil et al. |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0207526 A1 | 9/2005 | Altman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1* | 1/2006 | Charron ............... G01T 1/1641 250/394 |
| 2006/0033028 A1 | 2/2006 | Juni |
| 2006/0036157 A1 | 2/2006 | Tumer |
| 2006/0072799 A1 | 4/2006 | McLain |
| 2006/0074290 A1 | 4/2006 | Chen et al. |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0081700 A1 | 4/2007 | Blumenfeld et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0183582 A1 | 8/2007 | Baumann et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0137938 A1 | 6/2008 | Zahniser |
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0051643 A1 | 2/2013 | Jackson et al. |
| 2013/0114792 A1 | 5/2013 | Zilberstein et al. |
| 2013/0308749 A1 | 11/2013 | Zilberstein et al. |
| 2014/0151563 A1 | 6/2014 | Rousso et al. |
| 2014/0163368 A1 | 6/2014 | Rousso et al. |
| 2014/0187927 A1 | 7/2014 | Nagler et al. |
| 2014/0193336 A1 | 7/2014 | Rousso et al. |
| 2014/0200447 A1 | 7/2014 | Rousso et al. |
| 2014/0249402 A1 | 9/2014 | Kimchy et al. |
| 2016/0253826 A9 | 9/2016 | Ziv et al. |
| 2017/0000505 A1 | 1/2017 | Gordon et al. |

(56) References Cited

U.S. PATENT DOCUMENTS

| | | | |
|---|---|---|---|
| 2017/0007193 A1 | 1/2017 | Nagler et al. | |
| 2018/0235557 A1 | 8/2018 | Rousso et al. | |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| JP | 2003-098259 | 4/2003 |
| WO | WO 92/00402 | 1/1992 |
| WO | WO 97/42524 | 11/1997 |
| WO | WO 1998/016852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/25268 | 5/2000 |
| WO | WO 00/31522 | 6/2000 |
| WO | WO 00/38197 | 6/2000 |
| WO | WO 00/62093 | 10/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/016166 | 2/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Parker, Geoffrey JM, et al. "Probing tumor microvascularity by measurement, analysis and display of contrast agent uptake kinetics." Journal of Magnetic Resonance Imaging 7.3 (1997): 564-574.*
Boucher, Luc, et al. "Respiratory gating for 3-dimensional PET of the thorax: feasibility and initial results." Journal of Nuclear Medicine 45.2 (2004): 214-219.*
Advisory Action Before the Filing of an Appeal Brief dated Apr. 14, 2017 From the US Patent and Trademark Office Re. U.S. Appl. No. 14/058,363. (3 pages).
Applicant-Initiated Interview Summary dated Oct. 6, 2017 From the US Patent and Trademark Office Re. U.S. Appl. No. 14/100,082. (3 Pages).
Communication Pursuant to Article 94(3) EPC dated Jan. 5, 2018 From the European Patent Office Re. Application No. 05703091.8. (4 Pages).
Communication Pursuant to Article 94(3) EPC dated Nov. 10, 2017 From the European Patent Office Re. Application No. 05747259.9. (3 Pages).
Communication Pursuant to Article 94(3) EPC dated May 15, 2017 From the European Patent Office Re. Application No. 01951883.6. (10 Pages).
Communication Pursuant to Rule 164(1) EPC [Supplementary Partial European Search Report] dated Mar. 1, 2017 From the European Patent Office Re. Application No. 06700631.2. (7 pages).
Communication Pursuant to Rule 164(1) EPC [Supplementary Partial European Search Report] dated Feb. 17, 2017 From the European Patent Office Re. Application No. 05803158.4. (8 Pages).
Corrected European Search Opinion dated Sep. 19, 2017 From the European Patent Office Re. Application No. 06700631.2. (5 Pages).
Invitation Pursuant to Rule 62a(1) EPC dated Apr. 7, 2017 From the European Patent Office Re. Application No. 10171259.4. (2 Pages).
Notice of Allowance dated Dec. 6, 2017 From the US Patent and Trademark Office Re. U.S. Appl. No. 14/100,082. (10 pages).
Official Action dated Feb. 2, 2017 From the US Patent and Trademark Office Re. U.S. Appl. No. 14/058,363. (9 pages).
Official Action dated Feb. 8, 2017 From the US Patent and Trademark Office Re. U.S. Appl. No. 14/100,082. (182 pages).
Official Action dated Jun. 9, 2017 From the US Patent and Trademark Office Re. U.S. Appl. No. 14/100,082. (41 Pages).
Official Action dated Jul. 17, 2017 From the US Patent and Trademark Office Re. U.S. Appl. No. 14/058,363. (21 pages).
Official Action dated Apr. 21, 2017 From the US Patent and Trademark Office Re. U.S. Appl. No. 15/184,041. (76 pages).
Partial European Search Report dated Jul. 21, 2017 From the European Patent Office Re. Application No. 10171259.4. (13 Pages).
Supplementary European Search Report and the European Search Opinion dated Jun. 6, 2017 From the European Patent Office Re. Application No. 06700631.2. (10 Pages).
Supplementary European Search Report and the European Search Opinion dated Jun. 14, 2017 From the European Patent Office Re. Application No. 05803158.4. (13 Pages).
Chiao et al. "Compartment Analysis of Technetium-99m-Teboroxime Kinetics Employing Fast Dynamic SPECT at Rest and Stress", The Journal of Nuclear Medicine, XP055347116, 35(8): 1265-1273, Aug. 1994. Abstract, Sections 'Imaging Protocol', 'Data Analysis', 'Quantification of Myocardial Blood Flow—Next Step'.
Garcia et al. "Diagnostic Performance of an Expert System for the Interpretation of Myocardial Perfusion SPECT Studies", The Journal of Nuclear Medicine, XP055347227, 42(8): 1185-1191, Aug. 2001. Abstract, Section 'Data Analysis and Expert System Interpretation'.
Graham et al. "Quatitation of SPECT Performance: Report of Task Group 4, Nuclear Medicine Committee", American Association of Physicists in Medicine, AAPM Report No. 52, XP055341256, 22(4): 401-409, Apr. 1995. Abstract, Section II. B. 'Spatial Resolution', Section II. C. 'Tomographic Uniformity', Section III. A.2. 'Spatial Resolution', Section III. A.3. 'System Performance: Tomographic Uniformity and Contrast'.
Advisory Action Before the Filing of an Appeal Brief dated Jul. 12, 2012 From the US Patent and Trademark Office Re. U.S. Appl. No. 11/667,793.

(56) References Cited

OTHER PUBLICATIONS

Advisory Action before the Filing of an Appeal Brief dated May 21, 2013 From the US Patent and Trademark Office Re. U.S. Appl. No. 11/980,653.
Advisory Action Before the Filing of an Appeal Brief dated Feb. 26, 2013 From the US Patent and Trademark Office Re. U.S. Appl. No. 11/989,223.
Amendment After Allowance Under 37 CFR 1.312 dated Sep. 13, 2010 to Notice of Allowance dated Jul. 22, 2010 From the US Patent and Trademark Office Re.: U.S. Appl. No. 11/794,799.
Appeal Brief Dated Jan. 19, 2010 to Notice of Appeal of Nov. 16, 2009 From the US Patent and Trademark Office Re. U.S. Appl. No. 10/616,301.
Applicant-Initiated Interview Summary dated May 1, 2013 From the US Patent and Trademark Office Re. U.S. Appl. No. 10/343,792.
Applicant-Initiated Interview Summary dated May 9, 2013 From the US Patent and Trademark Office Re. U.S. Appl. No. 12/448,473.
Applicant-Initiated Interview Summary dated Jun. 11, 2015 From the US Patent and Trademark Office Re. U.S. Appl. No. 14/214,960.
Applicant-Initiated Interview Summary dated Mar. 20, 2014 From the US Patent and Trademark Office Re. U.S. Appl. No. 12/087,150.
Applicant-Initiated Interview Summary dated Jan. 28, 2013 From the US Patent and Trademark Office Re. U.S. Appl. No. 11/798,017.
Applicant-Initiated Interview Summary dated Jan. 29, 2014 From the US Patent and Trademark Office Re. U.S. Appl. No. 13/345,773.
Applicant-Interview Summary dated Mar. 21, 2012 From the US Patent and Trademark Office Re. U.S. Appl. No. 12/514,785.
Communication Pursuant to Article 94(3) EPC dated Mar. 2, 2011 From the European Patent Office Re. Application No. 06756259.5.
Communication Pursuant to Article 94(3) EPC dated May 8, 2014 From the European Patent Office Re. Application No. 05803689.8.
Communication Pursuant to Article 94(3) EPC dated Oct. 10, 2014 From the European Patent Office Re. Application No. 05803689.8.
Communication Pursuant to Article 94(3) EPC dated Jun. 11, 2012 From the European Patent Office Re. Application No. 06756259.5.
Communication Pursuant to Article 94(3) EPC dated May 12, 2010 From the European Patent Office Re. Application No. 06809851.6.
Communication Pursuant to Article 94(3) EPC dated Nov. 12, 2012 From the European Patent Office Re. Application No. 06756258.7.
Communication Pursuant to Article 94(3) EPC dated Apr. 16, 2010 From the European Patent Office Re. Application No. 01951883.6.
Communication Pursuant to Article 94(3) EPC dated Sep. 2013 From the European Patent Office Re.: Application No. 06832278.3.
Communication Pursuant to Article 94(3) EPC dated Oct. 17, 2014 From the European Patent Office Re. Application No. 06809851.6.
Communication Pursuant to Article 94(3) EPC dated Nov. 18, 2011 From the European Patent Office Re. Application No. 05803689.8.
Communication Pursuant to Article 94(3) EPC dated Oct. 21, 2009 From the European Patent Office Re.: Application No. 02716285.8.
Communication Pursuant to Article 94(3) EPC dated Jul. 22, 2009 From the European Patent Office Re.: Application No. 06809851.6.
Communication Pursuant to Article 94(3) EPC dated Sep. 2011 From the European Patent Office Re. Application No. 06756258.7.
Communication Pursuant to Article 94(3) EPC dated Nov. 25, 2013 From the European Patent Office Re. Application No. 06756258.7.
Communication Pursuant to Article 94(3) EPC dated Oc. 26, 2012 From the European Patent Office Re. Application No. 05803689.8.
Communication Pursuant to Article 94(3) EPC dated May 29, 2012 From the European Patent Office Re. Application No. 05803689.8.
Communication Pursuant to Article 96(2) EPC dated Jun. 19, 2006 From the European Patent Office Re.: Application No. 03810570.6.
Communication Pursuant to Article 96(2) EPC dated Aug. 30, 2007 From the European Patent Office Re. Application No. 03810570.6.
Communication Relating to the Results of the Partial International Search dated Apr. 18, 2007 From the International Searching Authority of the Patent Cooperation Treaty Re.: Application No. PCT/IL2006/001291.
Communication Relating to the Results of the Partial International Search dated May 21, 2008 From the International Searching Authority of the Patent Cooperation Treaty Re.: Application No. PCT/IL2007/001588.
Examination Report dated Jun. 22, 2011 From the Government of India, Patent Office, Intellectual Property Building Re. Application No. 2963/CHENP/2006.
International Preliminary Report on Patentability dated Apr. 7, 2009 From the International Bureau of WIPO Re. Application No. PCT/IL2007/000918.
International Preliminary Report on Patentability dated Jan. 13, 2009 From the International Bureau of WIPO Re. Application No. PCT/IL2006/000834.
International Preliminary Report on Patentability dated May 14, 2008 From the International Bureau of WIPO Re. Application No. PCT/IL2006/001291.
International Preliminary Report on Patentability dated May 15, 2007 From the International Bureau of WIPO Re. Application No. PCT/IL2005/001173.
International Preliminary Report on Patentability dated Apr. 16, 2009 From the International Bureau of WIPO Re. Applicaiton No. PCT/IL007/000918.
International Preliminary Report on Patentability dated Jun. 21, 2007 From the International Bureau of WIPO Re. Application No. PCT/IL2005/000575.
International Preliminary Report on Patentability dated Jan. 22, 2009 From the International Bureau of WIPO Re.: Application No. PCT/IL2006/000834.
International Preliminary Report on Patentability dated May 22, 2007 From the International Preliminary Examining Authority Re.: Application No. PCT/IL06/00059.
International Preliminary Report on Patentability dated May 22, 2008 From the International Bureau of WIPO Re. Application No. PCT/IL2006/001291.
International Preliminary Report on Patentability dated May 24, 2007 From the International Bureau of WIPO Re.: Application No. PCT/IL2005/001173.
International Preliminary Report on Patentability dated Apr. 26, 2007 From the International Bureau of WIPO Re.: Application No. PCT/IL2005/000394.
International Preliminary Report on Patentability dated Jan. 31, 2008 From the International Bureau of WIPO Re.: Application No. PCT/IL2006/000840.
International Search Report dated Oct. 10, 2006 From the International Searching Authority of the Patent Cooperation Treaty Re.: Application No. PCT/IL06/00059.
International Search Report dated Jul. 25, 2008 From the International Searching Authority of the Patent Cooperation Treaty Re.: Application No. PCT/IL2007/001588.
International Search Report dated Feb. 1, 2006 From the International Searching Authority of the Patent Cooperation Treaty Re.: Application No. PCT/IL05/00048.
International Search Report dated Jul. 1, 2008 From the International Searching Authority of the Patent Cooperation Treaty Re.: Application No. PCT/IL06/00834.
International Search Report dated Jul. 1, 2008 From the International Searching Authority Re. Application No. PCT/IL2006/000834.
International Search Report dated Nov. 1, 2007 From the International Searching Authority of the Patent Cooperation Treaty Re.: Application No. PCT/IL06/00840.
International Search Report dated Jul. 2, 2007 From the International Searching Authority of the Patent Cooperation Treaty Re.: Application No. PCT/IL2006/001291.
International Search Report dated Jul. 2, 2007 From the International Searching Authority Re. Application No. PCT/IL2006/001291.
International Search Report dated Aug. 3, 2006 From the International Searching Authority of the Patent Cooperation Treaty Re.: Application No. PCT/IL05/001173.
International Search Report dated Aug. 3, 2006 From the International Searching Authority Re. Application No. PCT/IL2005/001173.

(56) References Cited

OTHER PUBLICATIONS

International Search Report dated May 11, 2006 From the International Searching Authority of the Patent Cooperation Treaty Re.: Application No. PCT/IL05/001215.
International Search Report dated Sep. 11, 2002 From the International Searching Authority Re. Application No. PCT/IL01/00638.
International Search Report dated Sep. 12, 2002 From the International Searching Authority of the Patent Cooperation Treaty Re: Application No. PCT/IL02/00057.
International Search Report dated Oct. 15, 2008 From the International Searching Authority Re. Application No. PCT/2007/000918.
International Search Report dated Oct. 15, 2008 From the International Searching Authority Re. Application No. PCT/IL07/00918.
International Search Report dated Mar. 18, 2004 From the International Searching Authority of the Patent Cooperation Treaty Re.: Application No. PCT/IL03/00917.
International Search Report dated Mar. 23, 2006 From the International Searching Authority of the Patent Cooperation Treaty Re.: Application No. PCT/IL05/00572.
International Search Report dated May 24, 2007 From the International Searching Authority of the Patent Cooperation Treaty Re.: Application No. PCT/IL05/00575.
International Search Report dated Mar. 26, 2007 From the International Searching Authority of the Patent Cooperation Treaty Re.: Application No. PCT/IL05/00394.
Interview Summary dated Mar. 25, 2011 From the US Patent and Trademark Office Re.: U.S. Appl. No. 10/836,223.
Interview Summary dated May 31, 2011 From the US Patent and Trademark Office Re. U.S. Appl. No. 10/616,301.
Invitation to Pay Additional Fees dated Feb. 15, 2007 From the International Searching Authority Re. Application No. PCT/IL05/00575.
Notice of Appeal and Pre-Appeal Brief Dated Jan. 4, 2010 to Official Action dated Sep. 2, 2009 From the US Patent and Trademark Office Re.: U.S. Appl. No. 10/343,792.
Notice of Appeal Dated Nov. 16, 2009 to Official Action dated Jul. 15, 2009 From the US Patent and Trademark Office Re. U.S. Appl. No. 10/616,301.
Notice of Non-Compliant Amendment dated Feb. 14, 2011 From the US Patent and Trademark Office Re: U.S. Appl. No. 10/616,307.
Notice of Non-Compliant Amendment dated Jul. 15, 2016 From the US Patent and Trademark Office Re. U.S. Appl. No. 14/058,363.
Notice of Panel Decision From Pre-Appeal Brief Review dated Feb. 29, 2012 From the US Patent and Trademark Office Re. U.S. Appl. No. 10/836,223.
Office Action dated Dec. 2, 2007 From the Israeli Patent Office Re. Application No. 158442.
Office Action dated Jan. 2, 2006 From the Israeli Patent Office Re. Application No. 154323.
Office Action dated Sep. 4, 2007 From the Israeli Patent Office Re.: Application No. 157007.
Office Action dated Jul. 17, 2007 From the Israeli Patent Office Re. Application No. 154323 and Its Translation Into English.
Office Action dated Jul. 17, 2007 From the Israeli Patent Office Re. Application No. 154323.
Official Action dated Jun. 1, 2006 From the US Patent and Trademark Office Re. U.S. Appl. No. 10/686,536.
Official Action dated Mar. 1, 2010 From the US Patent and Trademark Office Re. U.S. Appl. No. 11/794,799.
Official Action dated Mar. 1, 2012 From the US Patent and Trademark Office Re. U.S. Appl. No. 10/616,307.
Official Action dated Nov. 1, 2010 From the US Patent and Trademark Office Re. U.S. Appl. No. 12/728,383.
Official Action dated Sep. 1, 2009 From the US Patent and Trademark Office Re.: U.S. Appl. No. 11/794,799.
Official Action dated Jul. 2, 2004 From the US Patent and Trademark Office Re. U.S. Appl. No. 09/641,973.
Official Action dated Mar. 2, 2010 From the US Patent and Trademark Office Re. U.S. Appl. No. 10/836,223.
Official Action dated Mar. 2, 2010 From the US Patent and Trademark Office Re. U.S. Appl. No. 11/980,617.
Official Action dated Sep. 2, 2009 From the US Patent and Trademark Office Re.: U.S. Appl. No. 10/343,792.
Official Action dated Aug. 3, 2010 From the US Patent and Trademark Office Re. U.S. Appl. No. 11/980,690.
Official Action dated May 3, 2007 From the US Patent and Trademark Office Re. U.S. Appl. No. 10/240,239.
Official Action dated Aug. 4, 2015 From the US Patent and Trademark Office Re. U.S. Appl. No. 14/082,314.
Official Action dated Sep. 4, 2008 From the US Patent and Trademark Office Re.: U.S. Appl. No. 10/533,568.
Official Action dated Aug. 5, 2013 From the US Patent and Trademark Office Re. U.S. Appl. No. 12/309,479.
Official Action dated Jul. 5, 2013 From the US Patent and Trademark Office Re. U.S. Appl. No. 11/656,548.
Official Action dated Sep. 5, 2002 From the US Patent and Trademark Office Re. U.S. Appl. No. 12/084,559.
Official Action dated Sep. 5, 2013 From the US Patent and Trademark Office Re. U.S. Appl. No. 13/947,198.
Official Action dated Mar. 6, 2012 From the US Patent and Trademark Office Re. U.S. Appl. No. 12/792,856.
Official Action dated Feb. 7, 2013 From the US Patent and Trademark Office Re. U.S. Appl. No. 11/980,653.
Official Action dated Jan. 7, 2009 From the US Patent and Trademark Office Re.: U.S. Appl. No. 10/616,307.
Official Action dated Jul. 7, 2009 From the US Patent and Trademark Office Re.: U.S. Appl. No. 10/533,568.
Official Action dated Oct. 7, 2008 From the US Patent and Trademark Office Re.: U.S. Appl. No. 10/616,301.
Official Action dated Oct. 7, 2011 From the US Patent and Trademark Office Re. U.S. Appl. No. 11/750,057.
Official Action dated Oct. 7, 2011 From the US Patent and Trademark Office Re. U.S. Appl. No. 11/932,872.
Official Action dated Apr. 8, 2010 From the US Patent and Trademark Office Re. U.S. Appl. No. 11/980,690.
Official Action dated Dec. 8, 2009 From the US Patent and Trademark Office Re. U.S. Appl. No. 11/132,320.
Official Action dated Dec. 8, 2010 From the US Patent and Trademark Office Re. U.S. Appl. No. 09/641,973.
Official Action dated Dec. 8, 2010 From the US Patent and Trademark Office Re. U.S. Appl. No. 11/980,690.
Official Action dated Jan. 8, 2010 From the US Patent and Trademark Office Re. U.S. Appl. No. 11/656,548.
Official Action dated Jul. 8, 2015 From the US Patent and Trademark Office Re. U.S. Appl. No. 11/667,793.
Official Action dated Apr. 9, 2010 From the US Patent and Trademark Office Re. U.S. Appl. No. 11/798,017.
Official Action dated Mar. 9, 2011 From the US Patent and Trademark Office Re.: U.S. Appl. No. 10/616,301.
Official Action dated Aug. 10, 2007 From the US Patent and Trademark Office Re. U.S. Appl. No. 10/836,223.
Official Action dated Feb. 10, 2014 From the US Patent and Trademark Office Re. U.S. Appl. No. 11/667,793.
Official Action dated Nov. 10, 2010 From the US Patent and Trademark Office Re. U.S. Appl. No. 10/616,307.
Official Action dated Nov. 10, 2010 From the US Patent and Trademark Office Re.: U.S. Appl. No. 10/836,223.
Official Action dated Oct. 10, 2012 From the US Patent and Trademark Office Re. U.S. Appl. No. 11/798,017.
Official Action dated Apr. 11, 2014 From the US Patent and Trademark Office Re. U.S. Appl. No. 12/309,479.
Official Action dated Aug. 11, 2009 From the US Patent and Trademark Office Re. U.S. Appl. No. 09/641,973.
Official Action dated Jul. 11, 2011 From the US Patent and Trademark Office Re. U.S. Appl. No. 11/980,683.
Official Action dated Mar. 11, 2010 From the US Patent and Trademark Office Re. U.S. Appl. No. 11/607,075.
Official Action dated Mar. 11, 2013 From the US Patent and Trademark Office Re. U.S. Appl. No. 13/345,719.
Official Action dated Oct. 11, 2012 From the US Patent and Trademark Office Re. U.S. Appl. No. 11/976,852.

(56) References Cited

OTHER PUBLICATIONS

Official Action dated Dec. 12, 2014 From the US Patent and Trademark Office Re. U.S. Appl. No. 12/448,473.
Official Action dated Jul. 12, 2007 From the US Patent and Trademark Office Re.: U.S. Appl. No. 10/616,301.
Official Action dated Jul. 12, 2011 From the US Patent and Trademark Office Re. U.S. Appl. No. 09/641,973.
Official Action dated Aug. 13, 2008 From the US Patent and Trademark Office Re. U.S. Appl. No. 11/769,826.
Official Action dated Dec. 13, 2007 From the US Patent and Trademark Office Re.: U.S. Appl. No. 10/616,301.
Official Action dated May 13, 2009 From the US Patent and Trademark Office Re. U.S. Appl. No. 11/798,017.
Official Action dated May 13, 2014 From the US Patent and Trademark Office Re. U.S. Appl. No. 12/448,473.
Official Action dated Sep. 13, 2011 From the US Patent and Trademark Office Re. U.S. Appl. No. 11/976,852.
Official Action dated Aug. 14, 2013 From the US Patent and Trademark Office Re. U.S. Appl. No. 12/448,473.
Official Action dated May 14, 2009 From the US Patent and Trademark Office Re. U.S. Appl. No. 11/656,548.
Official Action dated Apr. 15, 2008 From the US Patent and Trademark Office Re. U.S. Appl. No. 09/641,973.
Official Action dated Apr. 15, 2015 From the US Patent and Trademark Office Re. U.S. Appl. No. 14/214,960.
Official Action dated Dec. 15, 2006 From the US Patent and Trademark Office Re. U.S. Appl. No. 10/616,301.
Official Action dated Dec. 15, 2011 From the US Patent and Trademark Office Re. U.S. Appl. No. 10/343,792.
Official Action dated Dec. 15, 2015 From the US Patent and Trademark Office Re. U.S. Appl. No. 11/667,793.
Official Action dated Feb. 15, 2008 From the US Patent and Trademark Office Re. U.S. Appl. No. 10/343,792.
Official Action dated Jul. 15, 2008 From the US Patent and Trademark Office Re. U.S. Appl. No. 09/641,973.
Official Action dated Jul. 15, 2009 From the US Patent and Trademark Office Re.: U.S. Appl. No. 10/616,301.
Official Action dated Mar. 15, 2004 From the US Patent and Trademark Office Re. U.S. Appl. No. 09/765,316.
Official Action dated Mar. 15, 2011 From the US Patent and Trademark Office Re. U.S. Appl. No. 10/343,792.
Official Action dated Nov. 15, 2013 From the US Patent and Trademark Office Re. U.S. Appl. No. 13/345,773.
Official Action dated Sep. 15, 2009 From the US Patent and Trademark Office Re.: U.S. Appl. No. 10/616,307.
Official Action dated Sep. 15, 2009 From the US Patent and Trademark Office Re.: U.S. Appl. No. 10/836,223.
Official Action dated Sep. 15, 2015 From the US Patent and Trademark Office Re. U.S. Appl. No. 14/147,682.
Official Action dated Apr. 16, 2012 From the US Patent and Trademark Office Re.: U.S. Appl. No. 10/836,223.
Official Action dated Dec. 16, 2008 From the US Patent and Trademark Office Re.: U.S. Appl. No. 10/343,792.
Official Action dated Feb. 16, 2012 From the US Patent and Trademark Office Re. U.S. Appl. No. 11/747,378.
Official Action dated Sep. 16, 2009 From the US Patent and Trademark Office Re. U.S. Appl. No. 09/727,464.
Official Action dated Jan. 17, 2006 From the United States Patent and Trademark Office Re.: U.S. Appl. No. 11/034,007.
Official Action dated Jun. 17, 2014 From the US Patent and Trademark Office Re. U.S. Appl. No. 12/087,150.
Official Action dated May 18, 2012 From the US Patent and Trademark Office Re. U.S. Appl. No. 11/989,223.
Official Action dated May 18, 2012 From the US Patent and Trademark Office Re. U.S. Appl. No. 12/514,785.
Official Action dated Apr. 19, 2012 From the US Patent and Trademark Office Re. U.S. Appl. No. 11/750,057.
Official Action dated Dec. 19, 2012 From the US Patent and Trademark Office Re. U.S. Appl. No. 12/448,473.
Official Action dated Jan. 19, 2012 From the US Patent and Trademark Office Re. U.S. Appl. No. 11/667,793.
Official Action dated Jul. 19, 2010 From the US Patent and Trademark Office Re. U.S. Appl. No. 11/607,075.
Official Action dated Jul. 19, 2010 From the US Patent and Trademark Office Re. U.S. Appl. No. 11/656,548.
Official Action dated Mar. 19, 2010 From the US Patent and Trademark Office Re. U.S. Appl. No. 10/240,239.
Official Action dated Apr. 20, 2006 From the United States Patent and Trademark Office Re. U.S. Appl. No. 10/240,239.
Official Action dated Apr. 20, 2011 From the US Patent and Trademark Office Re. U.S. Appl. No. 11/798,017.
Official Action dated Dec. 20, 2011 From the US Patent and Trademark Office Re. U.S. Appl. No. 12/309,479.
Official Action dated Jul. 20, 2009 From the US Patent and Trademark Office Re. U.S. Appl. No. 11/980,617.
Official Action dated Jun. 21, 2012 From the US Patent and Trademark Office Re. U.S. Appl. No. 12/309,479.
Official Action dated Mar. 21, 2008 From the US Patent and Trademark Office Re.: U.S. Appl. No. 10/533,568.
Official Action dated Sep. 21, 2009 From the US Patent and Trademark Office Re. U.S. Appl. No. 11/798,017.
Official Action dated Dec. 22, 2011 From the US Patent and Trademark Office Re. U.S. Appl. No. 12/514,785.
Official Action dated Feb. 22, 2013 From the US Patent and Trademark Office Re. U.S. Appl. No. 10/616,307.
Official Action dated Apr. 23, 2012 From the US Patent and Trademark Office Re. U.S. Appl. No. 11/932,987.
Official Action dated Dec. 23, 2008 From the US Patent and Trademark Office Re. U.S. Appl. No. 09/727,464.
Official Action dated Feb. 23, 2010 From the US Patent and Trademark Office Re. U.S. Appl. No. 09/641,973.
Official Action dated Jun. 23, 2006 From the United States Patent and Trademark Office Re. U.S. Appl. No. 09/727,464.
Official Action dated May 23, 2011 From the US Patent and Trademark Office Re. U.S. Appl. No. 10/616,307.
Official Action dated May 23, 2011 From the US Patent and Trademark Office Re. U.S. Appl. No. 11/667,793.
Official Action dated May 23, 2011 From the US Patent and Trademark Office Re. U.S. Appl. No. 11/980,690.
Official Action dated Nov. 23, 2010 From the US Patent and Trademark Office Re. U.S. Appl. No. 11/656,548.
Official Action dated Jun. 25, 2008 From the US Patent and Trademark Office Re.: U.S. Appl. No. 10/616,301.
Official Action dated Sep. 25, 2006 From the US Patent and Trademark Office Re.: U.S. Appl. No. 10/616,301.
Official Action dated Aug. 26, 2016 From the US Patent and Trademark Office Re. U.S. Appl. No. 14/058,363.
Official Action dated Mar. 26, 2015 From the US Patent and Trademark Office Re. U.S. Appl. No. 14/147,682.
Official Action dated May 26, 2016 From the US Patent and Trademark Office Re. U.S. Appl. No. 14/214,960.
Official Action dated Nov. 26, 2008 From the US Patent and Trademark Office Re. U.S. Appl. No. 10/240,239.
Official Action dated Oct. 26, 2011 From the US Patent and Trademark Office Re.: U.S. Appl. No. 10/836,223.
Official Action dated Apr. 27, 2011 From the US Patent and Trademark Office Re. U.S. Appl. No. 10/836,223.
Official Action dated Jul. 27, 2010 From the US Patent and Trademark Office Re.: U.S. Appl. No. 10/616,307.
Official Action dated Oct. 27, 2011 From the US Patent and Trademark Office Re. U.S. Appl. No. 11/656,548.
Official Action dated Apr. 28, 2010 From the US Patent and Trademark Office Re.: U.S. Appl. No. 10/616,301.
Official Action dated Aug. 28, 2009 From the US Patent and Trademark Office Re. U.S. Appl. No. 10/240,239.
Official Action dated Dec. 28, 2010 From the US Patent and Trademark Office Re.: U.S. Appl. No. 11/607,075.
Official Action dated Dec. 28, 2012 From the US Patent and Trademark Office Re. U.S. Appl. No. 10/343,792.
Official Action dated Feb. 28, 2012 From the US Patent and Trademark Office Re. U.S. Appl. No. 09/641,973.

(56) References Cited

OTHER PUBLICATIONS

Official Action dated Jan. 28, 2011 From the US Patent and Trademark Office Re. U.S. Appl. No. 09/641,973.
Official Action dated Jun. 28, 2011 From the US Patent and Trademark Office Re. U.S. Appl. No. 11/628,074.
Official Action dated Apr. 29, 2009 From the US Patent and Trademark Office Re.: U.S. Appl. No. 11/980,690.
Official Action dated Oct. 29, 2015 From the US Patent and Trademark Office Re. U.S. Appl. No. 14/214,960.
Official Action dated Jul. 30, 2012 From the US Patent and Trademark Office Re. U.S. Appl. No. 11/980,683.
Official Action dated Jul. 30, 2013 From the US Patent and Trademark Office Re. U.S. Appl. No. 10/343,792.
Official Action dated Nov. 30, 2012 From the US Patent and Trademark Office Re. U.S. Appl. No. 11/989,223.
Official Action dated Oct. 2009 From the US Patent and Trademark Office Re.: U.S. Appl. No. 11/980,690.
Official Action dated Sep. 30, 2008 From the US Patent and Trademark Office Re. U.S. Appl. No. 10/616,301.
Official Action dated Sep. 30, 2010 From the US Patent and Trademark Office Re. U.S. Appl. No. 11/798,017.
Official Action dated Aug. 31, 2012 From the US Patent and Trademark Office Re. U.S. Appl. No. 11/980,653.
Official Action dated Jan. 31, 2011 From the US Patent and Trademark Office Re. U.S. Appl. No. 11/667,793.
Official Action dated Jul. 31, 2013 From the US Patent and Trademark Office Re. U.S. Appl. No. 11/667,793.
Proceeding Further With the European Patent Application Pursuant to Rule 70(2) EPC Dated Nov. 10, 2015 From the European Patent Office Re. Application No. 05703091.8.
Proceeding Further With the European Patent Application Pursuant to Rule 70(2) EPC Dated Dec. 11, 2015 From the European Patent Office Re. Application No. 05747259.9.
Restriction Official Action dated Nov. 8, 2011 From the US Patent and Trademark Office Re. U.S. Appl. No. 12/309,479.
Restriction Official Action dated Mar. 9, 2012 From the US Patent and Trademark Office Re. U.S. Appl. No. 11/976,852.
Restriction Official Action dated Sep. 12, 2011 From the US Patent and Trademark Office Re. U.S. Appl. No. 11/980,653.
Restriction Official Action dated Apr. 13, 2012 From the US Patent and Trademark Office Re. U.S. Appl. No. 11/989,223.
Restriction Official Action dated Nov. 15, 2011 From the US Patent and Trademark Office Re. U.S. Appl. No. 11/980,683.
Restriction Official Action dated Aug. 16, 2012 From the US Patent and Trademark Office Re. U.S. Appl. No. 12/448,473.
Restriction Official Action dated Apr. 21, 2016 From the US Patent and Trademark Office Re. U.S. Appl. No. 14/058,363.
Second International Search Report dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Summons to Attend Oral Proceedings Pursuant to Rule 115(1) EPC Dated Nov. 29, 2012 From the European Patent Office Re. Application No. 06756259.5.
Supplementary European Search Report and the European Search Opinion dated Nov. 13, 2012 From the European Patent Office Re. Application No. 06728347.3.
Supplementary European Search Report and the European Search Opinion dated Mar. 16, 2011 From the European Patent Office Re. Application No. 05803689.8.
Supplementary European Search Report dated Dec. 12, 2005 From the European Patent Office Re Application No. 03810570.6.
Supplementary European Search Report dated Oct. 22, 2015 From the European Patent Office Re. Application No. 05703091.8.
Supplementary European Search Report dated Nov. 25, 2015 From the European Patent Office Re. Application No. 05747259.9.
Supplementary Partial European Search Report and the European Search Opinion dated Oct. 16, 2009 From the European Patent Office Re.: Application No. 06756259.5.
Supplementary Partial European Search Report dated Sep. 4, 2007 From the European Patent Office Re. Application No. 0 2716285.8.
Supplementary Partial European Search Report dated Nov. 11, 2008 From the European Patent Office Re. Application No. 01951883.6.
Supplementary Partial European Search Report dated Nov. 20, 2007 From the European Patent Office Re. Application No. 02716285.8.
Translation of Office Action dated May 13, 2005 From the Patent Office of the People's Republic of China Re. Application No. 01817689.5.
Written Opinion dated Feb. 1, 2006 From the International Searching Authority of the Patent Cooperation Treaty Re.: Application No. PCT/IL05/00048.
Written Opinion dated Jul. 1, 2008 From the International Searching Authority Re. Application No. PCT/IL06/00834.
Written Opinion dated Nov. 1, 2007 from the International Searching Authority of the Patent Cooperation Treaty Re.: Application No. PCT/IL06/00840.
Written Opinion dated Jul. 2, 2007 From the International Searching Authority of the Patent Cooperation Treaty Re.: Application No. PCT/IL2006/001291.
Written Opinion dated Aug. 3, 2006 From the International Searching Authority of the Patent Cooperation Treaty Re.: Application No. PCT/IL05/001173.
Written Opinion dated Oct. 10, 2006 From the International Searching Authority of the Patent Cooperation Treaty Re. Application No. PCT/IL06/00059.
Written Opinion dated Oct. 15, 2008 From the International Searching Authority Re. Application No. PCT/IL07/00918.
Written Opinion dated Mar. 23, 2006 From the International Searching Authority of the Patent Cooperation Treaty Re. Application No. PCT/IL05/00572.
Written Opinion dated May 24, 2007 From the International Searching Authority of the Patent Cooperation Treaty Re.: Application No. PCT/IL05/00575.
Written Opinion dated Jul. 25, 2008 From the International Searching Authority of the Patent Cooperation Treaty Re.: Application No. PCT/IL05/001173.
Written Opinion dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Berman et al. "D-SPECT: A Novel Camera for High Speed Quantitative Molecular Imaging: Initial Clinical Results", The Journal of Nuclear Medicine, 47(Suppl.1): 131P, 2006.
Berman et al. "Dual-Isotope Myocardial Perfusion SPECT With Rest Thallium-201 and Stress Tc-99m Sestamibi", Nuclear Cardiology, 12(2): 261-270, May 1994.
Berman et al. "Myocardial Perfusion Imaging With Technetium-99m-Sestamibi: Comparative Analysis of Available Imaging Protocols", The Journal of Nuclear Medicine, 35: 681-688, 1994.
Bloch et al. "Application of Computerized Tomography to Radiation Therapy and Surgical Planning", Proceedings of the IEEE, 71(3): 351-355, Mar. 1983.
Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.
Bowsher et al. "Treatment of Compton Scattenng in Maximum-Likelihood, Expectation-Maximization Reconstructions of SPECT Images", Journal of Nuclear Medicine, 32(6): 1285-1291, 1991.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.

(56) References Cited

OTHER PUBLICATIONS

Brown et al. "Method for Segmenting Chest CT Image Data Using An Anatomical Model: Preliminaiy Results", IEEE Transactions on Medical Imaging, 16(6): 828-839, Dec. 1997.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Charland et al. "The Use of Deconvolution and Total Least Squares in Recovering a Radiation Detector Line Spread Function", Medical Physics, 25(2): 152-160, Feb. 1998. Abstract Only!
Chengazi et al. "Imaging Prostate Cancer With Technetium-99m-7E11-05.3 (CYT-351)", Journal of Nuclear Medicine, 38: 675-682, 1997.
Corstens et al. "Nuclear Medicine's Role in Infection and Inflammation", The Lancet, 354: 765-770, 1999.
Day at al. "Localization of Radioiodinated Rat Fibrogen in Transplanted Rat Tumors", Journal of the National Cancer Institute, 23(4): 799-812, 1959.
DeGrado et al. "Topics in Integrated Systems Physiology. Tracer Kinetic Modeling in Nuclear Cardiology", Journal of Nuclear Cardiology, 7: 686-700, 2000.
Del Guerra et al. "An Integrated PET-SPECT Small Animal Imager: Preliminary Results", Nuclear Science Symposium, IEEE Records, 1: 541-544, 1999.
Dewaraja et al. "Accurate Dosimetry in [131]I Radionuclide Therapy Using Patient-Specific, 3-Dimensional Methods for SPECT Reconstruction and Basorbed Dose Calculation", The Journal of Nuclear Medicine, 46(5): 840-849, May 2005.
Di Bella et al. "Automated Region Selection for Analysis of Dynamic Cardiac SPECT Data", IEEE Transactions on Nuclear Science, XP011087693, 44(3): 1355-1361, Jun. 1997. Section II, B), Blood and Liver Correlations, Section III, Results, Figs.4, 5.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Ellestad "Stress Testing: Principles and Practice", XP008143015, 5th Edition, p. 432, Jan. 1, 2003.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "Long Focal Length, Asymmetnc Fan Beam Collimation for Transmission Acquisition With A Triple Camera SPECT System", IEEE Transactions on Nuclear Science, XP011087666, 44(3): 1191-1196, Jun. 1, 1997.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1.21-25, Jan.-Feb. 1972).
Hassan et al. "A Radiotelemetry Pill for the Measurement of Ionising Radiation Using a Mercuric Iodide Detector", Physics in Medicine and Biology, 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Herrmann et al. "Mitochondrial Proteome: Altered Cytochtrome C Oxidase Subunit Levels in Prostate Cancer", Proteomics, XP002625778, 3(9): 1801-1810, Sep. 2003.

Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jan et al. "Preliminary Results From the AROPET", IEEE Nuclear Science Symposium Conference Record, Nov. 4-10, 2001, 3: 1607-1610, 2001.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Arnual Meeting, Chicago, Illinois, 2000.
Jessup "Tumor Markers—Prognostic and Therapeutic Implications for Colorectal Carcinoma", Surgical Oncology, 7: 139-151, 1998.
Kadrmas et al. "Static Versus Dynamic Teboroxime Myocardial Perfusion SPECT in Canines", IEEE Transactions on Nuclear Science, 47(3): 1112-1117, Jun. 2000.
Kinahan et al. "Attenuation Correction for A Combined 3D PET/CT Scanner", Medical Physics, 25(10): 2046-2053, Oct. 1998.
Kojima et al. "Quantitative Planar Imaging Method for Measurement of Renal Activity by Using A Conjugate-Emission Image and Transmission Data", Medical Physics, 27(3): 608-615, 2000. p. 608.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.
Lange et al. "EM Reconstruction Algorithms for Emission and Transmission Tomography", Journal of Computer Assisted Tomography, 8(2): 306-316, Apr. 1984.
Lavallee et al. "Building A Hybrid Patient's Model for Augmented Reality in Surgery: A Registration Problem", Computing in Biological Medicine, 25(2): 149-164, 1995.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First col. 2nd §.
Lin et al. "Improved Sensor Pills for Physiological Monitoring", NASA Technical Brief, JPL New Technology Report, NPO-20652, 25(2), 2000.
Links "Advances in SPECT and PET Imaging", Annals in Nuclear Medical Science, 13(2): 107-120, Jun. 2000.
Mao et al. "Human Prostatic Carcinoma: An Electron Microscope Study", Cancer Research, XP002625777, 26(5): 955-973, May 1966.
McJilton et al. "Protein Kinase C[Epsilon] Interacts With Bax and Promotes Survival of Human Prostate Cancer Cells", Oncogene, 22; 7 958-7968, 2003.
Mettler et al. "Legal Requirements and Radiation Safety", Essentials of Nuclear Medicine Imaging, 2nd Ed., Chap. 13: 323-331, 1985.
Meyers et al. "Age, Perfusion Test Results and Dipyridamole Reaction", Radiologic Technology, XP008142909, 73(5): 409-414, May 1, 2002.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Mori et al. "Overexpression of Matrix Metalloproteinase-7mRNA in Human Colon Carcinomas", Cancer, 75: 1516-1519, 1995.
Ogawa et al. "Ultra High Resoultion Pinhole SPECT", IEEE Nuclear Science Symposium, 2: 1600-1604, 1998.

(56) References Cited

OTHER PUBLICATIONS

Ohno et al. "Selection of Optimum Projection Angles in Three Dimensional Myocardial SPECT", IEEE Nuclear Science Symposium Conference Record 2001, 4: 2166-2169, 2001.
Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Patton et al. "D-SPECT: A New Solid State Camera for High Speed Molecular Imaging", The Journal of Nuclear Medicine, 47(Suppl. 1): 189P, 2006.
Pellegrini et al. "Design of Compact Pinhole SPECT System Based on Flat Panel PMT", IEEE Nuclear Science Symposium Conference Record, 3: 1828-1832, 2003.
Pharmalucence "Kit for the Preparation of Technetium Tc99m Sulfur Colloid Injection for Subcutaneous, Intraperitoneal, Intravenous, and Oral Use", Pharrnalucence Inc, Reference ID: 2977567, Prescribing Information, 10 P., Jul. 2011.
Piperno et al. "Breast Cancer Screening by Impedance Measurements", Frontiers Med. Biol. Engng., 2(2): 11-17, 1990.
Pluim et al. "Image Registration by Maximization of Combined Mutual Information and Gradient Information", IEEE Transactions on Medical Imaging, 19(8): 1-6, 2000.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedence Monitoring During CT-Guided Stereotactic Surgery: Relative Value in Cystic and Solid Lesions", British Journal of Neurosurgery, 6: 439-444, 1992.
Rockmore et al. "A Maximum Likelihood Approach to Emission Image Reconstruction From Projections", IEEE Transactions on Nuclear Science, 23(4): 1428-1432, Aug. 1976.
Saltz et al. "Interim Report of Randomized Phase II Trial of Cetuximab/Bevacizumab/Irinotecan (CB1) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Sands et al. "Methods for the Study of the Metabolism of Radiolabeled Monoclonal Antibodies by Liver and Tumor", The Journal of Nuclear Medicine, 28: 390-398, 1987.
Seret et al. "Intrinsic Uniformity Requirements for Pinhole SPECT", Journal of Nuclear Medicine Technology, 34(1): 43-47, Mar. 2006.
Sharir et al. "D-SPECT: High Speed Myocardial Perfusion Imaging: A Comparison With Dual Detector Anger Camera (A-SPECT)", The Journal of Nuclear Medicine, 48(Suppl.2): 51P, # 169, 2007.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Smither "High Resolution Medical Imaging System for 3-D Imaging of Radioactive Sources With 1 mmFWHM Spatial Resolution", Proceedings of the SPIE, Medical Imaging 2003: Physics ofMedical Imaging, 5030: 1052-1060, Jun. 9, 2003.
Solanki "The Use of Automation in Radiopharmacy", Hospital Pharmacist, 7(4): 94-98, Apr. 2000.
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.

Storey et al. "Tc-99m Sestamibi Uptake in Metastatic Prostate Carcinoma", Clinical Nuclear Medicine, XP009145398, 25(2): 133-134, Feb. 2000.
Studen "Compton Camera With Position-Sensitive Silicon Detectors", Doctoral Thesis, University of Ljubljana, Faculty of Mathematics and Physics, 36 P., 2005.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Wong et al. "Segmentation of Dynamic PET Images Using Cluster Analysis", IEEE Transactions on Nuclear Science, XP002347001, 49(1): 200-207, Feb. 2002. Introduction, Section I, Last Para, Section II, A, Segmentation Scheme, Section II, C, Validation Study, Figs.2, 5.
Wu et al. "ECG-Gated Pinhole SPECT in Mice With Millimeter Spatial Resolution", IEEE Transactions on Nuclear Science, 47(3): 1218-1221, Jun. 2000.
Xu et al. "Quantitative Expression Profile of Androgen-Regulated Genes in Prostate Cancer Cells and Identification of Prostate-Specific Genes", International Journal of Cancer, 92: 322-328, 2001.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magnetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Zhang et al. "An Innovative High Efficiency and High Resolution Probe for Prostate Imaging", The Journal of Nuclear Medicine, 68: 18, 2000. Abstract.
Zhang et al. "Potential of a Compton Camera Scintimammography", Physics in Medicine for High Performance and Biology, XP020024019, 49(4): 617-638, Feb. 21, 2004.
Restriction Official Action dated Oct. 20, 2016 From the US Patent and Trademark Office Re. U.S. Appl. No. 14/100,082.
Notice of Allowance dated Jul. 19, 2018 From the US Patent and Trademark Office Re. U.S. Appl. No. 15/953,461. (312 pages).
Communication Pursuant to Article 94(3) EPC dated Mar. 8, 2010 From the European Patent Office Re. Application No. 06832278.3.
Communication Pursuant to Article 94(3) EPC dated Sep. 12, 2014 From the European Patent Office Re. Application No. 06832278.3.
Communication Pursuant to Article 94(3) EPC dated Sep. 16, 2013 From the European Patent Office Re.: Application No. 06832278.3.
Communication Pursuant to Article 94(3) EPC dated Sep. 17, 2012 From the European Patent Office Re. Application No. 06832278.3.
Communication Pursuant to Article 94(3) EPC dated Sep. 23, 2011 From the European Patent Office Re.: Application No. 06832278.3.
International Preliminary Report on Patentability dated Jan. 22, 2009 From the International Bureau of WIPO Re.: Application No. PCT/IL2006/001511.

(56) References Cited

OTHER PUBLICATIONS

International Search Report dated Jul. 11, 2008 From the International Searching Authority of the Patent Cooperation Treaty Re.: Application No. PCT/IL06/01511.
Invitation to Pay Additional Fees dated Jul. 10, 2008 From the International Searching Authority Re.: Application No. PCT/IL06/01511.
Official Action dated Aug. 2, 2012 From the US Patent and Trademark Office Re. U.S. Appl. No. 12/087,150.
Official Action dated Dec. 4, 2014 From the US Patent and Trademark Office Re. U.S. Appl. No. 12/087,150.
Official Action dated Jun. 12, 2013 From the US Patent and Trademark Office Re. U.S. Appl. No. 12/087,150.
Official Action dated Sep. 12, 2011 From the US Patent and Trademark Office Re. U.S. Appl. No. 12/087,150.
Official Action dated Dec. 16, 2013 From the US Patent and Trademark Office Re. U.S. Appl. No. 12/087,150.
Official Action dated Jun. 2014 From the US Patent and Trademark Office Re. U.S. Appl. No. 12/087,150.
Official Action dated Jan. 23, 2012 From the US Patent and Trademark Office Re. U.S. Appl. No. 12/087,150.
Supplementary Partial European Search Report and the European Search Opinion dated Dec. 15, 2009 From the European Patent Office Re.: Application No. 06832278.3.
Written Opinion dated Jul. 11, 2008 from the International Searching Authority of the Patent Cooperation Treaty Re.: Application No. PCT/IL06/01511.
Bacharach et al. "Attenuation Correction in Cardiac Positron Emission Tomography and Single-Photon Emission Computed Tomography", Journal of Nucelar Cardiology, 2(3): 246-255, 1995.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™ Product Sheet, 5 P., Jun. 1995.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Handrick et al. "Evaluation of Binning Strategies for Tissue Classification in Computed Tomography Images", Medical Imaging 2006: Image Processing, Proceedings of the SPIE, 6144: 1476-1486, 2006.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Johnson et al. "Analysis and Reconstruction of Medical Images Using Prior Information", Lectures Notes in Statistics, Case Studies in Bayesian Statistics, II: 149-228, 1995.
Li et al. "A HOTLink/Networked PC Data Acquisition and Image Reconstruction System for a High Resolution Whole-Body PET With Respiratory or ECG-Gated Performance", IEEE Nuclear Science Symposium and Medical Imaging Conference, Norfolk, VA, USA, Nov. 10-16, 2002, XP010663724, 2: 1135-1139, Nov. 10, 2002. p. 1137, First col. 2nd §.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Ouyang et al. "Incorporation of Correlated Structural Images in PET Image Reconstruction", IEEE Transactions of Medical Imaging, 13(4): 627-640, Dec. 1994.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Thorndyke et al. "Reducing Respiratory Motion Artifacts in Positron Emission Tomography Through Retrospective Stacking", Medical Physics, 33(7): 2632-2641, Jul. 2006.
Uni Magdeburg "Attenuation Map", University of Magdeburg, Germany, Retrieved From the Internet, Archived on Jul. 31, 2002.
Toennies et al. "Scatter Segmentation in Dynamic SPECT Images Using Principal Component Analysis", Progress in Biomedical Optics and Imaging, 4(23): 507-516, 2003.
Zaidi et al. "Determination of the Attenuation Map in Emission Tomography", Journal of Nuclear Medicine, 44(2): 291-315, 2003.

\* cited by examiner

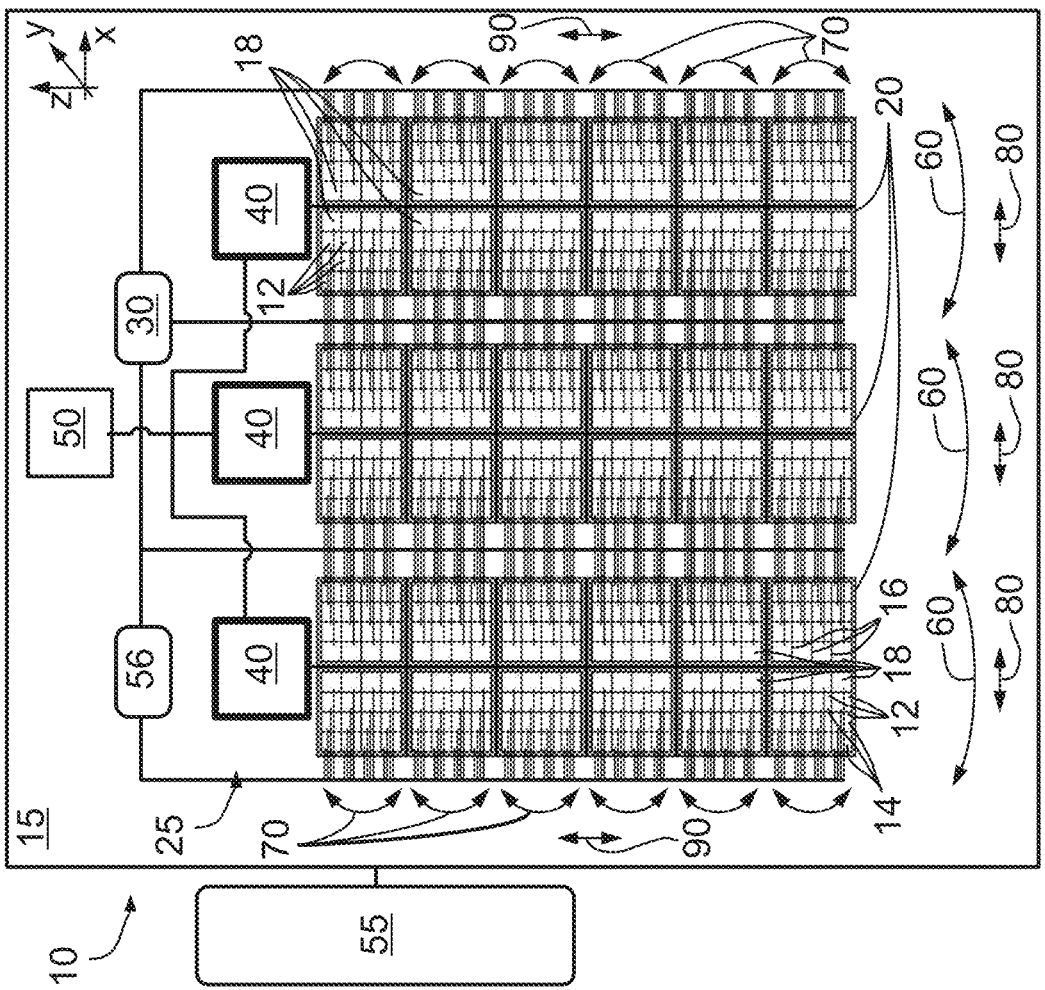
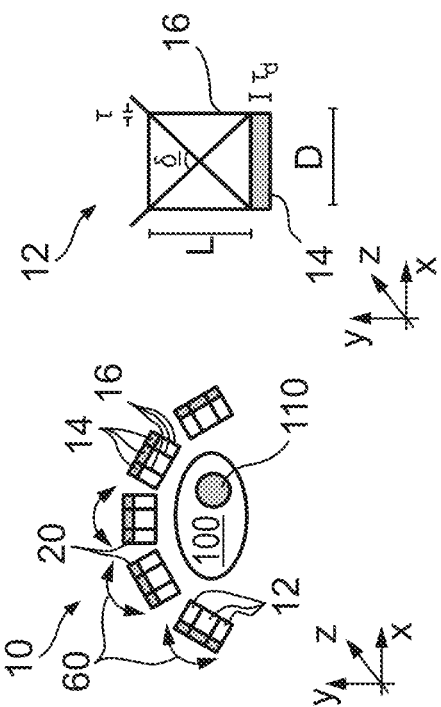
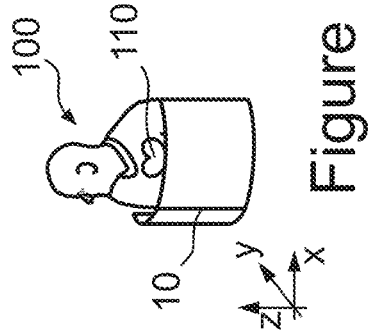
Figure 1A  Figure 1B  Figure 1C  Figure 1D

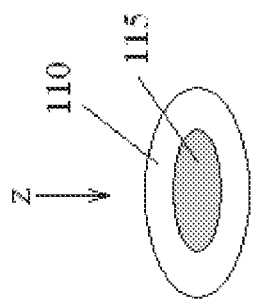
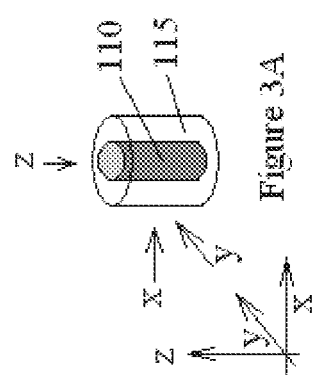
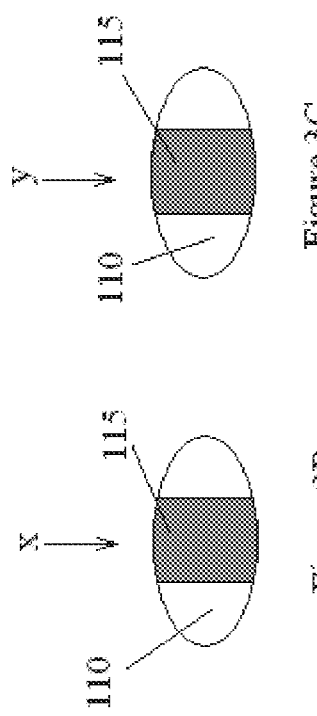

Figure 4C
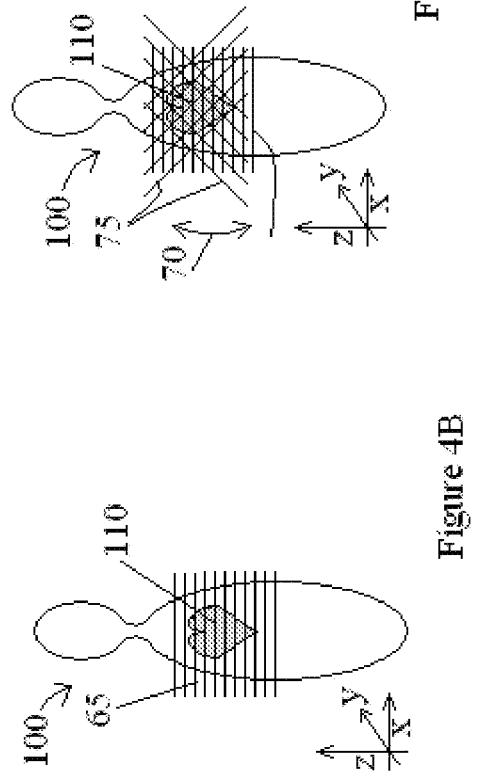
Figure 4B
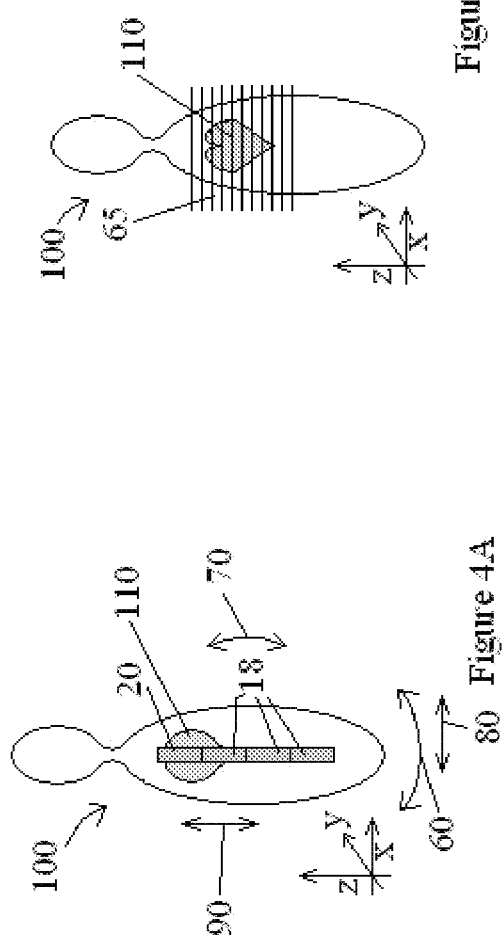
Figure 4A
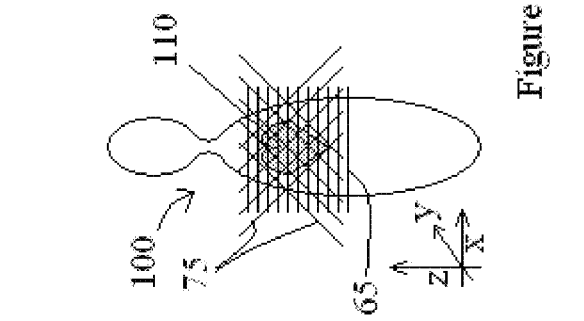
Figure 4F
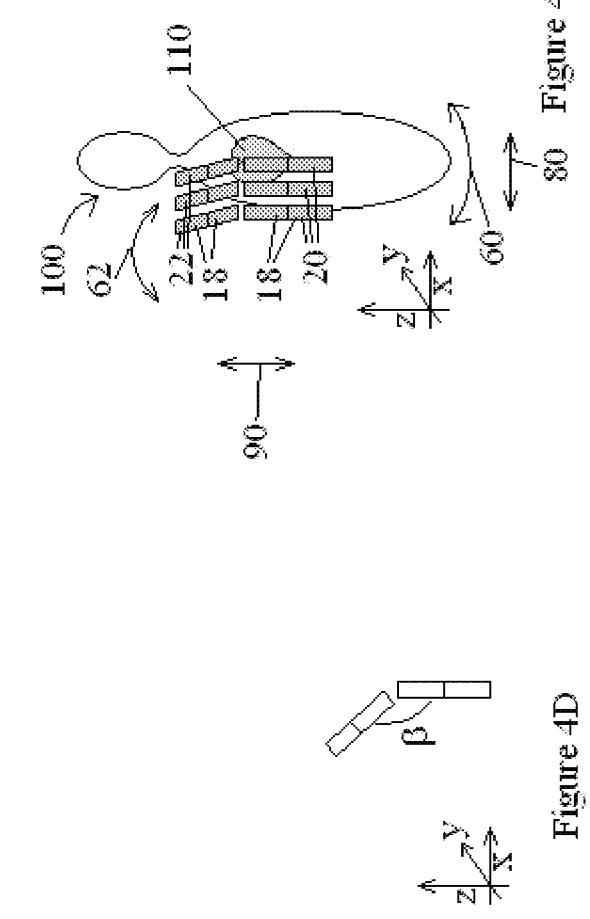
Figure 4E
Figure 4D

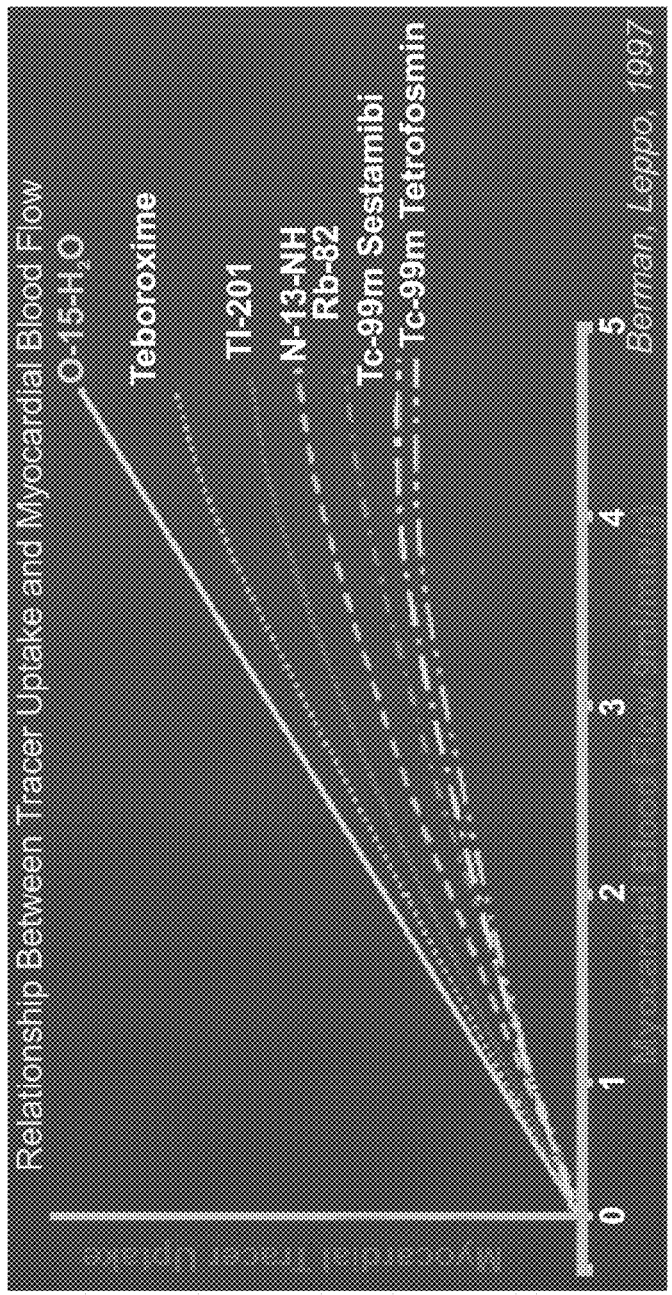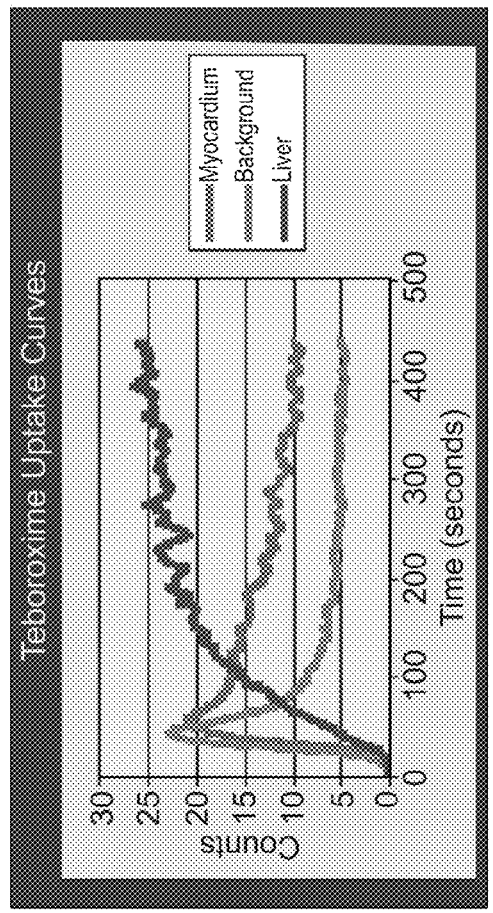
Figure 5A
Figure 5B

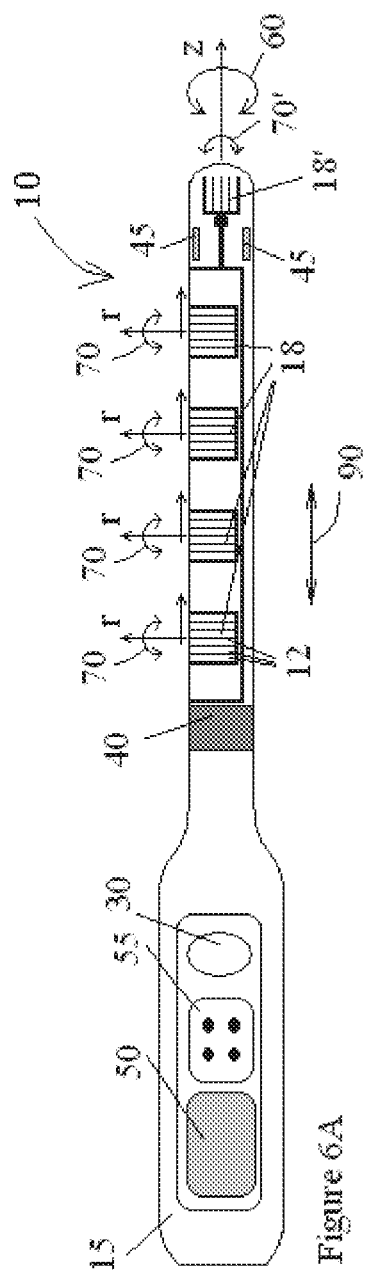
Figure 6A
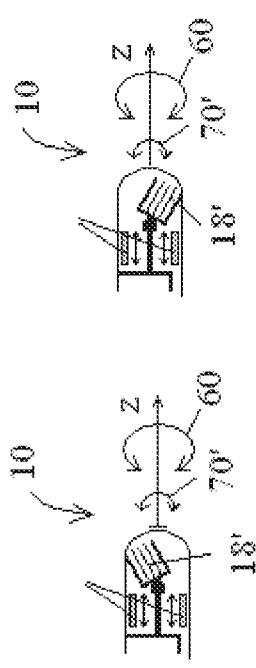
Figure 6B
Figure 6C
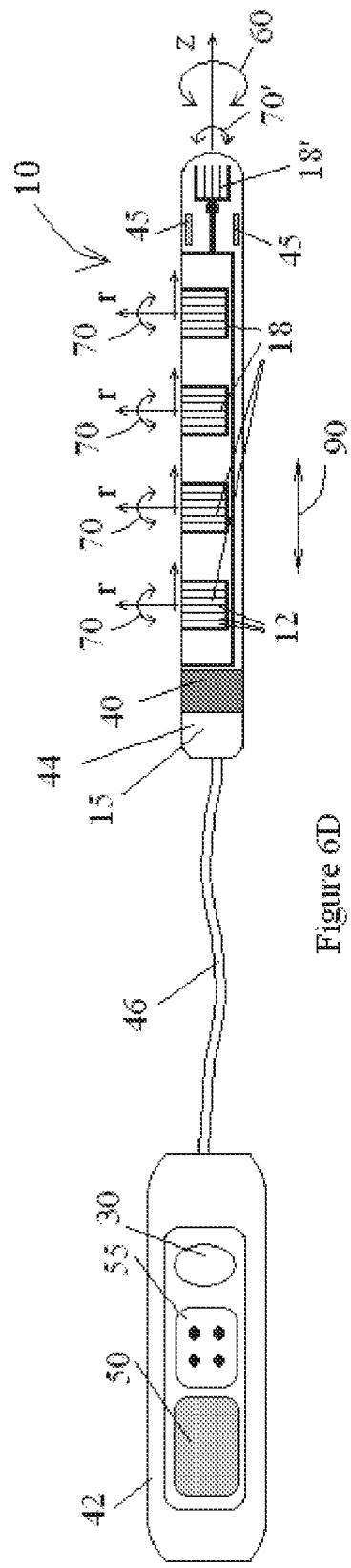
Figure 6D

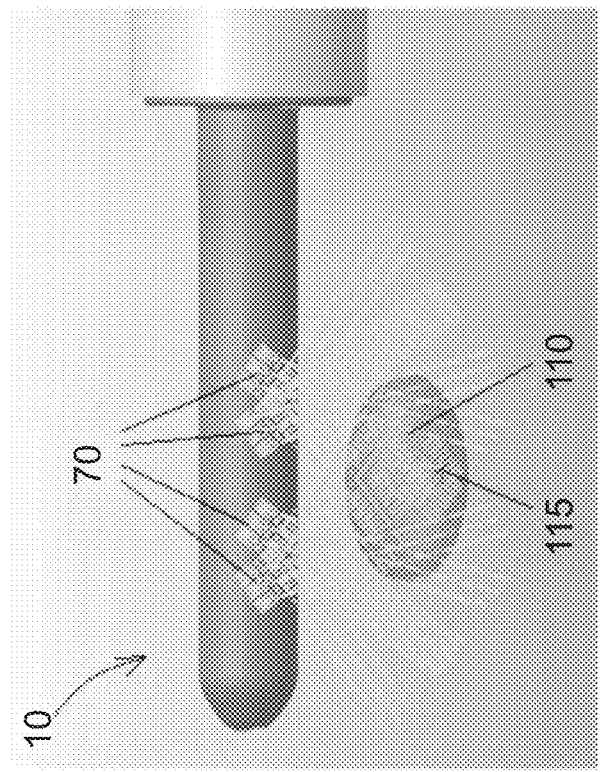
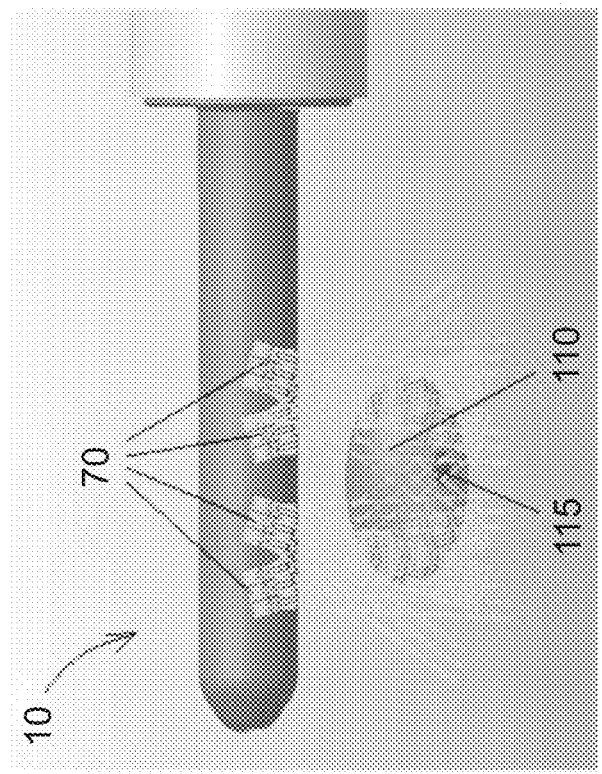
Figure 6F
Figure 6E

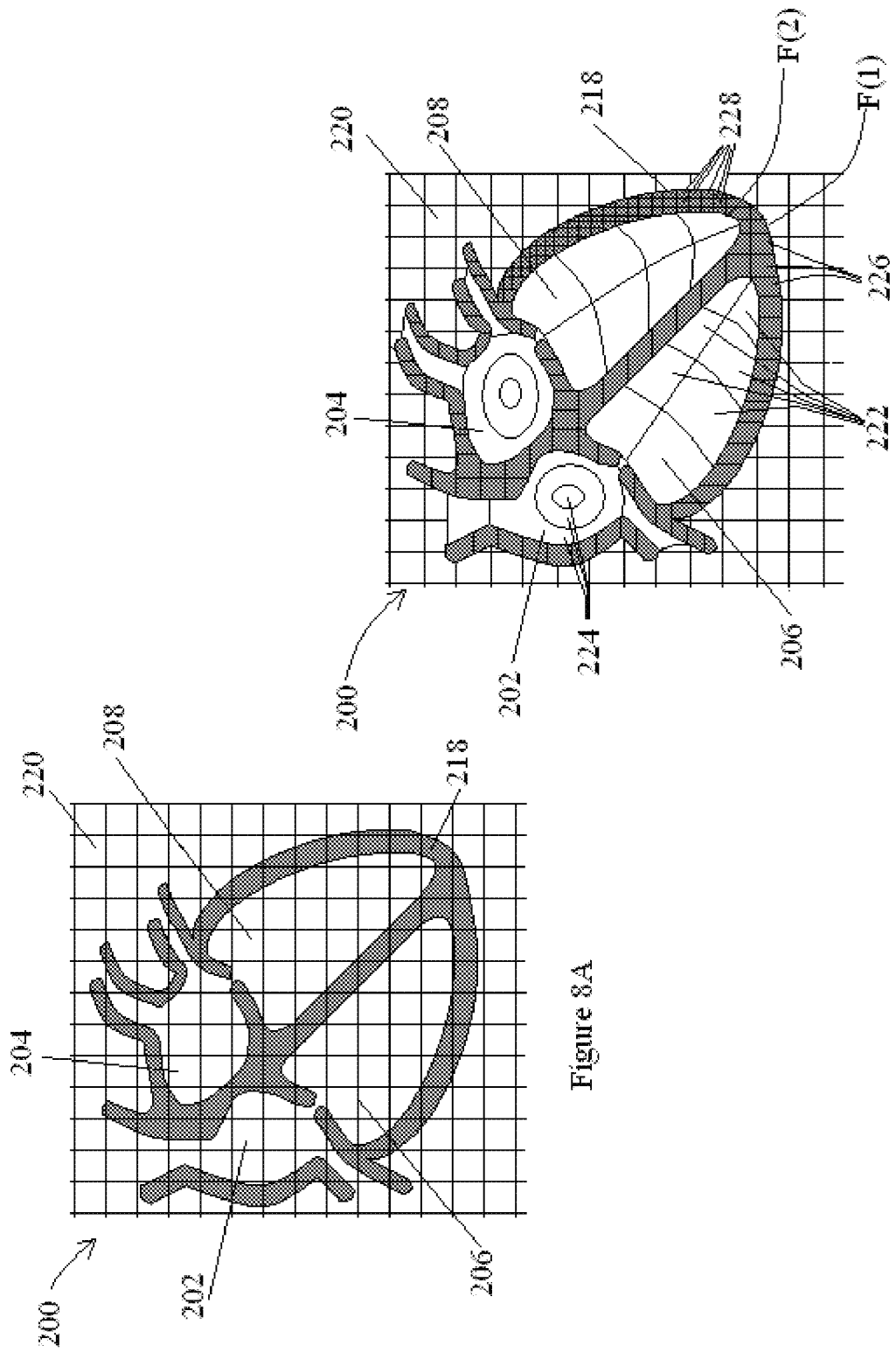

Anatomical Landmarks

- Left Ventricle (LV)
- Right Ventricle (RV)
- Left Atrium (LA)
- Right Atrium (RA)

- First 4 minutes after Tc99m-Teboroxime* injection, 10s/frame
- Mid-ventricular slices (upper row : SA lower row: HLA)
- Note as the intense blood pool activity at the center of the heart chambers gradually clears, while the myocardial uptake gradually intensifies "Movie" representation of a dynamic SPECT study (SA)

- First 4 minutes after Tc99m-Teboroxime* injection, 10s/frame
- Mid-ventricular SA slices.
- Note as the intense blood pool activity gradually clears in LV and RV cavities
- Myocardial uptake gradually intensifies, (the thin walled RV is less intense)

"Movie" representation of a dynamic SPECT study (SA)

- First 4 minutes after Tc99m-Teboroxime* injection, 10s/frame
- Mid-ventricular SA slices.
- Note as the intense blood pool activity gradually clears in LV, RV, LA and RA cavities
- Myocardial uptake gradually intensifies, (the thin walled RV ant atria are less intense)

Figure 10

| Time (sec) | No. of events | Average rate (MHz) |
|---|---|---|
| 0.001 | 56 | 0.056 |
| 0.002 | 369 | |
| 0.003 | 379 | 0.379 |
| 0.004 | 378 | 0.378 |
| 0.005 | 382 | 0.382 |
| 0.006 | 376 | 0.376 |
| 0.007 | 366 | 0.366 |
| 0.008 | 372 | 0.372 |
| 0.009 | 374 | 0.374 |
| 0.010 | 372 | 0.372 |
| 0.011 | 370 | 0.370 |
| 0.012 | 371 | 0.371 |
| 0.013 | 364 | 0.364 |
| 0.014 | 372 | 0.372 |
| 0.015 | 374 | 0.374 |
| 0.016 | 372 | 0.372 |
| 0.017 | 364 | 0.364 |
| 0.018 | 368 | 0.368 |
| 0.019 | 364 | 0.364 |
| 0.020 | 373 | 0.373 |
| 0.021 | 362 | 0.362 |
| 0.022 | 374 | 0.374 |
| 0.023 | 372 | 0.372 |
| 0.024 | 377 | 0.377 |
| 0.025 | 367 | 0.367 |
| 0.026 | 377 | 0.377 |
| 0.027 | 373 | 0.373 |
| 0.028 | 363 | 0.363 |
| 0.029 | 373 | 0.373 |

GATING WITH ANATOMICALLY VARYING DURATIONS

RELATED APPLICATIONS

This application is a Continuation of U.S. patent application Ser. No. 12/087,150, filed on Dec. 22, 2008 which is a National Phase of PCT Patent Application No. PCT/IL2006/001511 having International Filing Date of Dec. 28, 2006, which claims the benefit of U.S. Provisional Patent Application No. 60/816,970 filed on Jun. 28, 2006, 60/800,846 filed on May 17, 2006, 60/800,845 filed on May 17, 2006, 60/799,688 filed on May 11, 2006, 60/763,458 filed on Jan. 31, 2006, 60/754,199 filed on Dec. 28, 2005.

U.S. patent application Ser. No. 12/087,150 is also a Continuation of U.S. patent application Ser. No. 11/607,075 filed on Dec. 1, 2006 now U.S. Pat. No. 8,094,894.

U.S. patent application Ser. No. 12/087,150 is also a Continuation of PCT Patent Application No. PCT/IL2006/001291 having International Filing Date of Nov. 9, 2006, which also claims the benefit of U.S. Provisional Patent Application No. 60/800,846 filed on May 17, 2006, 60/800,845 filed on May 17, 2006, 60/799,688 filed on May 11, 2006 and 60/754,199 filed on Dec. 28, 2005.

U.S. patent application Ser. No. 12/087,150 is also a Continuation of PCT Patent Application No. PCT/IL2006/000834 having International Filing Date of Jul. 19, 2006, which also claims benefit of U.S. Provisional Patent Application No. 60/816,970 filed on Jun. 28, 2006, 60/800,846 filed on May 17, 2006, 60/800,845 filed on May 17, 2006, 60/799,688 filed on May 11, 2006 and 60/763,458 filed on Jan. 31, 2006.

U.S. patent application Ser. No. 12/087,150 is also a Continuation of PCT Patent Application No. PCT/IL2006/000840 having International Filing Date of Jul. 19, 2006, which also claims benefit of U.S. Provisional Patent Application No. 60/816,970 filed on Jun. 28, 2006, 60/800,846 filed on May 17, 2006, 60/800,845 filed on May 17, 2006, 60/799,688 filed on May 11, 2006 and 60/763,458 filed on Jan. 31, 2006.

U.S. patent application Ser. No. 12/087,150 is also a Continuation of PCT Patent Application No. PCT/IL2006/000562 having International Filing Date of May 11, 2006, which also claims the benefit of U.S. Provisional Patent Applications No. 60/763,458 filed on Jan. 31, 2006.

U.S. patent application Ser. No. 12/087,150 is also a Continuation of PCT Patent Application No. PCT/IL2006/000059 having International Filing Date of Jan. 15, 2006.

U.S. patent application Ser. No. 12/087,150 is also a Continuation of U.S. patent application Ser. No. 12/084,559 filed on Nov. 26, 2008, now U.S. Pat. No. 7,705,316 which is a National Phase of PCT Patent Application No. PCT/IL2006/001291 having International Filing Date on Nov. 9, 2006, which is a Continuation-in-Part (CIP) of PCT Patent Application Nos. PCT/IL2006/000840 and PCT/IL2006/000834, both having International Filing Date on Jul. 19, 2006, PCT/IL2006/000562 having International Filing Date on May 11, 2006, PCT/IL2006/000059 having International Filing Date on Jan. 15, 2006, PCT/IL2005/001215 having International Filing Date on Nov. 16, 2005 and PCT/IL2005/001173 having International Filing Date on Nov. 9, 2005.

PCT Patent Application No. PCT/IL2006/001291 also claims the benefit of priority of U.S. Provisional Patent Application No. 60/816,970 filed on Jun. 28, 2006, 60/800,846 and 60/800,845, both filed on May 17, 2006, 60/799,688 filed on May 11, 2006, 60/763,458 filed on Jan. 31, 2006, 60/754,199 filed on Dec. 28, 2005, 60/750,597 and 60/750,334, both filed on Dec. 15, 2005, 60/750,287 filed on Dec. 13, 2005 and 60/741,440 filed on Dec. 2, 2005.

PCT Patent Application No. PCT/IL2006/001291 also claims the benefit of priority of Israel Patent Application No. 172349, filed on Nov. 27, 2005.

PCT Patent Application No. PCT/IL2005/001173 is a Continuation-in-Part (CIP) of PCT Patent Application Nos. PCT/IL2005/000575 and PCT/IL2005/000572, both having International Filing Date on Jun. 1, 2005, and PCT/IL2005/000048 having International Filing Date on Jan. 13, 2005.

PCT Patent Application No. PCT/IL2005/001173 also claims the benefit of priority of U.S. Provisional Patent Application Nos. 60/720,652 and 60/720,541, both filed on Sep. 27, 2005, 60/720,034 filed on Sep. 26, 2005, 60/702,979 filed on Jul. 28, 2005, 60/700,753 and 60/700,752, both filed on Jul. 20, 2005, 60/700,318, 60/700,317, and 60/700,299 all filed on Jul. 19, 2005, 60/691,780 filed on Jun. 20, 2005, 60/675,892 filed on Apr. 29, 2005, 60/648,690 filed on Feb. 2, 2005, 60/648,385 filed on Feb. 1, 2005, 60/640,215 filed on Jan. 3, 2005, 60/636,088 filed on Dec. 16, 2004, 60/635,630 filed on Dec. 14, 2004, 60/632,515 filed on Dec. 3, 2004, 60/632,236 filed on Dec. 2, 2004, 60/630,561 filed on Nov. 26, 2004, 60/628,105 filed on Nov. 17, 2004 and 60/625,971 filed on Nov. 9, 2004.

PCT Patent Application No. PCT/IL2005/001173 also claims the benefit of priority of Israel Patent Application No. 171346 filed on Oct. 10, 2005.

PCT Patent Application No. PCT/IL2005/000575 claims the benefit of priority of U.S. Provisional Patent No. 60/575,369 filed on Jun. 1, 2004.

U.S. patent application Ser. No. 12/084,559 is also a Continuation-in-Part (CIP) of U.S. patent application Ser. No. 11/034,007 filed on Jan. 13, 2005, now U.S. Pat. No. 7,176,466, which claims the benefit of priority of U.S. Provisional Patent Application No. 60/535,830 filed on Jan. 13, 2004.

The contents of the above applications are all incorporated herein by reference.

FIELD AND BACKGROUND OF THE INVENTION

The present invention relates to a method and an apparatus for image reconstruction in nuclear medicine imaging and, more particularly, but not exclusively to image reconstruction in nuclear medicine imaging using gating techniques.

Radionuclide imaging aims at obtaining an image of a radioactively labeled substance, that is, a radiopharmaceutical, within the body, following administration, generally, by injection. The substance is chosen so as to be picked up by active pathologies to a different extent from the amount picked up by the surrounding, healthy tissue in consequence; the pathologies are operative as radioactive-emission sources and may be detected by radioactive-emission imaging. Pathology may appear as a concentrated source of high radiation, that is, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

The mechanism of localization of a radiopharmaceutical in a particular organ of interest depends on various processes in the organ of interest such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is found in http://www(dot)lunis(dot)luc(dot)edu/nucmed/tutorial/radpharm/i(dot)htm.

The particular choice of a radionuclide for labeling antibodies depends upon the chemistry of the labeling procedure and the isotope nuclear properties, such as the number of gamma rays emitted, their respective energies, the emission of other particles such as beta or positrons, the isotope half-life, and the decay scheme.

In PET imaging, positron-emitting radioisotopes are used for labeling, and the imaging camera detects coincidence photons, the gamma pair of 0.511 Mev, traveling in opposite directions. Each one of the coincident detections defines a line of sight, along which annihilation takes place. As such, PET imaging collects emission events, which occurred in an imaginary tubular section enclosed by the PET detectors. A gold standard for PET imaging is PET $NH_3$ rest myocardial perfusion imaging with N-13-ammonia ($NH_3$), at a dose level of 740 MBq, with attenuation correction. Yet, since the annihilation gamma is of 0.511 Mev, regardless of the radioisotope, PET imaging does not provide spectral information, and does not differentiate between radioisotopes.

In SPECT imaging, primarily gamma emitting radioisotopes are used for labeling, and the imaging camera is designed to detect the actual gamma emission, generally, in an energy range of approximately 11-511 KeV. Generally, each detecting unit, which represents a single image pixel, has a collimator that defines the solid angle from which radioactive emission events may be detected.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. Therefore, the gold standard for spatial and time resolutions in nuclear imaging is defined for PET. For example, there is a gold standard for PET imaging for at rest myocardial perfusion with N-13-ammonia ($NH_3$), at a dose of 740 MBq with attenuation correction."

Conventional SPECT cameras generally employ an Anger camera, in which a single-pixel scintillation detector, such as NaI(Tl), LSO, GSO, CsI, CaF, or the like, is associated with a plurality of photomultipliers. Dedicated algorithms provide a two dimensional image of the scintillations in the single pixel scintillation detector. There are several disadvantages to this system, for example:
1. The dedicated algorithms associated with the single pixel cannot reach the accuracy of a two-dimensional image of a plurality of single pixel detectors;
2. The single-pixel detector is a rigid unit, which does not have the flexibility of motion of a plurality of small detectors, each with independent motion; and
3. A single hot spot may cause the single pixel detector of the Anger camera to saturate, whereas when a plurality of single pixel detectors is employed, saturation is localized to a few pixels and does not affect the whole image.

Other SPECT cameras which employ a plurality of single pixel detectors are also known.

U.S. Pat. No. 6,628,984, to Weinberg, issued on Sep. 30, 2003 and entitled, "Handheld camera with tomographic capability," describes a tomographic imaging system, which includes a moveable detector or detectors capable of detecting gamma radiation; one or more position sensors for determining the position and angulation of the detector(s) in relation to a gamma ray emitting source; and a computational device for integrating the position and angulation of the detector(s) with information as to the energy and distribution of gamma rays detected by the detector and deriving a three dimensional representation of the source based on the integration. A method of imaging a radiation emitting lesion located in a volumetric region of interest also is disclosed.

U.S. Pat. No. 6,242,743, to DeVito, et al., issued on Jun. 5, 2001 and entitled, "Non-orbiting tomographic imaging system," describes a tomographic imaging system which images ionizing radiation such as gamma rays or x rays and which: 1) can produce tomographic images without requiring an orbiting motion of the detector(s) or collimator(s) around the object of interest, 2) produces smaller tomographic systems with enhanced system mobility, and 3) is capable of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible, and several combinations of such geometry and motion are shown. The geometric configurations may be fixed or variable during the acquisition or between acquisition intervals. Clinical applications of various embodiments of U.S. Pat. No. 6,242,743 include imaging of the human heart, breast, brain or limbs, or small animals. Methods of using the non-orbiting tomographic imaging system are also included.

U.S. Pat. No. 5,939,724, to Eisen, et al., issued on Aug. 17, 1999, and entitled, "Light weight-camera head and—camera assemblies containing it," describes a lightweight gamma-camera head, assemblies, and kits that embody it. The gamma-camera head has a detector assembly which includes an array of room temperature, solid state spectroscopy grade detectors each associated with a collimator and preamplifier, which detectors and associated collimators and preamplifiers are arranged in parallel rows extending in a first direction and suitably spaced from each other in a second direction normal to the first direction, each of the parallel detector rows holding a plurality of detectors. The head may optionally have an electric motor for moving the detector in the second direction and optionally also in the first direction, either stepwise or continuously.

U.S. Pat. No. 6,525,320, to Juni, issued on Feb. 25, 2003, and entitled, single photon emission computed tomography system, describes a single photon emission computed tomography system, which produces multiple tomographic images of the type representing a three-dimensional distribution of a photon-emitting radioisotope. The system has a base including a patient support for supporting a patient such that a portion of the patient is located in a field of view. A longitudinal axis is defined through the field of view. A detector module is adjacent the field of view and includes a photon-responsive detector. The detector is an elongated strip with a central axis that is generally parallel to the longitudinal axis. The detector is operable to detect if a photon strikes the detector. The detector can also determine a position along the length of the strip where a photon is detected. A photon-blocking member is positioned between the field of view and the detector. The blocking member has an aperture slot for passage of photons aligned with the aperture slot. The slot is generally parallel to the longitudinal axis. A line of response is defined from the detector through the aperture. A displacement device moves either the detector module or the photon-blocking member relative to the other so that the aperture is displaced relative to the detector and the line of response is swept across at least a portion of the field of view.

U.S. Pat. No. 6,271,525, to Majewski, et al., issued on Aug. 7, 2001, and entitled, "Mini gamma camera, camera system and method of use," describes a gamma camera, which comprises essentially and in order from the front outer or gamma ray impinging surface: 1) a collimator, 2) a scintillator layer, 3) a light guide, 4) an array of position sensitive, high resolution photomultiplier tubes, and 5) printed circuitry for receipt of the output of the photomultipliers. There is also described, a system wherein the output supplied by the high resolution, position sensitive photomultipiler tubes is communicated to: a) a digitizer and b) a computer where it is processed using advanced image processing techniques and a specific algorithm to calculate the center of gravity of any abnormality observed during imaging, and c) optional image display and telecommunications ports.

U.S. Pat. No. 6,271,524, to Wainer, et al., issued on Aug. 7, 2001 and entitled, "Gamma ray collimator," describes a gamma ray collimator assembly comprising collimators of different gamma ray acceptance angles. For example, the acceptance angle of a first collimator may be between 0.2 and 5 degrees, and the acceptance angle of a second collimator may be between about 5 and 30 degrees.

U.S. Pat. No. 6,212,423, to Krakovitz, issued on Apr. 3, 2001 and entitled, "Diagnostic hybrid probes," describes a hybrid nuclear and ultrasonic probe, comprising a cylindrical outer casing surrounding a nuclear probe, which comprises two scintillator plates intersecting perpendicularly, each of the scintillator plates having a plurality of parallel collimators; and an ultrasonic probe situated between said casing at the intersection of said scintillator plates.

List mode data acquisition is known in PET studies, and enables the determination of coincidence. It relates to recording every radiation event together with data pertinent to that event, which includes:
i. the time the radiation event impinged upon a detector pixel, with respect to a clock, with respect to a time bin, or with respect to another time definition, for example, a time interval between two clock signals; and
ii. the detector pixel location with respect to a coordinate system, at the time of the impinging.

The knowledge of time and location enables the determination of coincidence counts, namely photon counts that arrive substantially simultaneously, 180 degrees apart.

The time and location data may be stamped onto the radiation-event data packet, for example, as a header or as a footer, or otherwise associated with the radiation-event data packet, as known.

The time-stamped data available in PET studies may further be used for perfusion studies, where the timing of physiological processes of short durations, that is, durations shorter than about half the time span between heartbeats, is important. Perfusion studies usually involve a sequence of continuous acquisitions, each of which may represent data acquisition duration of about 10-30 seconds, although longer durations are sometimes employed. Data from each of the frames is independently reconstructed to form a set of images that can be visualized and used to estimate physiological parameters. This approach involves selection of the set of acquisition times, where one must choose between collecting longer scans with good counting statistics but poor temporal resolution, or shorter scans that are noisy but preserve temporal resolution.

US Patent Application 2003010539, to Tumer, et al., published on Jun. 5, 2003, and entitled, "X-ray and gamma ray detector readout system," describes a readout electronics scheme, under development for high resolution, compact PET (positron emission tomography) imagers, using time tagging, based on LSO (lutetium ortho-oxysilicate, Lu.sub.2SiO.sub.5) scintillator and avalanche photodiode (APD) arrays.

There is some work relating to timing data in SPECT systems, employing Anger cameras.

U.S. Pat. No. 5,722,405, to Goldberg, issued on Mar. 3, 1998, and entitled, "Method and apparatus for acquisition and processsing of event data in semi list mode," describes a system for acquisition, processing and display of gated SPECT imaging data for use in diagnosing Coronary Artery Disease (CAD) in nuclear medicine, employing an Anger camera, and provides a physician with two parameters for evaluating CAD: information relating to the distribution of blood flow within the myocardium (perfusion) and information relating to myocardium wall motion (function). One aspect provides the physician with a display of functional images representing quantitative information relating to both perfusion and function with respect to selected regions of interest of the subject heart at end-diastole and end-systole segments of the cardiac cycle. The functional display consists of arcs of varied width depending on wall motion and color coded to illustrate degrees of myocardial perfusion for different pie shaped sections of a selected region of interest within a given short axis slice of reconstructed volumetric region data. Another aspect provides a series of display images allowing facilitated access, display, and comparison of the numerous image frames of the heart that may be collected during gated SPECT sessions. U.S. Pat. No. 5,722,405 also teaches the ability to define and recall parameter files representative of data acquisition and processing parameters and protocol for use in gated SPECT studies and includes a semi-list processing mode to increase efficiency of data acquisition within a camera computer system.

U.S. Pat. No. 7,026,623, to Oaknin, et al., issued on Apr. 11, 2006, and entitled, "Efficient single photon emission imaging," describes a method of diagnostic imaging in a shortened acquisition time for obtaining a reconstructed diagnostic image of a portion of a body of a human patient who has been administered with dosage of radiopharmaceutical substance radiating gamma rays, using SPECT and an Anger camera. The method comprises acquiring photons emitted from said portion of the body, by means of a detector capable of converting the photons into electric signals, wherein the total time of photon acquiring is substantially shorter than the clinically acceptable acquisition time; processing said electric signals by a position logic circuitry and thereby deriving data indicative of positions on said photon detector crystal, where the photons have impinged the detector; and reconstructing an image of a spatial distribution of the pharmaceutical substance within the portion of the body by iteratively processing said data. For example, the method includes effective acquisition time of less than 10 minutes, or less than 8 minutes, and acquiring photons in a list-mode procedure.

Current techniques record data with SPECT and electrocardiogram (ECG), and perform some gating to the data which is captured by the SPECT detectors, to incorporate the global and regional atrial and ventricular function and assessment of the relationship of perfusion to regional function.

Gated images are used to overcome distortions such as motion artifacts, which are caused due to motion of the heart during image acquisition. The images are needed as the physical model used for reconstruction assumes that the imaged objects are static. In gated imaging, photon-counting takes into account the portion of the heart contraction cycle within which a photon is measured. The Gating enables the reconstruction of an anatomical structure which is subject to periodic motion by enabling image acquisition only when the structure has reached the same configuration. Cardiac contraction is usually synchronized to the recorded electrocardiogram (ECG) signal that indicates the current heart pose. The period between a certain repetitive wave, such as R-wave, and a subsequent wave is divided into several time segments, called "frames", which are usually spaced evenly. Each photon which is detected by the PET detectors during one of the frames is collected and associated with the related frame.

In gated imaging, each frame generates a single dataset. The collection of all the datasets belonging to all the frames are defined as a "dynamic" dataset.

The dynamic dataset is created by dividing the time span between one R-wave to the next R-wave into M frames that usually have an identical duration. Each detected photon is accumulated into a dataset of one of the M frames. Each dataset of the M datasets contains data relevant to a defined portion ("snapshot") within the cardiac cycle.

Usually, during the image reconstruction process, each one of the gated datasets of the M frames is processed independently by a suitable reconstruction algorithm, see Leahy R et al., Computer tomography in: Handbook of Image and Video Processing, BovikA, Academic press, 2000, pp. 771-787; J. Kay. The EM algorithm in medical imaging, Stat. Meth. Med. Res., 6(1):55-75, January 1997; J. A. Fessler, Statistical image reconstruction methods for transmission tomography, Handbook of Medical Imaging, Volumetric region 2, pages 1-70. SPIE, Bellingham, 2000; R. M. Leahy et al., Statistical approaches in quantitative positron emission tomography, 10(2):147-65, April 2000; M. Defrise, A short reader's guide to 3D tomographic reconstruction, Computerized Medical Imaging and Graphics, 25(2):1 13-6, March 2001; Vandenberghe, Y. D'Asseler, et al. Iterative reconstruction algorithms in nuclear medicine, Computerized Medical Imaging and Graphics, 25(2): 105-11, March 2001; G. L. Zeng. Image reconstruction, a tutorial, Computerized Medical Imaging and Graphics, 25(2):97-103, March 2001; and R. M. Lewitt et al., Overview of methods for image reconstruction from projections in emission computed tomography, Proc. IEEE, 91(9):1588-611, October 2003, which are incorporated herein by reference in its entirety.

A common practice in gated SPECT reconstruction is to divide the gated dynamic dataset into M 'non-gated' data sets. Each one of the datasets includes data from a single frame i. The reconstruction of each volumetric region is performed independently using the relevant data set.

In particular, once the emission data is obtained, the data is processed to reconstruct the intensity distribution within the measured volumetric region. The reconstruction process is generally complex, due to the large quantity of data that must be processed in order to obtain an accurate reconstruction. The following prior art statistical model may be used to perform reconstruction.

We assume an intensity distribution, I, defined over an input overall volume U, where U denotes a set of basic elements, such as pixels in two dimensional overall volumes and voxels in three dimensional overall volumes, and I(u) is the intensity of a given basic element u∈U. A detecting unit positioned on a radiation-emission-measuring-probe such as a PET detector or the like takes a series of measurements $y=(y_t)_{t=1}^T$ from different positions and orientations around the volumetric region U. The geometrical and physical properties of the detecting unit, together with its position and orientation in a given measurement t, determine the detection probability $\phi t(u)$ of a photon emitted from location u in time t. Thus, the effective intensity of location u as viewed by the detecting unit during measurement t is $\phi t(u)I(u)$.

The random count Xt(u) of photons that are emitted from location u and detected in measurement t is modeled by a Poisson process with mean $\phi t(u)I(u)$. The total count of photons detected in measurement t is Yt=$\Sigma u \in U$ Xt(u), and the reconstruction problem is to reconstruct the intensities $(I(u))u \in U$ from the measurements $(y_t)_{t=1}^T$.

The 2-D Radon transform is a mathematical relationship that may be used for reconstructing the emission intensities of volumetric region U when the set of measurements $(y_t)_{t=1}^T$ is unconstrained. The Radon transform is not statistical and does not take into account the Poissonian nature of the counts. In addition, it models the views as line projections. The Radon transform maps the spatial domain (x,y) to the Radon domain (p,$\phi$). For a fixed projection angle, the Radon transform is simply a projection of the object. A technique known in the ART as filtered back-projection (FBP) uses a back-projection operator and the inverse of the Radon transform to reconstruct the intensity distribution in volumetric region U from measurements $(y_t)_{t=1}^T$.

The basic, idealized problem solved by the FBP approach is to reconstruct an image from its Radon transform. The Radon transform, when properly defined, has a well-defined inverse. However, in order to invert the transform one needs measured data spanning 180°. In many medical imaging situations, the positioning of the detecting unit relative to the emitting object is constrained, so that complete measured data is not available. Reconstruction based on filtered back-projection is therefore of limited use for medical imaging. Maximum likelihood (ML) and Maximum A Posteriori (MAP) estimation methods, which address the statistical nature of the counts, have been found to provide better image reconstructions than FBP.

Limited-angle tomography is a reconstruction technique in the related art which reconstructs an image from projections acquired over a limited range of angular directions. The success of the reconstruction process depends upon the extent of the angular range acquired compared with the angular range of the missing projections. Any reconstruction from a limited range of projections potentially results in spatial distortions (artifacts) in the image. Limited angle techniques can be applied for both the Radon transform and the statistical models, but better results are generally achieved within the statistical framework. While it is known that the severity of the artifacts increases with the increasing angular range of the missing projections, limited-angle tomography does not provide information on which projections should be used in order to most effectively reconstruct the image.

ML estimation is a widely used method in the related art for reconstructing an image from a constrained set of measurements. A parameterization of the generative model described above is obtained by assigning an intensity I(u) to every voxel in U. The likelihood of the observed data y=(yt)t, given the set of parameters I={I(u):u∈U} is:

$$L(y \mid I) = \ln P(y \mid I) = \ln \prod_t P(y_t \mid I) = \sum_t \ln P\left(\sum_u x_t(u) \;\middle|\; I\right) \quad (1)$$

$$= \sum_t \ln \text{Poisson}\left(y_t \;\middle|\; \sum_u \phi_t(u)I(u)\right)$$

$$= \sum_t \left\{ \begin{array}{l} -\sum_u \phi_t(u)I(u) + \\ y_t \ln \sum_u \phi_t(u)I(u) - \ln(y_t!) \end{array} \right\}$$

Note that the lower and upper bound of an indexing variable, such as voxels u and time index t, are omitted in the following description, when they are clear from the context.

There is currently no analytic way to solve Eqn. 1 for the maximum of the likelihood function. However, optimization methods that find local maxima of the likelihood are known. One such method is the Expectation-Maximization (EM) process.

Since the data generated by the model is only partially observable by our measurements, a basic ingredient of the EM formalism is to define a set of random variables that completely define the data generated by the model. In the current case, since Yt=ΣuXt(u), the set of variables {Xu(t): u∈U; t=1, . . . , T} is such a set; the generated data is x=(xt)t, where xt=(xt(u))u, and the observed data y is completely determined by x. The main tool in the EM formalism is the complete data likelihood:

$$\ln P(x \mid I) = \ln \prod_t P(x_t \mid I) = \sum_t \ln \prod_u \text{Poisson}(x_t(u) \mid \phi_t(u)I(u)) \quad (2)$$

$$= \sum_t \sum_u \{-\phi_t(u)I(u) + x_t(u)\ln(\phi_t(u)I(u)) + \ln(x_t(u)!)\}$$

Since the likelihood depends on the complete data, which is only partially observable, we take its expectation with respect to the overall volume of the unobserved data, given the current set of hypothesized parameters (i.e. the current estimator). The result is a function Q(I|I') which assigns likelihood to sets I of model parameters, given the current set I', and given the observed data y:

$$Q(I \mid I') = E[\ln P(x \mid I)y; I'] \quad (3)$$

$$= \sum_t \sum_u \{-\phi_t(u)I(u) + E[x_t(u) \mid y_t; I']\ln(\phi_t(u)I(u)) + C\}$$

where C is a term which is independent of the intensities I. The function Q(I|I') is maximized by the following new estimates:

$$I(u) = \frac{1}{\sum_t \phi_t(u)} \sum_t [x_t(u) \mid y_t; I']; \quad (4)$$

$$\forall u \in U.$$

The expectation in Equation 4 is obtained as follows:

$$P_{X_t(u)}(x_t(u) \mid y_t; I') = \frac{P_{Y_t}(y_t \mid x_t(u); I') P_{X_t(u)}(x_t(u) \mid I')}{P_{Y_t}(y_t \mid I')} \quad (5)$$

$$= \frac{\text{Poisson}\left(y_t - x_t(u) \;\middle|\; \sum_{v \ne u} \phi_t(v)I'(v)\right) \text{Poisson}(x_t(u) \mid \phi_t(u)I'(u))}{\text{Poisson}\left(y_t \;\middle|\; \sum_v \phi_t(v)I(v)\right)}$$

$$= \text{Binomial}\left(x_t(u) \;\middle|\; \frac{\phi_t(u)I'(u)}{\sum_v \phi_t(v)I'(v)}; y_t\right)$$

It follows that $$E[xt(u) \mid yt; I'] = y_t \frac{\phi_t(u)I'(u)}{\sum_v \phi_t(v)I'(v)},$$

and hence the EM iteration is:

$$I(u) = \frac{1}{\sum_t \phi_t(u)} \sum_t y_t \frac{\phi_t(u)I'(u)}{\sum_v \phi_t(v)I'(v)} \quad (6)$$

It is provable that each EM iteration improves the likelihood. Thus, given a random starting estimator, the EM algorithm iterates the above improvement step until it converges to a local maximum of the likelihood. Several random starts increase the chance of finding a globally good estimator.

It is usually desired to maximize the expected posterior probability (given a proper prior) rather than the expected likelihood. In that case we assume a prior probability on the intensities P(I)=ΠuP(I(u)). A proper conjugate prior for the Poisson distribution is the Gamma distribution:

$$P(I(u)) = \text{Gamma}(I(u) \mid \alpha_u; \beta_u) = \frac{\beta_u^{\alpha_u+1}}{\Gamma(\alpha_u+1)} I(u)^{\alpha_u} e^{-\beta_u I(u)} \quad (7)$$

Now the maximization is done on Q(I|I')=E[lnP(x|I)p(I) |y; I']. Plugging the Gamma prior into Q, and solving for I(u), we get the following EM iteration for the maximum posterior estimation:

$$I(u) = \frac{\alpha_u + \sum_t E[x_t(u) \mid y_t; I']}{\beta_u + \sum_t \phi_t(u)} \quad (8)$$

$$= \frac{1}{\beta_u + \sum_t \phi_t(u)}\left[\alpha_u + \sum_t y_t \frac{\phi_t(u)I'(u)}{\sum_v \phi_t(u)I'(v)}\right] \quad (9)$$

The EM update step can be formulated in matrix notation as follows. Let Φ be the matrix of the projections [φt(u)]t,u, and let I, I',y, α and β be represented as column vectors. Equation 8 can be written in vector and matrix notations as:

$$I = \frac{\alpha + I' \cdot \left(\Phi^T \frac{y}{\Phi I'}\right)}{\beta + \Phi^T 1} \quad (10)$$

where the explicit multiplication and division denote element-wise operations, and where 1 is a vector (of the appropriate length) consisting solely of 1's.

Limited computational resources (i.e., when the entire projection matrix Φ cannot be kept in memory) may require breaking the update computation according to a partition of Φ into a set of sub-matrices (Φi). In that case the intensities can be updated gradually (using only one sub-matrix at each step) according to the following computation:

$$I = \frac{\alpha + I' \cdot \sum_i \Phi_i^T \frac{y_i}{\Phi_i I'}}{\beta + \sum_i \Phi_i^T 1} \quad (11)$$

where yi denotes the vector of observations that are obtained using the views of Φi.

In order to achieve a reconstructed image which is adequate for medical diagnostic and treatment purposes, a high-resolution image of the tested object must be obtained. When high-resolution detecting units are used, their efficiency is relatively low, and the detecting units must remain at each position for a relatively long time in order to achieve a high probability of detection. Since during medical testing, measurements are generally performed at many locations as the detecting unit is moved relative to the observed organ, the testing procedure generally requires a long time and is physically and emotionally difficult for the patient. Additionally, reconstruction is based upon a large quantity of data, and is a lengthy and computationally complex process.

Reference is now made to FIG. 13, which is a schematic flowchart that illustrates steps of a typical prior art gated image reconstruction method. In FIG. 13, i denotes a frame counter and M denotes the number of frames. Usually, after all the M datasets are fetched, as shown at 2, and i is set with 1, as shown at 4, the dataset that corresponds with frame i is loaded into the processing unit, as shown at 6. During the following step, as shown at 8, the processing unit is used to perform a frame reconstruction according to the dataset that corresponds with frame i using any suitable reconstruction algorithm known in the art, such as the aforementioned EM algorithm, ordered subset expectation maximization (OSEM), and algebraic reconstruction techniques (ART) FBP.

As shown at 12, after the reconstruction is completed, the frame counter i is incremented by 1. If i is larger than M and there are no more frame the process ends. If i is not larger than M, the next dataset that corresponds with the subsequent frame is loading for reconstruction. In such a manner, the generation of a static imaging of the heart in a specific configuration becomes possible.

However, a known problem of such a method is the high computational load that is needed for the execution thereof. Even when using an ordered set method, such as the aforementioned Hudson et al. method, which is capable of reducing the computational load while giving similar results, the computational power needed to obtain a good image reconstruction is still quite high. Such a high computational load results in a longer reconstruction time that reduces the throughput of the processing unit and requires a more expensive processing hardware.

There is thus a widely recognized need for, and it would be highly advantageous to have, a method and an apparatus for image reconstruction in nuclear medicine imaging devoid of the above limitations.

SUMMARY OF THE INVENTION

According to one aspect of the present invention there is provided a method for iteratively reconstructing a volumetric image of an overall volume from radioactive emissions, the method comprising:

a) obtaining radioactive emissions from the overall volume, the overall volume comprising at least a part of a body organ or other body portion;

b) using the radioactive emissions to reconstruct an initial volumetric image of the overall volume, the initial volumetric image containing an initial location and initial shape of the at least a part of a body organ or other body portion and an initial estimation of number of photons emitted from the at least a part of a body organ or other body portion; and c) reconstructing a further volumetric image from the initial volumetric image by an iterative process using object implantation for refining reconstruction, wherein the object implantation includes:

providing a model of at least a portion of the overall volume, the model including a general location and shape of the at least a part of a body organ or other body portion and an expected number of photons emitted from the at least a part of a body organ or other body portion;

replacing, at the general location, at least a portion of the initial volumetric image with the general shape of the at least a part of a body organ or other body portion, based on the model;

determining an improved estimation of a number of photons emitted from the at least a portion of the initial volumetric image, based on the expected number of photons, wherein the improved estimation is an increase in number of photons over the initial estimation; and replacing the initial estimation of number of photons with the improved estimation, wherein the object implantation is used one or more times during the iterative process, each time for providing a better starting point for performing a next iteration of the iterative process, whereby the improved estimation is used to redistribute photon counts in an iteration.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps may be implemented by hardware or by software on any operating system of any firmware or a combination thereof. For example, as hardware, selected steps of the invention may be implemented as a chip or a circuit. As software, selected steps of the invention may be implemented as a plurality of software instructions being executed by a computer using any suitable operating system. In any case, selected steps of the method and system of the invention may be described as being performed by a data processor, such as a computing platform for executing a plurality of instructions.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 2A:
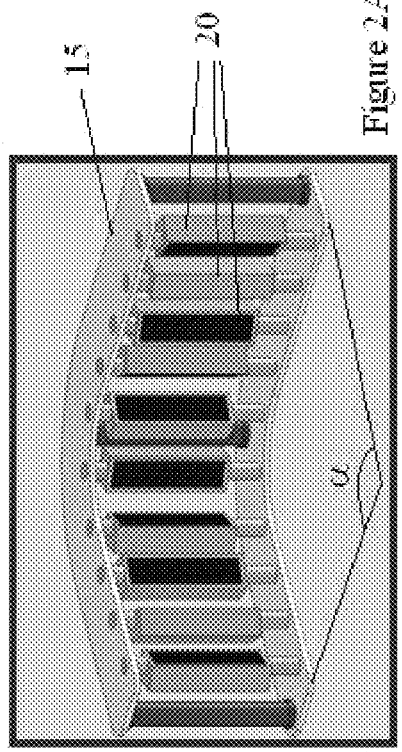
Figure 2B:
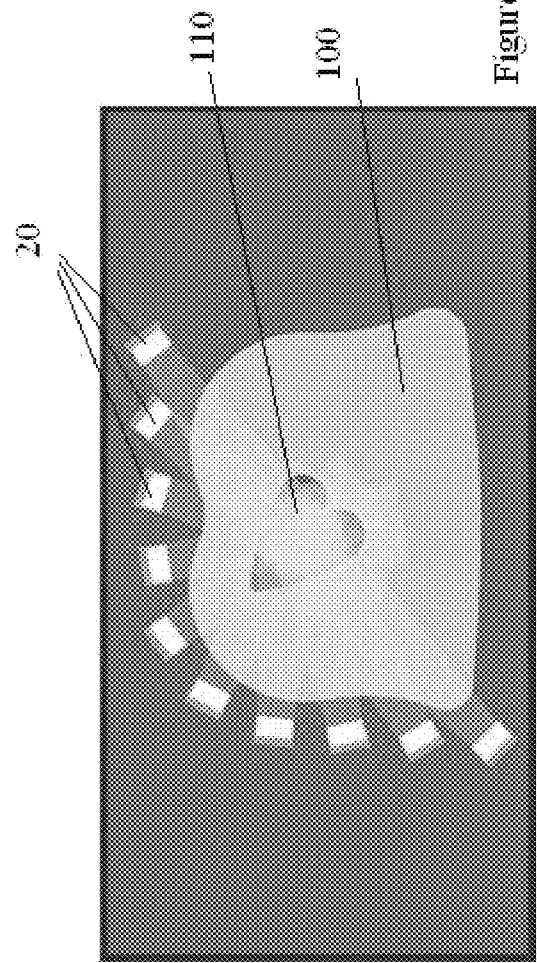

FIGS. 1A-1D schematically illustrate a dynamic SPECT camera, in accordance with embodiments of the present invention;

FIGS. 2A and 2B schematically illustrate the camera structure with the assemblies, in accordance with an embodiment of the present invention.

FIGS. 3A-3D schematically illustrate viewing positions, in accordance with embodiments of the present invention.

FIGS. 4A-4F schematically illustrate stereo views and cross views, in accordance with embodiments of the present invention.

Figure 5C:
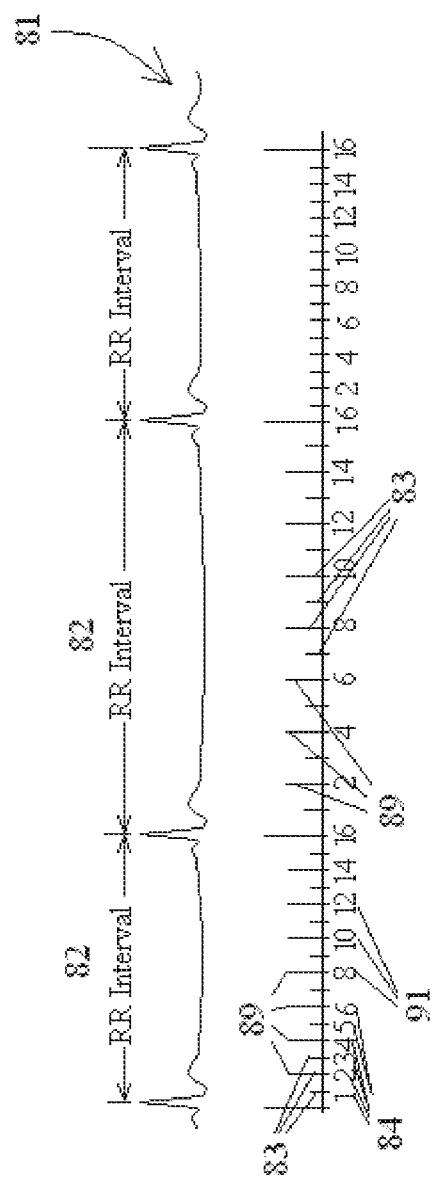
Figure 5D:
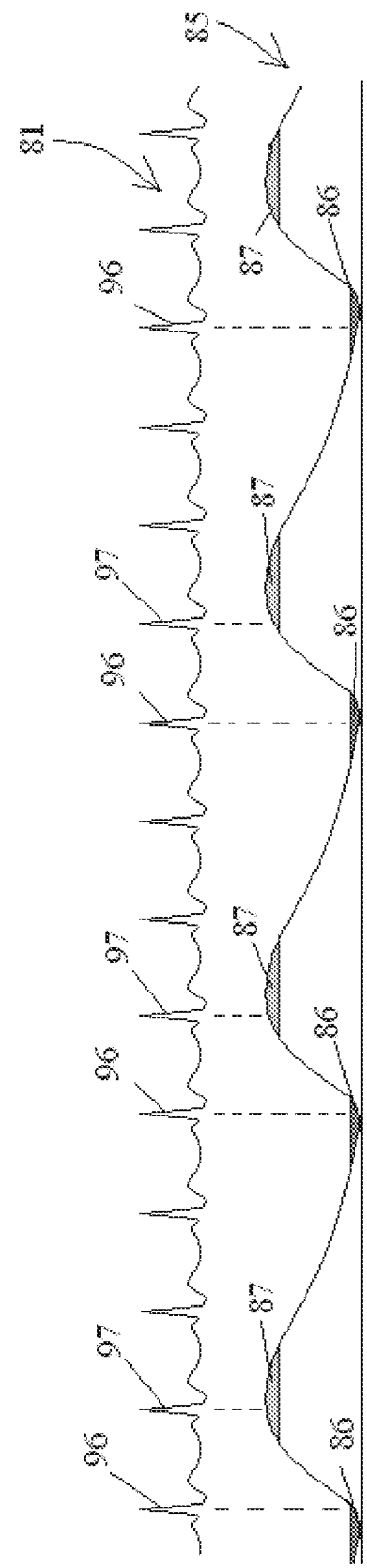
Figure 5E:
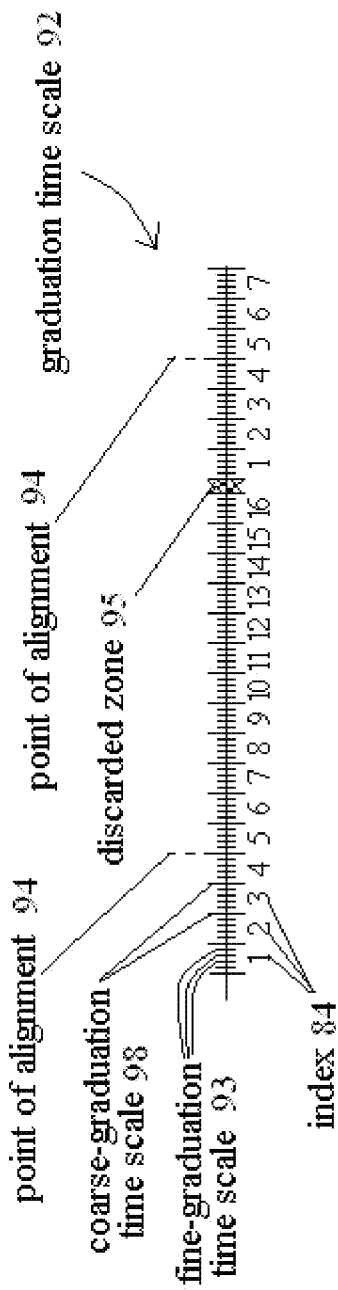
Figure 5F:
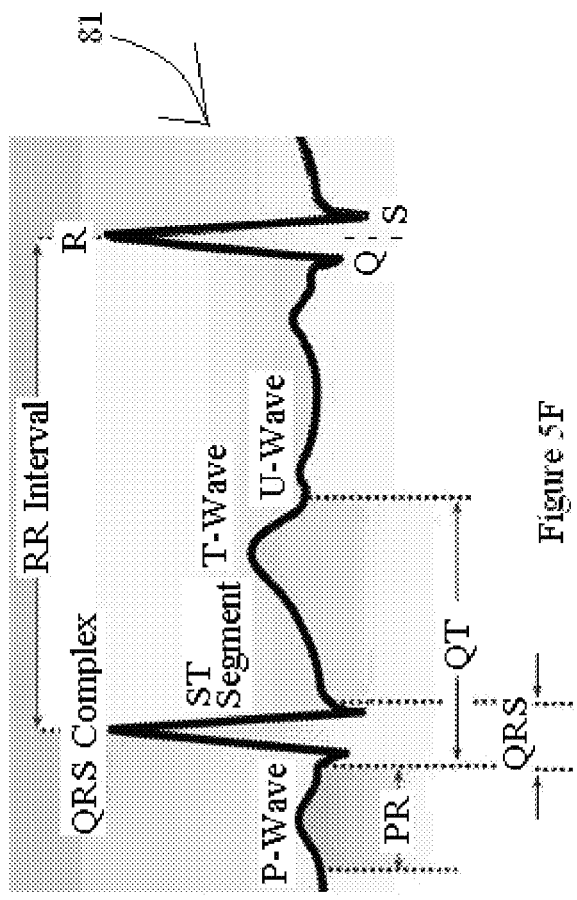
Figure 7:
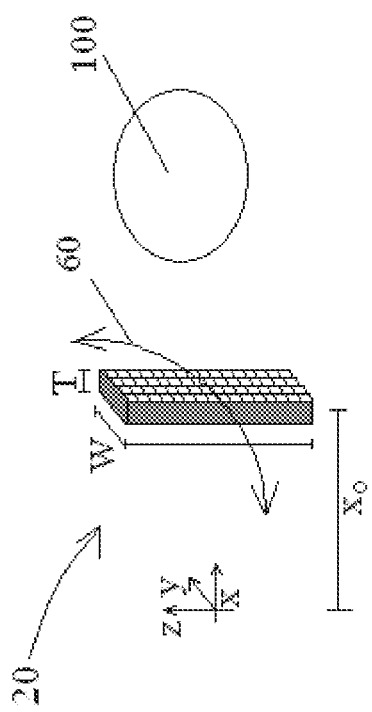
Figure 11:
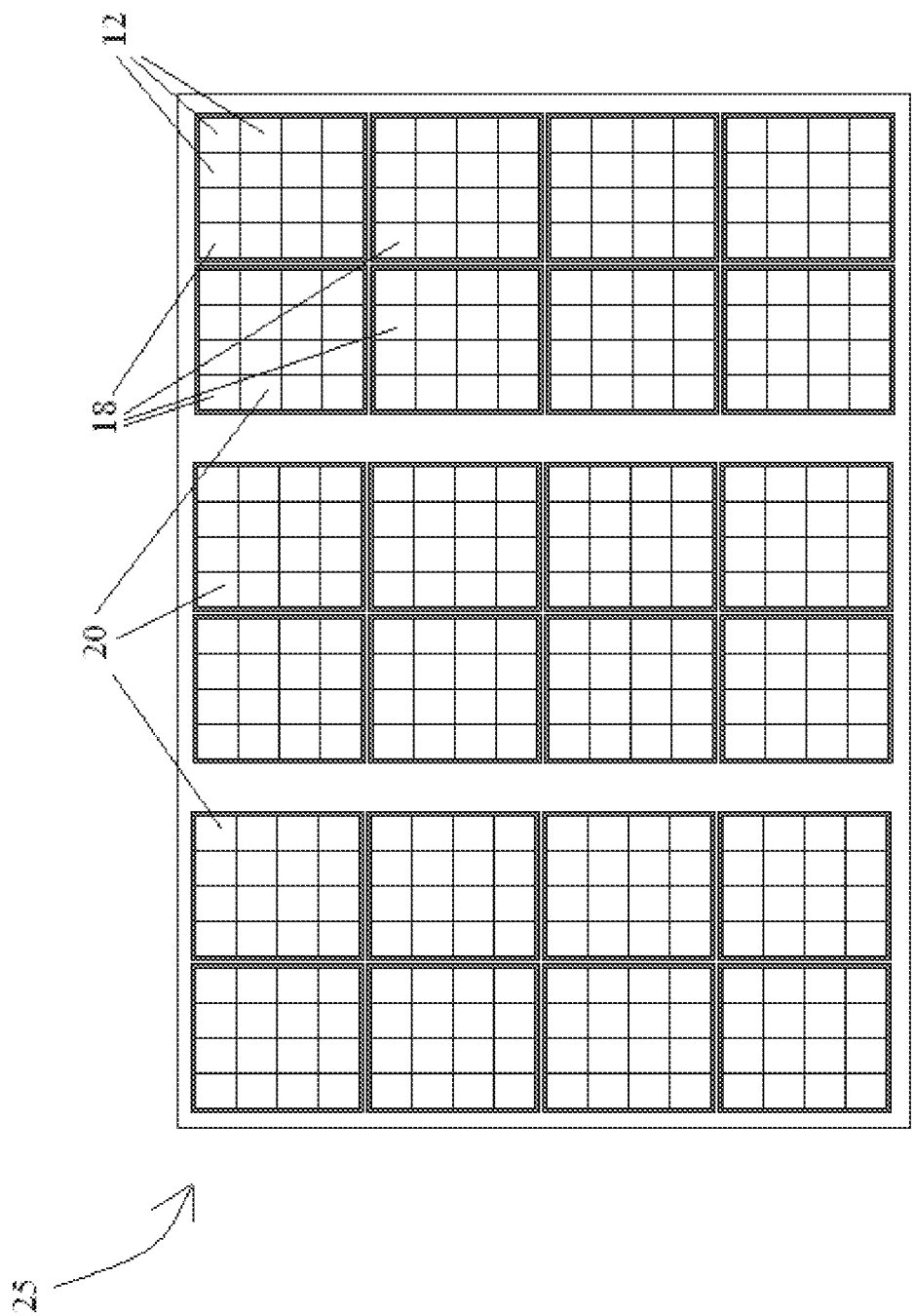
Figure 12:
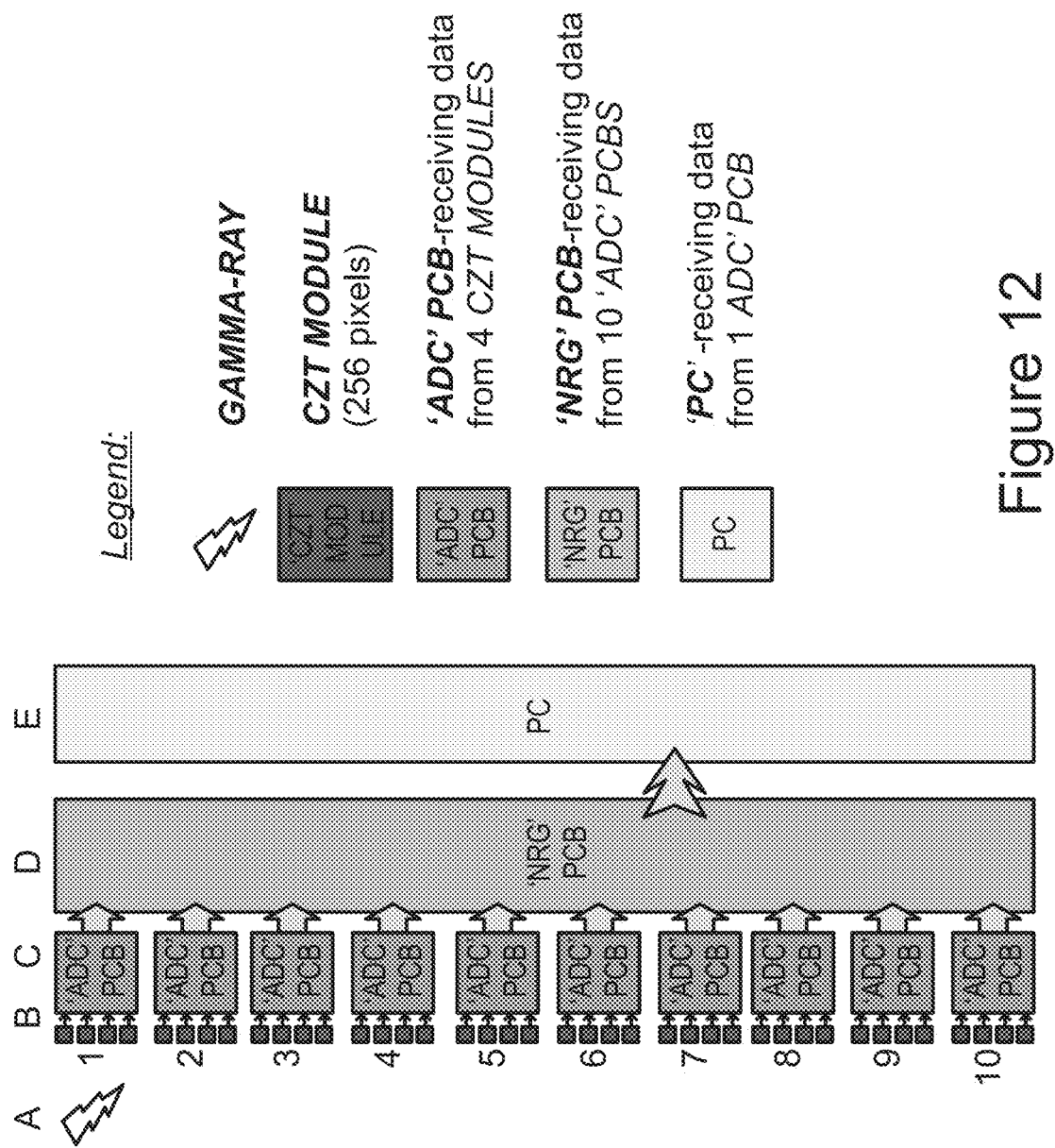
Figure 13:
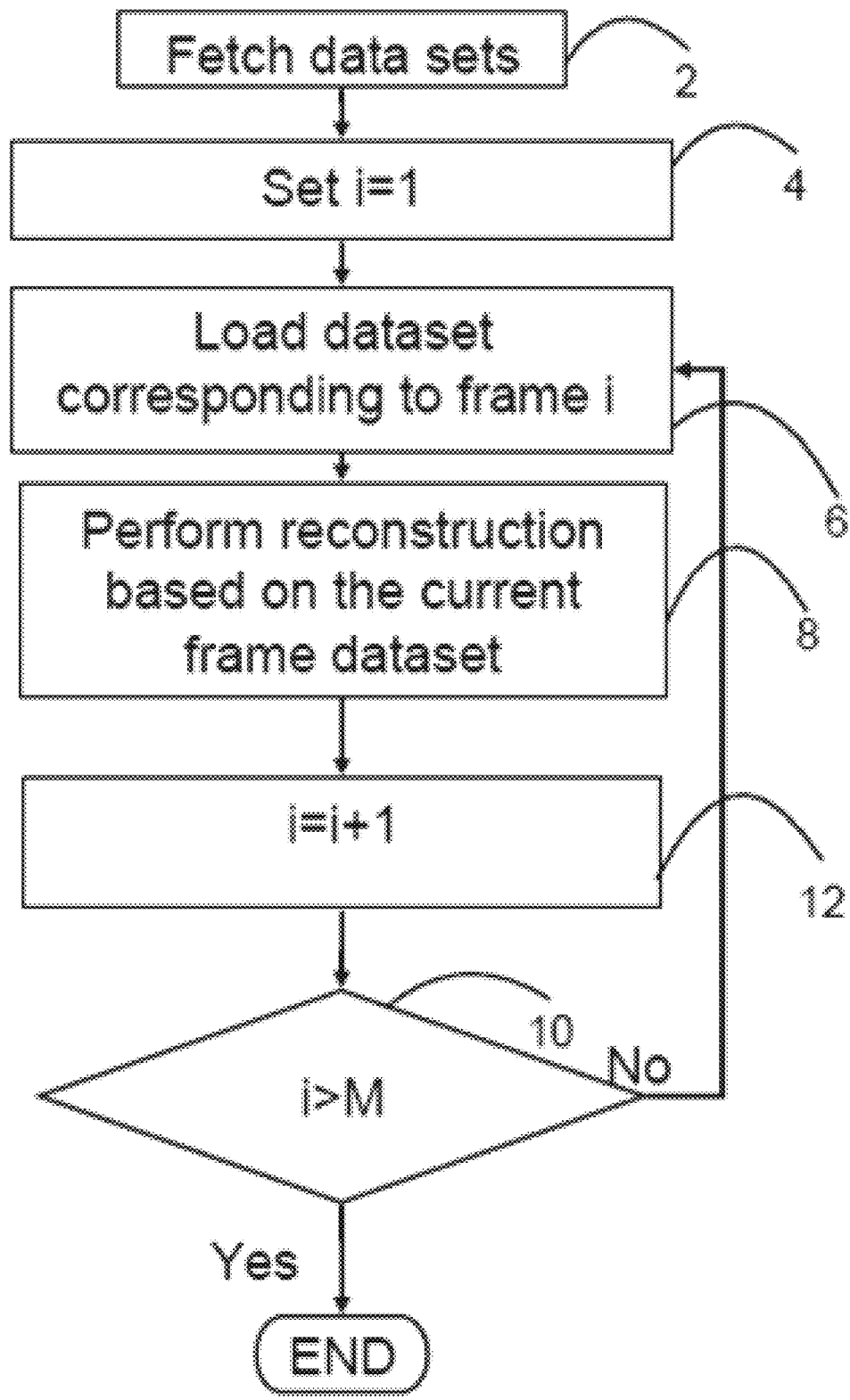
Figure 14:
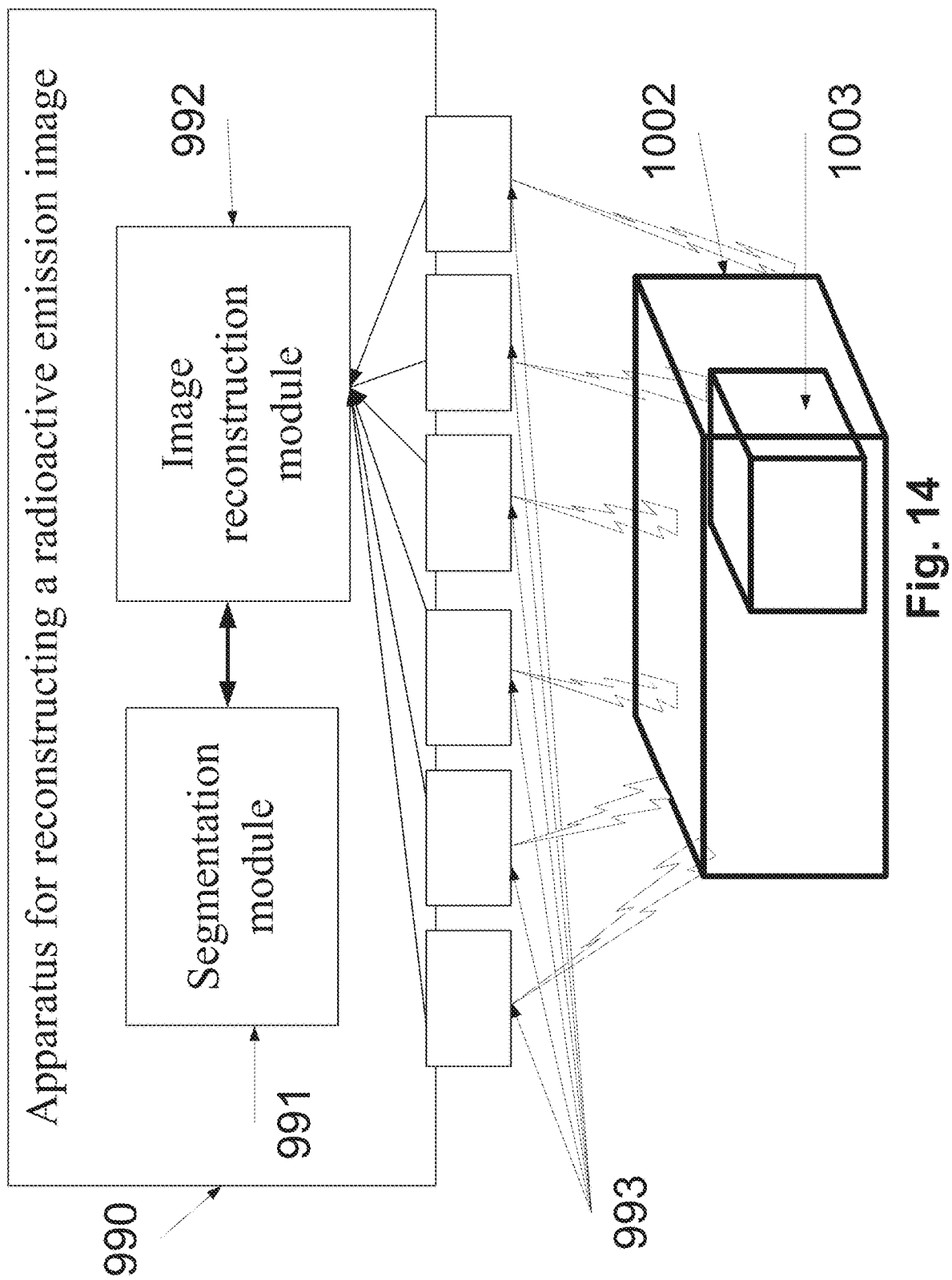
Figure 15:
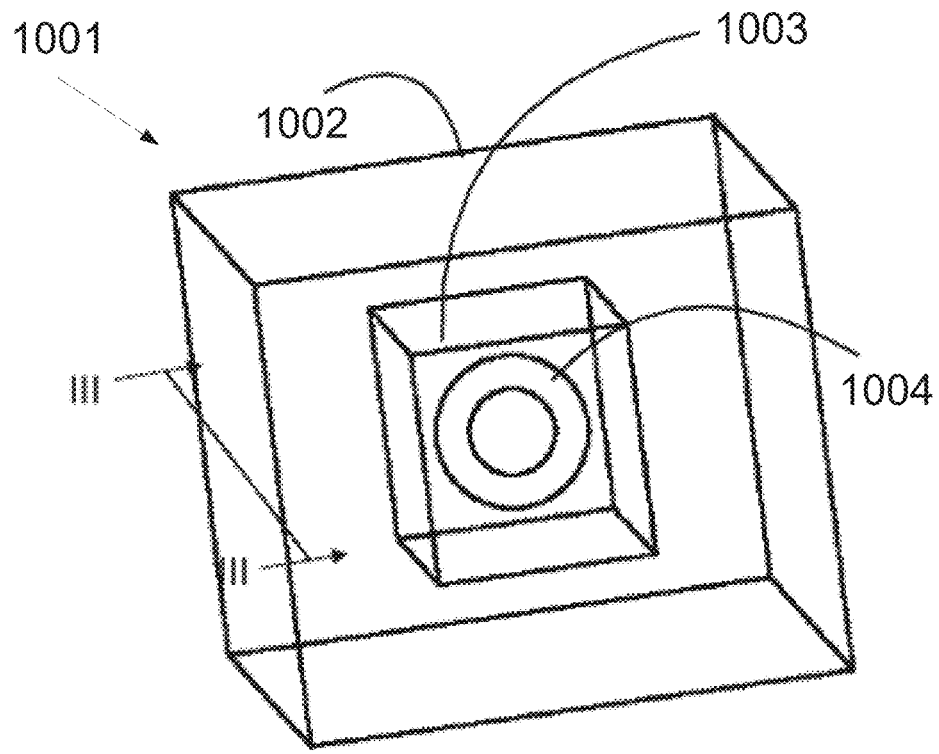
Figure 16:
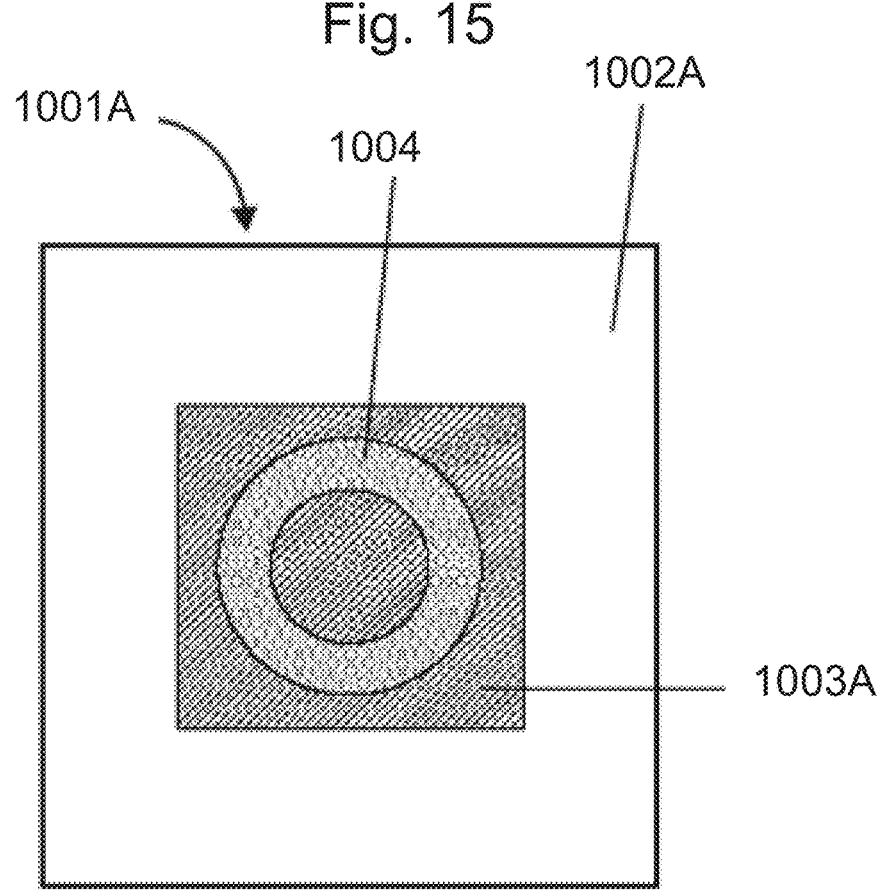
Figure 17:
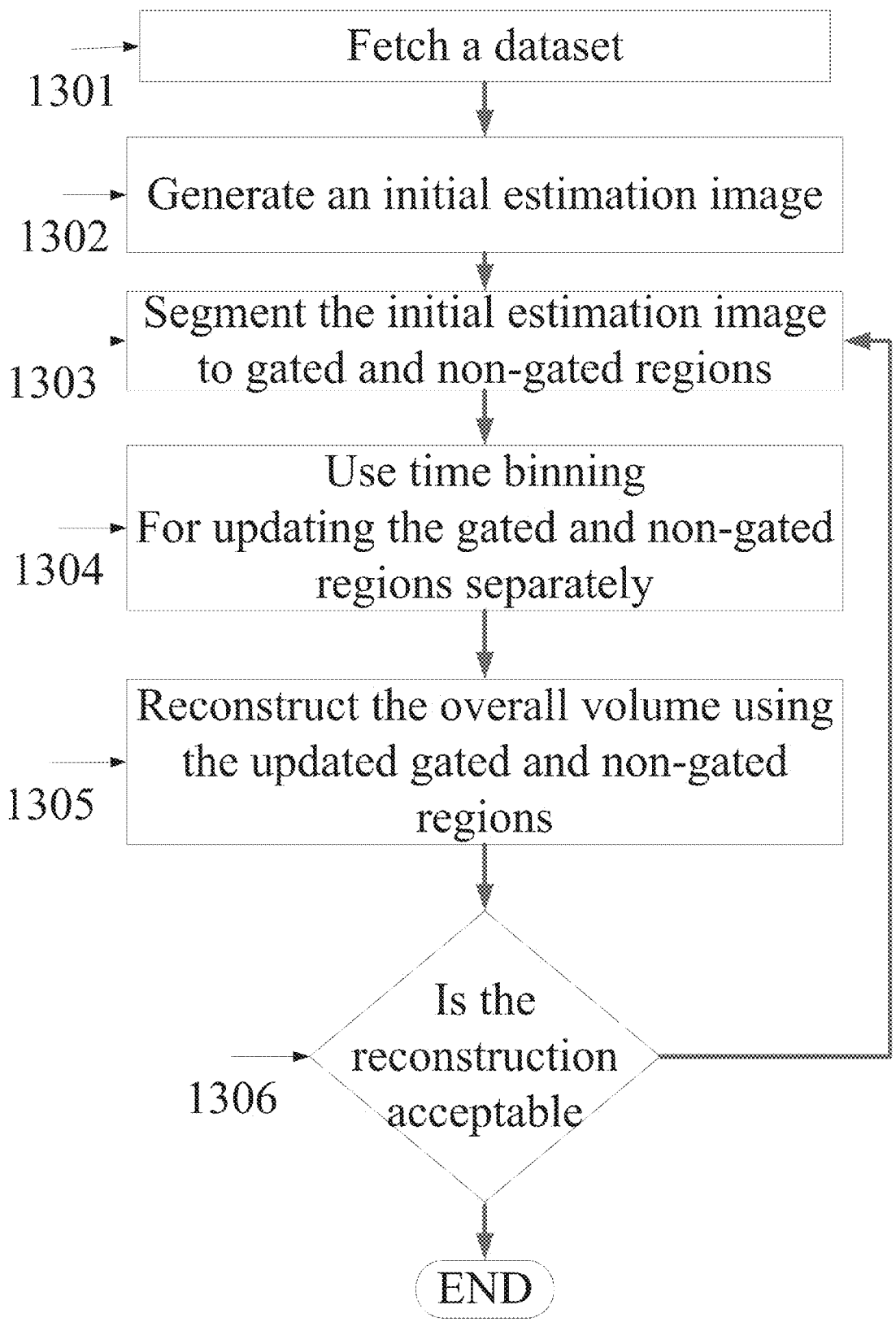
Figure 18:
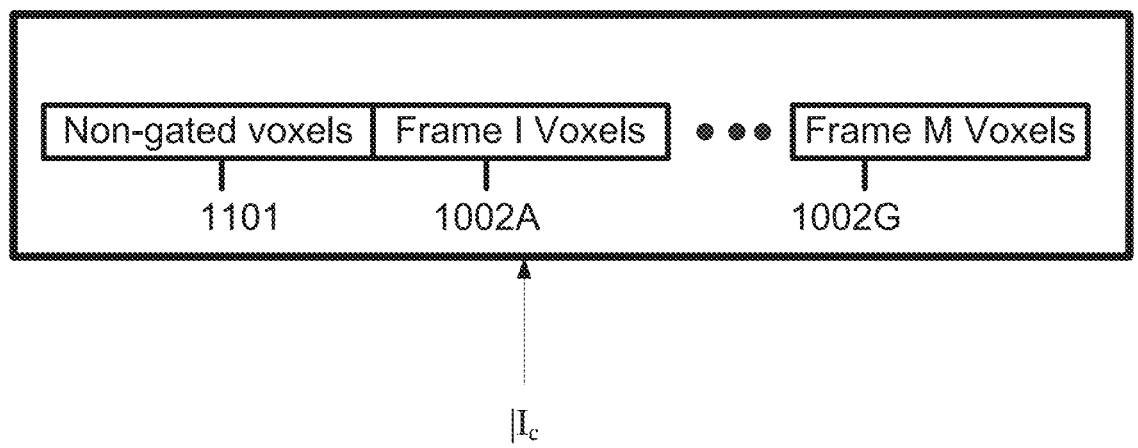
Figure 19:
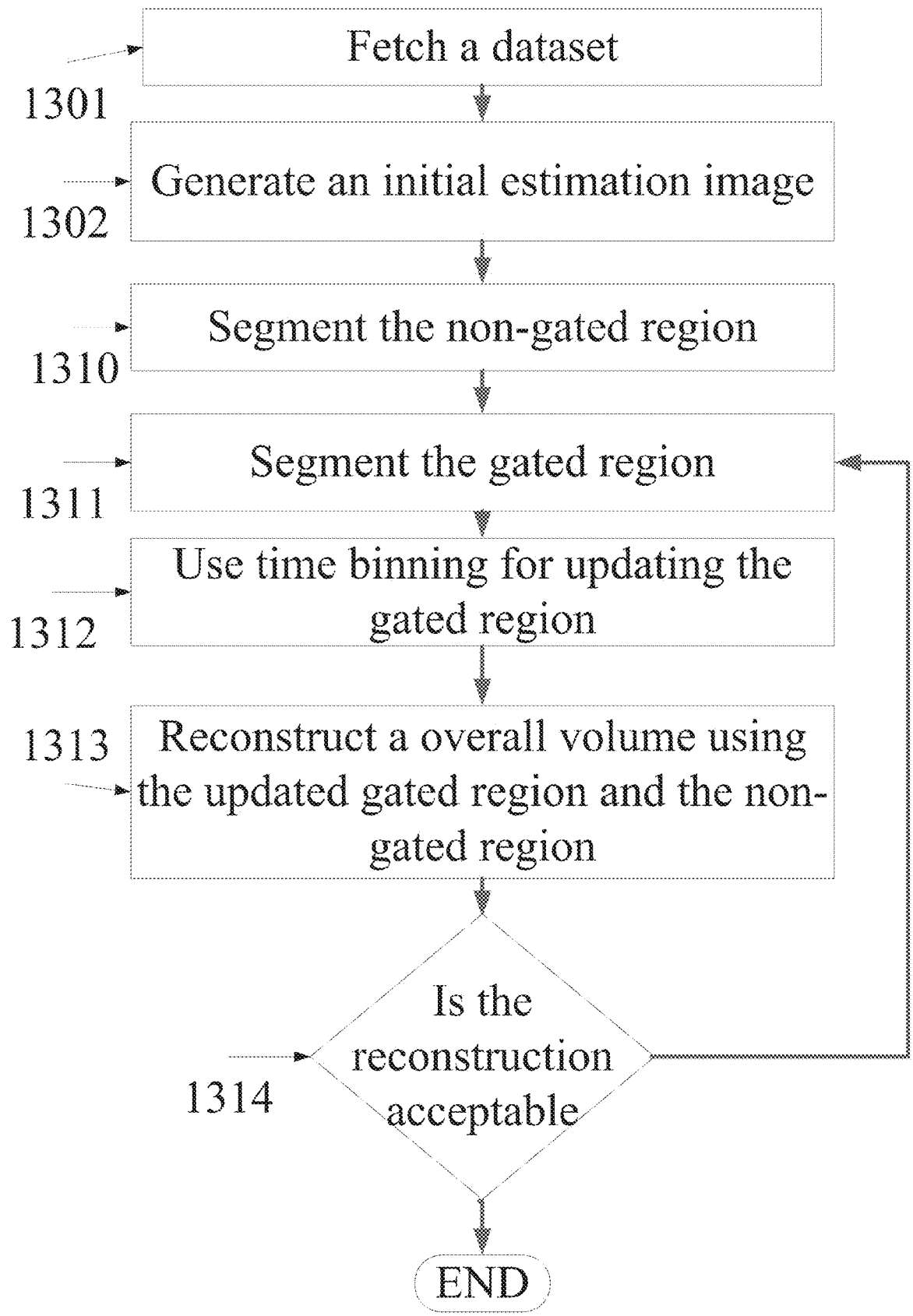
Figure 20:
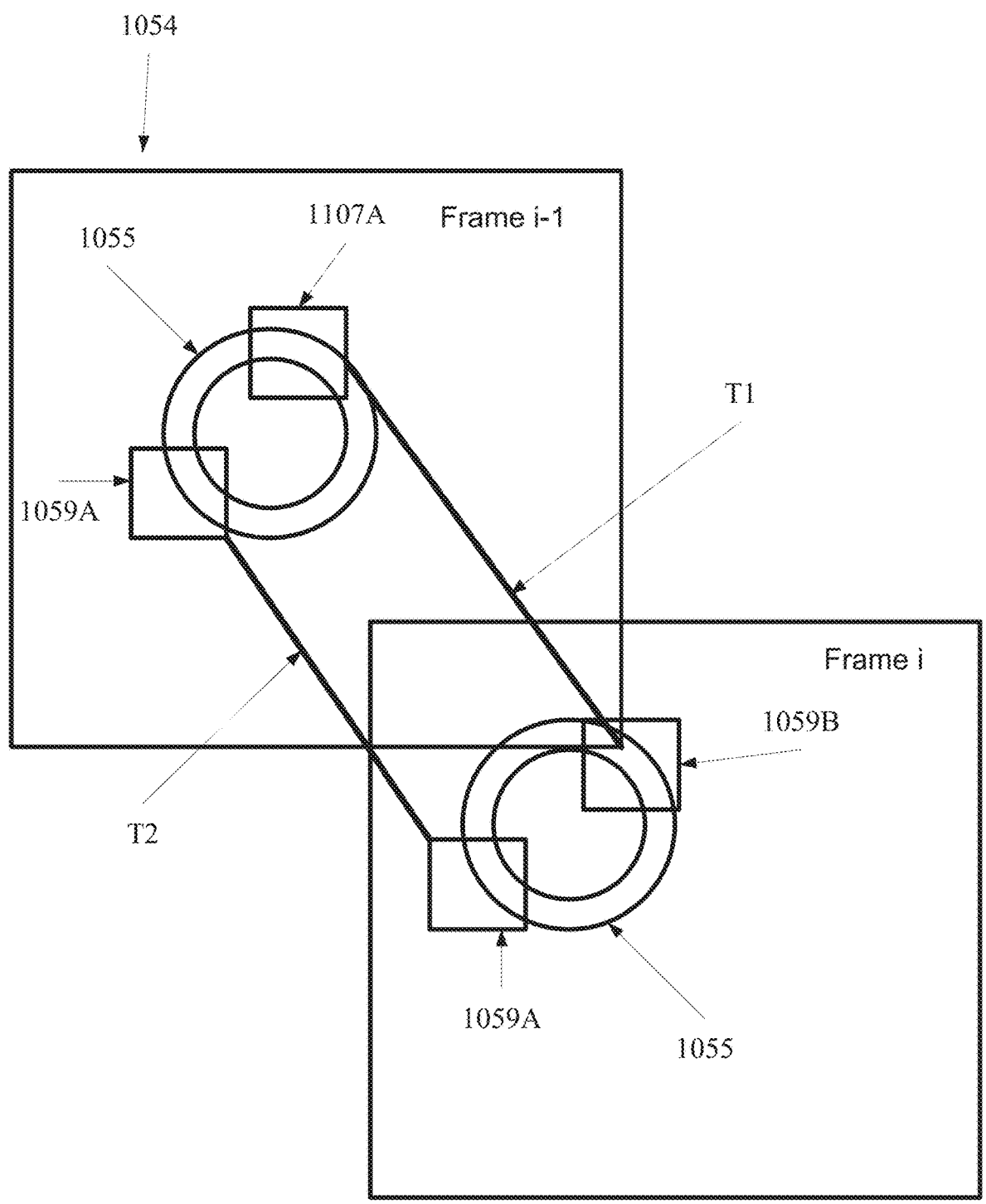

FIGS. 5A and 5B illustrate experimental radiopharmaceutical data, as known;

FIGS. 5C-5F illustrate cardiac gating, in accordance with embodiments of the present invention;

FIG. 6A-6I illustrate an intracorporeal dynamic SPECT camera, in accordance with embodiments of the present invention;

FIG. 7 illustrates assembly-damping parameters, in accordance with embodiments of the present invention;

FIGS. 8A and 8B schematically illustrate grid and anatomical construction of voxels, in accordance with embodiments of the present invention;

FIGS. 9A-9J present experimental data, obtained by the dynamic SPECT camera, in accordance with embodiments of the present invention;

FIG. 10 presents experimental data, obtained by the dynamic SPECT camera, in accordance with embodiments of the present invention;

FIG. 11 illustrates components of the dynamic SPECT camera, in accordance with embodiments of the present invention;

FIG. 12 illustrates an electrical scheme, in accordance with embodiments of the present invention;

FIG. 13 is a schematic flowchart that illustrates steps of a typical prior art gated image reconstruction method;

FIG. 14 is a schematic illustration of an apparatus for reconstructing a radioactive emission image of an input overall volume having dynamic and static volumetric regions, according to a preferred embodiment of present invention;

FIG. 15 is a schematic isometric view of the input overall volume that is depicted in FIG. 14, according to one embodiment of the present invention;

FIG. 16 is a schematic cross-sectional view of the input overall volume of FIG. 15, according to one embodiment of the present invention;

FIG. 17 is a flowchart that depicts a method for reconstruction an input overall volume using anatomically varying time-bin lengths, according to one embodiment of the present invention;

FIG. 18 is a graphical representation of a one-dimensional vector of voxels that represents the reconstruction of the input overall volume, according to one embodiment of the present invention;

FIG. 19 is another flowchart that depicts another method for reconstruction an input overall volume using anatomically varying time-bin lengths, according to another embodiment of the present invention; and FIG. 20 is a graphical representation of a position of two selected sub-regions in two sequential frames, according to another embodiment of the present invention.

DESCRIPTION OF SPECIFIC EMBODIMENTS OF THE INVENTION

The present invention relates to an apparatus and a method for reconstructing a radioactive emission image of a overall volume having dynamic and static volumetric regions. The reconstructing is based on gated images with anatomically varying time-bin lengths. The apparatus and the method are designed to allow the segmentation of the radioactive emission image to gated and non-gated regions. In such a manner, the reconstructions radioactive emissions from the dynamic volumetric region and the static volumetric region are carried out separately. Thus, the high computational throughput that is needed in order to reconstruct a dynamic volumetric region, such as the heart, using time binning techniques has less or no effect on the reconstruction of the static volumetric region, as further described below. The disclosed apparatus comprises a number of detectors, such as PET or SPECT detectors, which are designed for obtaining radioactive emissions from the overall volume and an image reconstruction module that is designed for generating radioactive emission images of the overall volume according to the obtained radioactive emissions. The apparatus further comprises a segmentation module that is designed for segmenting an initial radioactive emission image to gated and non-gated regions, according to the dynamic and static volumetric regions of the overall volume. The image reconstruction module is designed to reconstruct separately the gated and non-gated regions in the radioactive emission image respectively according to radioactive emissions the dynamic and static volumetric regions.

The method for reconstructing a radioactive emission image of a overall volume having static and dynamic volumetric regions comprises several steps. During the first step, radioactive emissions are obtained from the overall volume. Then, an initial radioactive emission image of the overall volume is reconstructed according to the radioactive-emission data. In the following step, the initial radioactive emission image is segmented to gated and non-gated regions, respectively according to the dynamic and static volumetric regions. During the last step, the radioactive emission image is reconstructed, wherein the gated region is according to radioactive emissions from said dynamic volumetric region and the non-gated region is separately reconstructed according to radioactive emissions from the static volumetric region.

In another embodiment, only the dynamic volumetric region is reconstructed using time binning. The static volumetric region is reconstructed according to the initial radioactive emission image. Preferably, time binning of different anatomical segments has dynamically varying time-bin lengths, as further described below.

The principles and operation of the dynamic SPECT camera according to aspects of the present invention may be better understood with reference to the drawings and accompanying descriptions.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 14, which is a schematic illustration of an apparatus 990 for reconstructing a radioactive emission image of an input overall volume 1002 having dynamic 1003 and static 1002 volumetric regions, according to a preferred embodiment of present invention. In one embodiment of the present invention, the input overall volume 1002 is the thorax, the static volumetric region is the related viscus, and the dynamic volumetric region is the heart and the area that confines it. The apparatus 990, which is preferably a SPECT camera, has a number of detecting units 993, such as SPECT detectors. Each one of the detectors 993 is designed for obtaining radiation emission that is emitted from the input overall volume 1002, as described below, and for generating accordingly radioactive-emission data. The apparatus 990 comprises an image reconstruction module 992 that is connected to the detecting units 993. The image reconstruction module 992 is designed for generating radioactive emission images according to the radioactive-emission data. The images are preferably gated, as described below. The apparatus 990 further comprises a segmentation module 991 that is designed for segmenting an initial radioactive emission image, which has been generated by the image reconstruction module 992, to gated and non-gated regions according to the dynamic and static volumetric regions. The gated and non-gated regions are used by the image reconstruction module 992 for separately reconstructing the dynamic and static volumetric regions, as further described below in the anatomically varying time-bin lengths section.

Reference is now made to a more elaborated description of a preferred apparatus 990.

Dynamic Spect Camera
Design Description of the Dynamic SPECT Camera

As described above, in one embodiment of the present invention the apparatus 990 is a dynamic SPECT camera. Hereinbelow a description of a dynamic SPECT camera with temporal and spatial resolutions, which meet and even outperforms those of PET, and with a high spectral resolution not available in PET is given.

Temporal resolution, as used herein, relates to a minimal acquisition time for a tomographic reconstruction image of a predetermined volumetric region, for example 15×15×15 cubic centimeters, and predetermined spatial resolution, for example, 10×10×10 cubic millimeters. The minimal acquisition time may be, for example, 30 seconds, 10 seconds, or 1 second.

Reference is now made to FIGS. 1A-1D, which schematically illustrate a dynamic SPECT camera 10 that is configured for capturing gated images and non-gated image, in accordance with embodiments of the present invention. The dynamic SPECT camera 10 comprises: an overall structure 15, which defines proximal and distal ends and, with respect to a body 100; a number of assemblies 20, for example, 6, 9, or 16 assemblies 20, arranged on the overall structure 15, forming an array 25 of the assemblies 20. Each one the each assemblies 20 comprises a number of detecting units 12. Each detecting unit 12 includes a single-pixel detector 14 for detecting radioactive emissions and a dedicated collimator 16, attached to the single-pixel detector 14, at the proximal end thereof, for defining a solid collection angle δ for the detecting unit 12.

Additionally, each assembly 20 comprises an assembly motion provider 40, configured for providing the assembly 20 with individual assembly motion, with respect to the overall structure 15, during the acquisition of radioactive-emission data for a tomographic image.

The dynamic SPECT camera 10 further includes a timing mechanism 30, in communication with each single-pixel detector 14, configured for enabling time binning of the radioactive emissions impinging upon each single-pixel detector 14 to periods, which are not greater than substantially 30 seconds. As the timing mechanism 30 has can control each one of the single-pixel detector 14 separately, each one of the single-pixel detectors 14 can be configured according to a different time binning scheme. In one embodiment of the present invention, the time binning scheme, which is applied to a certain detector, is determined according to the region in the input overall volume that the detector is designed to detect.

The dynamic SPECT camera 10 further includes a position tracker 50, which is designed for providing information on the position and orientation of each detecting unit 12, with respect to the overall structure 15, substantially at all times, during the individual assembly motion.

The dynamic SPECT camera 10 is configured for acquiring a tomographic reconstruction image of a region of interest of about 15×15×15 cubic centimeters, for example, of a target organ 110, such as a heart or a stomach, during an acquisition period no greater than 300 seconds, at a spatial resolution of at least 10×10×10 cubic millimeters.

It will be appreciated that the time period may be no greater than 200 seconds, 100 seconds, 60 seconds, 30 seconds, 10 seconds, or 1 second.

Additionally, the dynamic SPECT camera 10 is configured for acquiring a series of tomographic reconstruction images of a region of interest, as a function of time, at a rate of at least a tomographic reconstruction image every 300 seconds.

Again, the rate may further be every 200 seconds, 100 seconds, 60 seconds, 30 seconds, 10 seconds, or 1 second.

In accordance with embodiments of the present invention, the individual assembly motion may be, for example, an assembly oscillatory sweeping motion, as described by an arrow 60. Additionally or alternatively, the individual assembly motion may be a first oscillatory lateral motion, as described by an arrow 80. Additionally or alternatively, the individual assembly motion may be a second oscillatory lateral motion, orthogonal to the first, as described by an arrow 90. Thus, the assembly motion provider 40 may comprise between one and three motion providing units, for the different assembly motions.

Alternatively, the individual assembly motion is an assembly oscillatory sweeping motion, as described by an arrow 60, while the array 25 moves with either the first or the second oscillatory lateral motions, described by the arrows 80 and 90, or with both.

Additionally, the detecting units 12 may be grouped into square or rectangular blocks 18, for example, of 4×4 detecting units 12, as seen in FIG. 1A, or of 16×16, 64×64, 64×128 or another number of detecting units 12. Furthermore, the blocks 18 may be provided with individual block oscillatory sweeping motion, as described by an arrow 70, with respect to the overall structure 15, during the acquisition of radioactive-emission data for a tomographic image. Preferably, the block oscillatory sweeping motion is orthogonal to, or at an angle to the assembly oscillatory sweeping motion, described by the arrow 60. Thus, the assembly motion provider 40 may further comprise a dedicated block motion providing unit, in communication with each block of an assembly.

A control unit 55 may be integrated with the dynamic SPECT camera 10, to form a single physical unit, or in communication with the dynamic SPECT camera 10.

A spectral selection mechanism 56, in communication with each of the detecting unit 12, is discussed hereinbelow, under the heading, "dynamically varying spectral bins."

The body 100 may be a human or an animal, and the region of interest, or the target organ 110 may be a heart, a brain, a breast, a stomach, a GI tract, a colon, a prostate, a uterus, a cervix, a vagina, a throat, a gland, a lymph node, a portion of skin, a portion of bone, portion of another tissue, or another body portion.

As seen in FIGS. 1A and 1B, a reference x;y;z coordinate system illustrates a preferred orientation of the dynamic SPECT camera 10 with respect to the body 100, wherein z runs along a length of the body 100. For convenience, the assembly axis along the assembly length will be referred to as the assembly longitudinal axis, and the assembly axis along the assembly width will be referred to as the assembly traverse axis.

Preferably, the assemblies 20 are long and narrow columns, arranged longitudinally against the body 100, wherein the oscillatory sweeping motion, described by an arrow 60, is about the z-axis. It will be appreciated that other arrangements are similarly possible.

As seen in FIG. 1C, illustrating a cross-sectional view in the x-y plane, preferably, the assemblies 20 are arranged in an arc or an arc-like structure, about the body 100, maintaining a shape that follows the body contours, so as to keep as close as possible to the body 100.

FIG. 1D provides details of the detecting unit 12. The collimator has a length L, a collection angle δ, and a septa thickness τ. The single pixel detector is preferably a square of sides D and a detector thickness τd.

Preferred dimensions for the detecting unit 12 may be, for example, 2.46 mm×2.46 mm, and the solid collection angle δ may be at least 0.005 steradians. Generally, there may be 16×64 detecting units 12 per block 18.

The detector 14 is preferably, a room temperature, solid-state CdZnTe (CZT) detector, which is among the more promising that is currently available. It may be obtained, for example, IMARAD IMAGING SYSTEMS LTD., of Rehovot, ISRAEL, 76124, www(dot)imarad(dot)com, or from eV Products, a division of II-VI Corporation, Saxonburg Pa., 16056, or from or from another source. Alternatively, another solid-state detector such as CdTe, HgI, Si, Ge, or the like, or a combination of a scintillation detector (such as NaI(Tl), LSO, GSO, CsI, CaF, or the like) and a photomultiplier, or another detector as known, may be used, preferably with a photomultiplier tube for each single-pixel detector 14 and collimator 16, for accurate spatial resolution.

Reference is further made to FIGS. 2A and 2B that schematically illustrate the structure 15 with the assemblies 20, in accordance with an embodiment of the present invention. As seen, the assemblies 20 are arranged in an arc of an angle α, around the body 100, and move in the assembly oscillatory sweeping motion, about the z-axis, so as to provide a plurality of views of the heart 110, from many positions, along the x-y plane.

As seen in FIGS. 2A and 2B, the dynamic camera 10 is configured for simultaneous acquisition by the assemblies 20, each scanning the same region of interest from a different viewing position, thus achieving both shorter acquisition time and better edge definitions.

Preferably, the structure 15 conforms to the contours of the body 100, to maintain substantial contact or near contact with the body.

The embodiment of FIGS. 2A and 2B illustrates a single type of motion-assembly oscillatory sweeping motion about the z-axis, as described by the arrow 60 (FIG. 1A). In some cases, additional motions or views from additional directions may be desirous, as illustrated in FIGS. 3A-3D, hereinbelow.

Reference is further made to FIGS. 3A-3D, which schematically illustrate viewing positions, in accordance with embodiments of the present invention.

FIG. 3A illustrates a cylindrical target organ 110, with a cylindrical radioactive emission source 115 therein.

As seen in FIG. 3B, a view along the x-axis will observe the cylindrical radioactive emission source 115 as a bar 115.

As seen in FIG. 3C, a view along the y-axis will similarly observe the cylindrical radioactive emission source 115 as a bar 115, thus not adding new information to the view along the x-axis.

It will be appreciated that in the present example, any view along the x-y plane will observe the radioactive emission source 115 as a bar 115.

As seen in FIG. 3D, a view along the z-axis will observe the cylindrical radioactive emission source 115 as a circle 115, adding new information to the views along the x and y axes.

As FIGS. 3A-3D illustrate, at times, views along two axes may be insufficient for a three-dimensional definition of an object, and it may be beneficial to include views with a component along the third axis. For the sake of definition, views along two axes will be referred to stereo views, while views that include a component of the third axis will be referred to as cross views, since they intersect the planer stereo views.

Reference is further made to FIGS. 4A-4F, which schematically illustrate stereo views and cross views, in accordance with embodiments of the present invention.

FIG. 4A illustrate the body 100 with a single assembly 20 arranged for viewing, for example, the heart 110. The assembly 20 is afforded with assembly oscillatory sweeping motion along the z-axis, as described by the arrow 60, and preferably first and second preferably orthogonal oscillatory lateral motions, described the arrows 80 and 90, respectively.

As seen in FIG. 4B, the assembly oscillatory sweeping motion along the z-axis, described by the arrow 60, produces views 65 in the x-y planes. The first and second orthogonal oscillatory lateral motions, described the arrows 80 and 90, augment these with additional views 65 in the x-y planes. The purpose of the first and second oscillatory lateral motions is to compensate for "dead areas," that is, structural areas and other areas that do not participate in the detection, within the assembly 20 and between the assemblies 20, so as to provide complete coverage of the body 100, by the array 25 (FIG. 1A). These motions produce views substantially in the x-y plane. It will be appreciated that there is a component of viewing in a third axis, due to the solid collection angle of the collimator 16. Yet this component is rather small.

Returning to FIG. 4A, the blocks 18 of the assembly 20 may be further afforded with block oscillatory sweeping motion, described by the arrow 70 and preferably orthogonal to the assembly oscillatory sweeping motion described by the arrow 60.

As seen in FIG. 4C, the block oscillatory sweeping motion, described by the arrow 70, produces cross views 75, which supplement views 65, by providing components of the third axis, namely, the z-axis. As illustrated in FIGS. 3A-3D, hereinabove, the views 75 may add additional information, not available or barely available in the views 65 along the x-y planes.

FIGS. 4D and 4F illustrate an alternative mode for acquiring the cross views 75. Accordingly, the dynamic camera 10 further includes assemblies 22, arranged at an angle β to the assemblies 20, and moving with an assembly oscillatory sweeping motion, described by an arrow 62, so as to provide the cross views 75.

It should be noted that the detectors of the dynamic camera 10 do not have to be arranged in arrays. In one embodiment of the present invention the detectors are scattered in front of the body so as to provide complete coverage of the body internal overall volume. The detectors can be scattered in a certain structure or in an arbitrary order.

The Position Tracker 50

The position tracker 50 is configured for providing information on the position and orientation of each detecting unit 12, with respect to the overall structure 15, substantially at all times, during the individual assembly motion.

In accordance with a preferred embodiment of the present invention, the position tracker 50 relates to software and (or) hardware that receive information from the motion provider 40 and calculate the position and orientation of each detecting unit 12, based on that information. Preferably, the calculation is performed within the control unit 55.

Alternatively, position sensors, as known, may be used for determining the position and angular orientation of each detecting unit 12.

Alternatively still, a combination of information from the motion provider 40 and position sensors may be employed.

The Timing Mechanism 30

The timing mechanism 30 associates timing information with the radioactive emission data impinging the single-pixel detectors 14 of the detecting units 12. Preferably, the timing mechanism 30 includes a single clock used for all of the single-pixel detectors 14 in the dynamic SPECT camera 10, so that timing information is synchronized for the camera as a whole. The timing information is collected at the single-pixel level, so that time binning may be performed for the emission data collected by each pixel. Exemplary methods for associating timing information with the radioactive emission data include:

1) Time stamping—Each event, impinging on a given single-pixel detector 14 at a given time is stamped with a time of detection and a pixel identification. Stamping may be performed by any manner known in the art, for example as a data packet header or footer. The time-stamped, pixel stamped radioactive emission data may be binned, per time and per pixel, by the control unit 55.

2) Time binning—In an alternate approach, timing information is provided for a cumulative count collected from each single-pixel detector 14 over a fixed time interval, for example, 0.001 seconds, 1 second, or 10 seconds, rather than for individual events. Each time bin is then stamped with a time stamp or sequential number and pixel identification. One technique for performing time binning is to insert a periodic clock pulse into the data stream. The interval between the clock pulses equals the minimum bin length. Thus, periodic pulses every 0.001 seconds may lead to bin lengths of 0.001 seconds or greater, for example, 1 second, or 10 seconds.

The timing Mechanism 30 is used by the reconstruction module in order to allow the separate reconstruction of the dynamic and static volumetric regions. The timing Mechanism 30 allows the reconstruction module to apply a time binning with a certain length on the dynamic volumetric region and a time binning with another length on the static volumetric region.

Time Scale Considerations

Dynamic studies, aimed at obtaining kinetic parameters, require the acquisition of full-reconstructed images at a rate that is no greater than about half the frequency of the sampled kinetic parameter. For example, for adult humans, blood circulates through the body at a rate of about 1 cycle per minute. Thus, sampling a process affected by blood circulation should take place at a rate of at least two samplings per minute. Preferably, sampling should be at a much greater rate, for example, 6 samplings or 10 samplings per minute—that is, about every 10 seconds or about every 6 seconds.

Additionally, based on FIGS. 5A and 5B, according to Garcia et al. (Am. J. Cardiol. 51st Annual Scientific Session, 2002), showing physiological behavior of different radiopharmaceuticals, dynamic studies for Tc-99m teboroxime are best performed within about the first 100 seconds after administration, and better still, within the first 60 seconds after administration.

Moreover, based on FIGS. 5A and 5B, the dynamic behavior of a radiopharmaceutical in the body, varies as a function of time, depending on the radiopharmaceutical and on the time elapsed since its administration. For example, myocardial perfusion of Tc-99m teboroxime shows a very steep uptake between about the first 10-15 seconds and the first 50-60 seconds, followed by a more gradual washout, after the first 60 seconds. The rate of sampling of Tc-99m teboroxime, during the first 60 seconds after administration should be adjusted to the very steep uptake, for example, a sampling rate of every second. For radiopharmaceutical with a slower dynamic behavior, a slower rate may be sufficient.

It will be appreciated that a dynamic analysis requires precise knowledge of the time of administration.

Obtaining the Time of Administration of a Radiopharmaceutical

As noted hereinabove, precise knowledge of the time of administration of a radiopharmaceutical is important both in order to evaluate physiological processes made visible by the radiopharmaceutical, with respect to the time of the radiopharmaceutical's entry to the body and in order to perform the evaluation at an optimal period, with respect to the radiopharmaceutical's cycle in the body.

There are several methods for acquiring precise knowledge of the time of administration of the radiopharmaceutical, as follows:

1. providing communication means between an administration device, for example, a syringe or an IV device, and the dynamic SPECT camera 10, and communicating the precise time of administration, vis-a-vis a clock, by the administration device to the dynamic SPECT camera 10. This method may be employed for example, when administration takes place when the patient is positioned at the dynamic SPECT camera 10, for imaging.

2. providing communication means between the administration device, the dynamic SPECT camera 10, and a third unit, for example, a control system or a hospitals ERP system, communicating the precise time of administration, vis a vis a clock, by the administration device to the third unit, and reporting the precise time of administration by the third unit to the dynamic SPECT camera 10. This method may be employed for example, when administration takes place at a different location than the imaging station.

3. allowing the dynamic SPECT camera 10 to image the site of administration, for example, the arm of the patient, while administration takes place, while employing the timing mechanism 30 of the dynamic SPECT camera 10. A marker, for example, a line of radioactive ink may drawn, for example, on the patient's arm or on the administration device, for defining the time of administration as the time the radiopharmaceutical first crosses the marker. Alternatively, observing a flow of the radiopharmaceutical in the administration device or in the patient's vein may be used to determine the time of administration.

4. Observing a transparent administration device, for example, with a video camera, associated with a clock, may be employed for defining a time of administration based on the radiopharmaceutical distribution in the administration device, or based on the time the radiopharmaceutical first crosses a marker, visible by the video camera. Communication between the video camera and the dynamic SPECT camera 10, or between the video camera, the dynamic SPECT camera 10, and a third unit will provide the information to the dynamic SPECT camera 10.

In accordance with embodiments of the present invention, the administration may include various administration profiles, for example, bolus, continuous drip, or sinusoidal.

Spatial and Temporal Resolution

In order to meet the time scale considerations, described hereinabove, the dynamic SPECT camera 10 according to embodiments of the present invention is designed at least for acquiring a tomographic reconstruction image of about 15×15×15 cubic centimeters, which is approximately the volumetric region of a heart, at a predetermined spatial resolution of at least 10×10×10 cubic millimeters, at an acquisition time no greater than about 30 seconds. Preferably, the acquisition time is no greater than about 10 seconds, and more preferably, the acquisition time is no greater than about 1 second.

Additionally, the spatial resolution of the tomographic reconstruction image may be at least 7×7×7 cubic millimeters, or better yet, at least 4×4×4 cubic millimeters, or better still, at least 1×1×1 cubic millimeters.

Anatomically Varying Time-Bin Lengths

As discussed in the background section, the time binning is needed in order to generate a clear imaging of a dynamic organ, such as the heart, or a section thereof. Though the time binning allows the acquisition of a clear image of the heart, it has at least one major disadvantage. The reconstruction of the image using time binning requires high computational throughput. Thus, binning images of the input overall volume may provide a clear imaging of the heart however have high computational throughput. Reconstruction using anatomically varying time-bin lengths can be used to reduce to computational throughput of the time binning.

While some body organs, such as the kidney, the lung, or the liver, are relatively static, so as to enable imaging of a period of time that allows acquiring a statistically significant number of counts, the heart moves relatively rapidly, with about 80-100 beats per minute, on the average. In one embodiment of the present invention, as the static region does not have to be gated to provide a clear imaging, only the dynamic region that preferably contains the heart is gated. In such an embodiment, fewer voxels are gated and therefore the computational complexity is reduced.

In such an embodiment, different areas in the body can be gated in a rate that is adjusted to according to a respective level of activeness. For example, the heart that has high level of activeness can be gated using a large number of bins, the visceral background, which is relativity static, is gated using one of two bins, and the stomach, that have higher level of activeness than the visceral background but lower level of activeness than the heart is gated using a limited number of bins.

As described below, performing gated image reconstruction using anatomically varying time-bin lengths improves the reconstruction quality, reduces the reconstruction time, or both. The improvement is an outcome of a reduction in the needed computational resources.

Reference is now made to FIGS. 15 and 16, which are respectively a schematic isometric view of the input overall volume 1001 segmented into dynamic volumetric region and static volumetric regions 1003, 1002, as depicted in FIG. 14, and a schematic cross-sectional view of the segmented input overall volume 1001A taken along the lines Ill-Ill, according to one embodiment of the present invention.

As described below a radioactive emission image of the input overall volume 1001 is segmented into a non-gated region, which includes non-gated voxels, in accordance with the static volumetric region 1002, and to a gated region, which includes gated voxels, in accordance with the dynamic volumetric region 1003. Preferably, the dynamic volumetric region 1003 is adjusted to delimit a dynamic organ, such as the human heart that is schematically represented by a hollow sphere 1004. Preferably, the dynamic volumetric region 1003 is larger than the apparent volumetric region of the heart 1004 to account for segmentation errors. It should be noted that the dynamic volumetric region 1003 may be adjusted to contain other human and animal internal organs such as the stomach. In FIG. 16, the hatched region 1003A represents the cross-section of the dynamic volumetric region 1003 and the annular crosshatched region 1004A schematically represents a cross-section through the heart muscle of the heart 1004. The region 1002A represents a cross section of the static volumetric region 1002.

It should be noted that the cubical shape of the dynamic volumetric region 1003 and the static volumetric region 1002 are not obligatory and the segmentation to regions may be performed using differently shaped volumetric regions. Preferably, the dynamic and the static volumetric regions 1003, 1002 have several non-connected parts. For example, the dynamic volumetric region 1003 may be a spherical volumetric region, an ellipsoid of revolution, an ellipsoid with a hole that represents the blood inside the heart, a cylindrical volumetric region or any other type of suitable regularly shaped or non-regularly shaped volumetric region. Preferably, the dynamic volumetric region 1003 comprises non-connected components, which may be referred to as sub-volumetric regions.

Reference is now made jointly to FIG. 15, previously described, and to FIG. 17, which is a flowchart that depicts a method for reconstruction an input overall volume using anatomically varying time-bin lengths, according to one embodiment of the present invention.

During the first step, as shown at 1301, radiation emitted from the input overall volume 1001 is captured by the SPECT detectors and recorded, as described above. The captured radiation is used to generate a set of gated images, which are used to overcome distortions such as motion artifacts. As described above, each gated image is generated by a photon counting that takes into account the portion of the heart contraction cycle within which a photon is measured. The number of photons hitting the detector within a specific integration time is calculated and used as raw data, which may be referred to as datasets.

Then, as shown at step 1302, the captured datasets are firstly used in an initial reconstruction process in which an initial estimation image is generated. Preferably, a non-gated reconstruction is used to provide a reconstruction that estimates the static intensity distribution.

In the following step, as shown at step 1303, the initial estimation image is segmented to a gated region and a non-gated region that respectively define the boundaries of the dynamic and static volumetric regions.

The segmentation of the input overall volume 1001 to dynamic and static volumetric regions 1003, 1002 is performed using a suitable image segmentation method or process.

Preferably, the input overall volume 1001 is further segmented to one or more other segments such as the liver. Such segments may be joined to the dynamic or to the static volumetric regions 1003, 1002 according to the nature of the activity level of the segment. For instance, the liver may be joined to the static volumetric region.

The segmentation to static and dynamic volumetric regions may be performed using a number of possible methods. In one embodiment of the present invention, a system user marks the boundaries of the dynamic volumetric region that comprises the gated voxels. In such an embodiment, the reconstructed image is displayed on a screen of a user interface that allows the system user to delimit the dynamic volumetric region. Though the captured image is blurry, as it is not gated, it provides the system user a perceptual image of the outlines of the internal organs in the input overall volume, including the heart, the liver, the spleen, the kidneys, and the aorta. In such an embodiment, the system user segments the captured image to gated and non-gated regions according to their level of activity, thereby defines the gated and non-gated regions. Preferably, the system user segments the heart as a non-gated region.

In one embodiment of the present invention, the segmentation is based on a voxel value threshold that reflects a certain percentage of the maximal reconstruction value. In such an embodiment, voxels of the reconstructed image having a value above the threshold are presumed to be voxels that depicts the heart and tagged as gated voxels of the dynamic volumetric region and voxels of the input overall volume 1001 having a value below the threshold are tagged as non-gated voxels of the static volumetric region. Preferably, regions in the captured image are segmented according to predefined characteristics. For example, the liver region, which can be characterized as a very large segment residing in the lower part of an image that depicts the thorax, is identified and segmented as a static volumetric region 1003 or a section thereof.

Preferably, the predefined threshold is defined according to the radiation intensity of the visceral background of the input overall volume 1001. In such an embodiment, the radiation intensity of the visceral background is estimated before the segmentation process. Such an initial estimation can be performed using median or linear filters such as Gaussian and moving average filters. Each one of the voxels of the input overall volume 1001 with a value that is well above the estimated background radiation is tagged as a gated voxel. Each one of the voxels of the input overall volume 1001 with a value, which is below the estimated background radiation, is tagged as a non-gated voxel.

In one embodiment of the present invention, the segmentation is performed according to morphological segmentation methods that adjusted according to the volumetric characteristics of the segmented volumetric regions. For example, for the heart that has convex faces can be segmented using top hat transform.

In one embodiment of the present invention, the segmentation is performed according to the growing rate of regions of the input overall volume 1001. In such a manner, regions such as the heart may be indented. In one embodiment, voxels having high growing rate are clustered as a group of voxels that depicts the heart.

In one embodiment of the present invention, the faces of the heart are identified. Such identification may be performed using an objective function with two parts. One part of the objective function is dependent on the organ border smoothness alone and the other part is dependent on the edge strength near a defined border, see M. Kass, A. Witkin, and D. Terzopoulos. Snakes: active contour models, International Conference on Computer Vision, pages 259-268, 1987, which is incorporated in its entirety by reference into the specification.

For clarity, $Z_{dyn}(u)$ and $Z_{stat}(u)$ respectively denotes the dynamic volumetric region and the static volumetric region of the captured image. The dynamic and static volumetric regions respectively define the boundaries of gated and non-gated regions in the radioactive emission image that depicts the input overall volume. It should be noted that though only two volumetric regions are exemplified hereinbelow, the overall volume may be segmented according to any number of volumetric regions such as three volumetric region, four volumetric region, ten volumetric region etc.

Preferably, after the gated and non-gated regions of the radioactive emission image have been segmented according to the dynamic and static volumetric regions, different resolutions are used for gated and non-gated voxels. In such an embodiment, the computational load of the reconstruction may be reduced by using large voxels with a low resolution in the static volumetric region 1002 and small voxels in the gated volumetric region.

Preferably, various morphological methods, such as, dilation, closing and the like are used after the initial segmentation to expand the dynamic volumetric region 1003. The broadening of the dynamic volumetric region 1003 is done in order ensure that if the segmentation has been made according to an organ in a contracted state, the dynamic volumetric region 1003 still encompasses the organ in an expanded state.

After the static and dynamic volumetric regions have been segmented during the initial reconstruction process, time binning of the dynamic volumetric region of the input overall volume is performed and a separate reconstruction of the static and the dynamic volumetric regions is enabled. As shown at 1304-1306, the reconstruction is based on an iterative process in which the time binning of gated images of the dynamic volumetric region is enabled.

For clarity, $I_0(u)$ denotes an input image I, which is preferably constant, that depicts $u \in U$ voxels, t denotes a certain detector, g denotes a certain gate in a set of G gates, such as 8, 16, and 24, $\phi_t(u)$ denotes a standard functional matrix that depicts the detection probability of a photon emitted from location $u \in U$ to be detected by detector t, $s_t$ denotes the sensitivity of the detector t, $T_t^g$ denotes the integration time of detector t for gate g, $I^g(u)$ denotes a set of G gated reconstructed images, $y_t^g$ denotes the number of photons that are emitted from voxel u and detected in detector t at gate g.

$T_t$ denotes the integration time of detector t and calculated as follows:

$$T_t = \Sigma_g T_t^g$$

$I_{stat}(u)$ and $I_{dyn}^g(u)$ respectively denote static and dynamic region images, where $I_{stat}(u)$ and $I_{dyn}^g(u)$ are mutually exclusive as $I_{stat}(u) \cdot I_{dyn}^g(u) = 0$, $\forall u$.

$Z_{dyn}(u)$ and $Z_{stat}(u)$ respectively denote static and dynamic regions in I, as defined in the aforementioned segmentation process. Preferably, $Z_{dyn}(u)$ and $Z_{stat}(u)$ are defined as follows:

$$Z_{dyn}(u) = \begin{cases} 1, & u \in \text{dynamic region} \\ 0, & \text{otherwise} \end{cases}$$

$$Z_{stat}(u) = 1 - Z_{dyn}(u)$$

Preferably, before the input overall volume I is iteratively reconstructed, few preliminary sub-steps are taken. During the first sub-step, stat $I_{stat}(u)$ and $I_{dyn}^g(u)$ are initialized as follows:

$$I_{stat}(u) = I_0(u) \cdot (1 - Z_{dyn}(u))$$

$$I_{dyn}^g(u) = I_0(u) \cdot Z_{dyn}$$

Preferably, if $Z_{dyn}(u) = 0$, the size of $I_{dyn}^g(u)$ is reduced.

As described above, $Z_{dyn}(u)$ and $Z_{stat}(u)$, which respectively confine the static and dynamic volumetric regions, are defined at step 1302.

During the second sub-step the scale is calculated as follows:

$$\text{scale}_{O.S.}^g(u) = \Sigma_{t \in O.S.} S_t \cdot T_t^g \cdot \phi_t(u)$$

$$\text{scale}_{O.S.}(u) = \Sigma_g \text{scale}_{O.S.}^g(u)$$

After the preliminary steps have been completed, the reconstruction of the input overall volume according to time binning process commences. Preferably, during the reconstruction $I_{stat}(u)$ and $I_{dyn}^g(u)$ are calculated for each voxel $u \in U$ in the input overall volume.

During each iteration of the time binning process, as shown at 1305, the gated and non-gated regions that represent the static and dynamic images $I_{stat}(u)$, $I_{dyn}^g(u)$ are updated. The updating of the regions is calculated according to a deviation between the number of photons that has been detected by the SPECT detectors and an estimation of this number, as described below. During each one of the iterations, the gated voxels of the dynamic volumetric region are binned according to the number of gates and the non-gated voxels are binned only once. As the non-gated voxels are binned only once, the computational complexity of the process is relatively low. The separation between the static and dynamic volumetric regions improves the computational efficiency and reduces the statistical variance.

In particular, in order to calculate $I_{stat}(u)$ and $I_{dyn}^g(u)$, a number of sub-iterations take places. First, $\hat{y}_{stat,t}$ is calculated as follows:

$$\hat{y}_{stat,t} = s_t T^g \Sigma_u \phi_t(u) I_{stat}(u)$$

Where $\hat{y}_{stat,t}$ denotes an estimation of the number of photons that are emitted from the voxels $u \in U$ and detected by detector t, wherein values of voxels from the dynamic volumetric region are zeroed. It should be noted that the sensitivity parameter of and the integration time of detector t are taken into account at some stage in the calculation.

Then, $\hat{y}_{dyn,t}^g$ is calculated as follows:

$$\hat{y}_{dyn,t}^g = s_t T_t^g \Sigma_u \phi_t(u) I_{dyn}^g(u)$$

Where $\hat{y}_{dyn,t}^g$ denotes an estimation of the number of photons that are emitted at gate g from voxels $u \in U$ and detected in detector t, wherein values of voxels from the static volumetric region are zeroed. It should be noted that the sensitivity parameter and the integration time of detector t for gate g are taken into account at some stage in the calculation.

$\hat{y}_t^g$ is calculated according to $\hat{y}_{dyn,t}^g$ and $\hat{y}_{stat,t}$, as follows:

$$\hat{y}_t^g = \hat{y}_{stat,t} + \hat{y}_{dyn,t}^g$$

Where $\hat{y}_t^g$ denotes an estimation of the number of photons that are emitted from a certain voxel $u \in U$ and detected by detector t at gate g. It should be noted that unlike the calculation of $y_t^g$, the calculation of $\hat{y}_t^g$ does not take into account the integration time and the sensitivity factor.

Then, for each gate g, the numerator $\text{num}^g(u)$ is evaluated as follows:

$$\text{num}^g(u) = \sum_t \frac{y_t^g}{\hat{y}_t^g} (s_t T_t^g \phi_t(u) - 1)$$

Where $\text{num}^g(u)$ sums the deviation between the number of photons that are emitted from voxel u and detected in detector t at gate g and the estimation thereof of all the detectors, wherein the sensitivity and the integration time of each detector t are taken into account. It should be noted that the calculation can be directly extended to an ordered sets method or any of its variations by summing the deviation over subsets of the group of detectors.

Based thereupon, the numerator $\text{num}(u)$ is evaluated as follows:

$$\text{num}(u) = \Sigma_g \text{num}^g(u)$$

Where $\text{num}(u)$ is a sum of all the numerators that are evaluated for every $g \in G$.

$I_{stat}(u)$ and $I_{dyn}^g(u)$ are updated according to the calculation of the aforementioned scales and numerators, as follows:

$$I_{stat}(u) = I_{stat}(u) + \frac{\text{num}(u)}{\text{scale}(u)} \cdot I_{stat}(u)$$

$$I_{dyn}^g(u) = I_{dyn}^g(u) + \frac{\text{num}^g(u)}{\text{scale}^g(u)} \cdot I_{dyn}^g(u)$$

The updated $I_{stat}(u)$ and $I_{dyn}^g(u)$ are stored and used during the next iteration, as shown at step 1306. Steps 1303-1306 are repeated iteratively until the reconstruction of the input overall volume has reached a desired quality.

Preferably, in order to determine whether the reconstruction has reached a desired quality, as shown at 1306, the number of gated voxels with activity above a predefined threshold is checked. For example, the number of gated voxels with activity level that is in the range between the maximal gated voxel intensity value and 20% therefrom is checked.

When the time binning process has been completed, as shown at 1306, a gated reconstructed image can be generated as follows:

$$I^g(u)=I_{stat}(u)+I_{dyn}^g(u)$$

Reference is now made to FIG. 18, which is a graphical representation of one dimensional vector $I_c$ of voxels that represents the reconstruction of the input overall volume. Preferably, all the non-gated voxels $I_{stat}(u)$ that represent static regions of the input overall volume U are arranged 1101 first within the vector $I_c$. The non-gated voxels are followed 1101 by gated voxels that comprise a set of different frames in a consecutive order that are arranged in clusters. Each cluster represents the dynamic volumetric region of the input overall volume at a certain frame. The frames are denoted by 1102A, ..., 1102G. The frames can be arranged in any predefined order.

As described above, $\phi_t(u)$ is a standard functional matrix that depicts the detection probability of a photon emitted from a voxel $u \in U$ to be detected by a detector t. Since $\phi_t(u)$ is a sparse matrix, the number of math operations can be reduced by defining $\phi_t^g(u)$ which is zero wherever $I_{dyn}^g(u)$ is zero.

Reference is now made jointly to FIG. 15, previously described, and to FIG. 19, which is a flowchart that depicts another method for reconstruction an input overall volume using anatomically varying time-bin lengths, according to another embodiment of the present invention. In the method depicted in FIG. 19, the static region is estimated only once according to the initial reconstruction process step.

The method depicted in FIG. 19 is based on the assumption that the non-gated static region equals to the average of the gated dynamic region images reconstructions. Though the assumption is not accurate, it is expected to be sufficient for the reconstruction of the input overall volume. As the static region is calculated only once, the memory usage and the computational complexity decrease.

Steps 1301 and 1302 are as depicted in FIG. 17. During steps 1301 and 1302 the first step I(u) is obtained. Then, as shown at 1310 and 1311, I(u) is segmented to current and static regions, preferably according to the following equations:

$$I_{stat}(u)=I(u)\cdot(1-Z_{dyn}(u))$$

$$I_{dyn}^g(u)=I(u)\cdot Z_{dyn}(u), \text{ for each } g \in G$$

In order to reduce the computational complexity of the following iterative process, $\hat{y}_{stat,t}$ is evaluated in advance as follows:

$$\hat{y}_{stat,t}=s_t T^t \Sigma_u \phi_t(u) I_{stat}(u)$$

The previously described method uses the standard functional matrix $\phi_t(u)$ that is a representation of the probability to detect a photon emitted from location $u \in U$ by a detector t. The calculation of $\phi_t(u)$ requires high computational complexity as all the voxels of the input overall volume have to be calculated. In order to reduce the computational complexity a standard functional matrix that is limited to dynamic voxels is used $\phi_{t,dyn}(u)$. The limited standard functional matrix is defined as follows:

$$\phi_{t,dyn}(u) = \begin{cases} \phi_t(u), & u \in \text{dynamic region} \\ 0, & \text{otherwise} \end{cases}$$

Then, for each $g \in G$, the scale on the dynamic region $scale^g(u)$ is evaluated, as described above.

During the following step, as shown at 1312, the dynamic volumetric region $I_{dyn}^g(u)$ is calculated. In particular, in order to calculate $I_{dyn}^g(u)$, a number of sub-iterations take place. First, $I_{dyn}^g(u)$ is calculated using $\phi_{t,dyn}(u)$ as follows:

$$\hat{y}_{dyn,t}^g=s_t T_t^g \Sigma_u \phi_t(u) I_{dyn}^g(u)$$

Then based on $\hat{y}_{dyn,t}^g$ and $\hat{y}_{stat,t}$ that has been calculated in the step 1310, $\hat{y}_t^g$ is calculated as follows:

$$\hat{y}_t^g = \hat{y}_{stat,t} + \hat{y}_{dyn,t}^g$$

Where $\hat{y}_t^g$ denotes an estimation of the number of photons that are emitted from a certain voxel $u \in U$ and detected by detector t at gate g. It should be noted that unlike $\hat{y}_{dyn,t}^g$, $\hat{y}_{stat,t}$ is not recalculated during the iterative process.

Then, for each gate g, the numerator $num^g(u)$ is evaluated as follows:

$$num^g(u) = \sum_t \frac{y_t^g}{\hat{y}_t^g}(s_t T_t^g \phi_t(u) - 1)$$

Based on the calculation of the scale that has been calculated before the iterative process and the numerator that is calculated according to radiation emitted from the dynamic region and captured by the detectors, $I_{dyn}^g(u)$ is updated as follows:

$$I_{dyn}^g(u) = I_{dyn}^g(u) + \frac{num^g(u)}{scale^g(u)} \cdot I_{dyn}^g(u)$$

The updated $I_{dyn}^g(u)$ is stored and used during the next iteration, as shown at step 1316.

Then, as shown at 1313, the input overall volume is reconstructed using the updated dynamic region and the static region. As shown at 1314, steps 1311-1314 are repeated iteratively until the reconstruction of the input overall volume has reached a desired quality. In the end of each on of the iterations, the dynamic region is updated, as described above.

When the iterative process has been completed, as shown at 1314, a gated reconstructed image can be generated as follows:

$$I^g(u)=I_{stat}(u)+I_{dyn}^g(u)$$

The gated voxels in the dynamic volumetric region 1003 may represent ischemic regions of the heart. The radiation reflected from such ischemic regions may have specific radiation patterns such as a center with low radiation. Thus, such regions can be reconstructed using morphological closing methods or by taking into account the typical shape of the heart (one way is by fitting an ellipsoid to the edges in the image, but other methods may also be used).

Reference is now made to FIG. 20, which is a graphical representation of a position of two selected sub-regions in two sequential frames. As described above, the reconstruction of the dynamic volumetric region is based on time binning of a number of consecutive frames that depict a dynamic organ such as the heart. As each frame is based on a number of gated images, it has high computational load.

In one embodiment of the present invention, the set of frames is a set of sequential images that depict the heart. As all the frames depict the same input overall volume and as the heart has an expected movement pattern, we can use one or more frames to estimate another. In such a manner, fewer frames are calculated and therefore the computational complexity of the reconstruction decreases. Preferably, during the time binning, geometrical information from one or more prior frames assist in the reconstruction of subsequent one or more frames. Such geometric prior methods are generally well known and therefore, are not described here in greater detail.

For example, FIG. 20 depicts two sequential frames, frame i−1 1054 and frame i 1056, which are taken from a sequence of M frames. The sub-regions 1057A and 1059A in frame 54 schematically represent two different regions of the heart 1055. The regions 1057B and 1059B of frame 1056 schematically represent the respective positions of regions 1057A and 1059A in frame 1056. The change in the positions is an outcome of the movement of the heart 1055. The vector T1 represents the movement of the region 1057B relative to the region 1057A and the vector T2 represents the movement of the region 1059B relative to the region 1059A. T1 and T2 can be used to estimate the position of additional one or more frames in some of the embodiments of the present invention. See, Green P, Bayesian Reconstructions from Emission Tomography Data using a Modified EM Algorithm, IEEE Tran. On medical imaging vol. 9 No. 1, March 1990, pp. 84-93 and Fessler J, 2004 NSS/MIC statistical image reconstruction short course notes entitled "Statistical Methods For Image Reconstruction", www(dot)eecs(dot)umich(dot)edu/fessler/papers/files/talkIO4/mic(dot)notes(dot)Pdf which are incorporated in their entirety by reference into the specification. Preferably, voxels that represent the same anatomical location are stated to be alike. Therefore, voxels from different frames that represent the same anatomical location can form a clique, or a neighborhood, as defined by the Gibbs prior equation. The strength of applying such a geometric prior may be depended on the movement amplitude and on the gate phase.

Dynamically Varying Time-Bin Lengths

There are times when dynamically varying time-bin lengths are desired. For example, Tc-99m-teboroxime has an uptake curve (FIG. 5B) which is very steep during the uptake and which becomes less so during the washout. Thus, different time-bin lengths may be desired for different portions of the Tc-99m-teboroxime uptake curve. Similarly, different radiopharmaceuticals have different uptake curves, and dedicated time-bin lengths may be desired for each radiopharmaceutical, and for different portions of their respective uptake curves. Moreover, the cardiac RR cycle has very steep periods, during the rise and fall of the R peak (FIG. 5F), followed by periods that are nearly flat as a function of time. Again, time bin lengths of different durations may be employed for the different portions of the RR cycle. Furthermore, while the actual region of interest, for example, the heart, requires imaging at a very high level of accuracy, adjacent regions, for example, the chest muscle, may be of lesser interest, and may be viewed at time bins of greater lengths. Additionally, continuous acquisition mode may require shorter time-bin lengths than stop and shoot mode.

For example, the actual rise and fall of the R peak may be gated at time bins of 10 milliseconds, while the nearly leveled U-wave may be gated at 100 milliseconds. Similarly, while the heart muscle may be gated at an average time bin of 50 milliseconds, the adjacent chest muscle may be gated at time bins of 1 second and longer. It will be appreciated that other values may similarly be employed.

In accordance with embodiments of the present invention, a lookup system of recommended time-bin lengths may be provided, for specifying recommended time-bin lengths as functions of one or more of the following:

a specific region of interest;
an administered radiopharmaceutical;
time elapsed since the administration of the radiopharmaceutical;
cardiac state with respect to an RR cycle;
a view of the detecting unit 12, with respect to the region of interest;
patient general data; and
data acquisition mode.

The lookup system may be, for example, tables or curves.

Thus the dynamic SPECT camera 10 may be configured for time binning at dynamically varying time-bin lengths, by providing communication between the timing mechanism 30 and the lookup system, wherein the timing mechanism is configured for selecting a recommended time-bin length from the lookup system, for each time bin.

Clearly, if the input image has been segmented to gated and non-gated regions, as described in above, only the gated region is gated at time bins at dynamically varying time-bin lengths.

Dynamically Varying Spectral Bins

It is sometimes of value to image only a specific spectral bin so as to eliminate scatter or contributions from other radiopharmaceuticals. Additionally, it may be of value to image several spectral bins simultaneously, for different radiopharmaceuticals, wherein different groups of detecting units are dedicated to different spectral bins.

Thus, the dynamic SPECT camera 10 may be configured for dynamically determining a spectral energy bin for each detecting unit 12, as follows:

providing a spectral selection mechanism 56 (FIG. 1A), for enabling a selection of a spectral energy bin to be used for each detecting unit 12, independently from the other detecting units 12; and a lookup system of recommended spectral energy bin values, as functions of at least one of a specific region of interest, an administered radiopharmaceutical, time since the administration of the radiopharmaceutical, a view of the detecting unit with respect to the region of interest, and patient's details;

wherein the spectral selection mechanism 56 is further configured for dynamically determining the spectral energy bin for each detecting unit, as functions of the specific region of interest, the administered radiopharmaceutical, the time elapsed since the administration of the radiopharmaceutical, the view of the detecting unit with respect to the region of interest, and patients' details, from the lookup system.

The spectral energy bin is designed to include a primary photon energy ±10%, or the primary photon energy ±7%, or the primary photon energy ±5%.

Additionally, at least two radiopharmaceuticals may be administered and viewed by different groups of detecting units, each group being configured for a different spectral energy bin, so as to view each radiopharmaceutical in the same region independently of the other radiopharmaceutical.

The spectral selection mechanism may be a hardware unit or software.

The spectral selection may be performed during data acquisition, or later.

Intracorporeal Dynamic SPECT Camera

Referring further to the drawings, FIGS. 6A-6I describe the dynamic SPECT camera 10 as an intracorporeal dynamic SPECT camera 10, which includes a single assembly 20, preferably configured for oscillatory sweeping motion around its longitudinal axis—the z axis, as described by the arrow 60. The blocks 18 may be further configured for oscillatory sweeping motion in an orthogonal direction, as described by the arrows 70. An end block 18' may be further configured for motion, for example, as described by the arrow 70'. It will be appreciated that other motions are similarly possible, for example, oscillatory lateral motions, or rotational motions. For example, the arrow 90 describes the oscillatory lateral motion along the z axis of the assembly 20.

An ultrasound transducer 45 may be included with the intracorporeal dynamic SPECT camera 10.

Other features of the intracorporeal dynamic SPECT camera 10 are as described for the dynamic SPECT camera 10 of FIGS. 1A-1D.

FIG. 6A illustrates the intracorporeal dynamic SPECT camera 10 as a single rigid unit, for example, for rectal or vaginal insertion. FIG. 6C illustrates the intracorporeal dynamic SPECT camera 10 as having an incorporeal portion 44, an extracorporeal portion 42 and a cable 46, for example, for insertion to the esophagus.

Figure 6I:
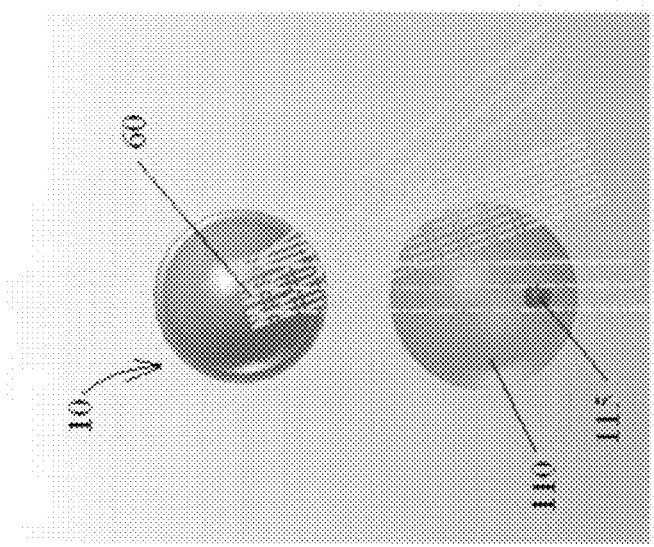
Figure 6H:
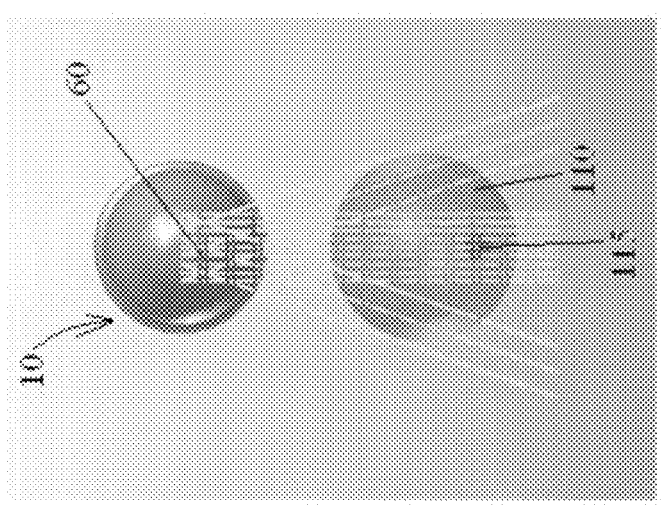
Figure 6G:
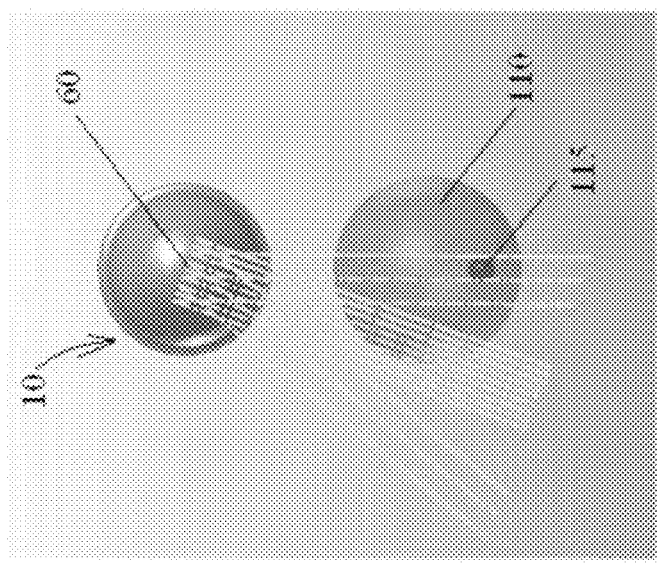

FIGS. 6F and 6E illustrate motions of the blocks 18, as described by the arrows 70. FIGS. 6F-6I illustrate motion of the assembly 20, as described by the arrow 60.

Reconstruction with Object Implantaion

As described above, the reconstruction of the radioactive emission image is based on datasets that have been acquired from a certain overall volume, such as the thorax, with objects having known volume and structure, such as the heart. As the reconstructed volumetric region has a known structure and comprises organs with estimated structure, relative location, and volume, the throughput of the reconstruction can be reduced.

The reconstruction process is an iterative process. During each step, the reconstruction of the overall volume and one or more volumetric regions thereof are being refined. Preferably, one or more object models, which are defined according to an image, such as a CT or an MRI image, an anatomical atlas, or other accurate reconstructions of respective objects, are used to improve and enhance the reconstruction process.

Object implantation proceeds as follows: after a few iterations, which provide a general idea of both:
i. the location and general shape of an organ in question, such as a heart, lungs, a stomach, visceral background elements, etc.; and
ii. an estimation of the expected number of photons that are emitted from different portions of the organ in question, the general shape and photon counts of the organ in question are replaced by an implanted model, based on a CT image, an MRI image, an anatomical atlas, or the like, thereby providing both:
   i. a better definition of edges between the organ in question and the surroundings; and
ii. some analytical evaluation of the expected number of photons that are emitted from different portions of the organ in question, based on the first few iterations, for example, given that the organ is a heart, an average count values for the blood and for the heart muscle, respectively, may be used, based on first few iterations, for the different areas of the model. It will be appreciated that an anatomical construction of voxels may be employed with the voxel implantation.

In this manner, object implantation improves the reconstruction that is based on counting statistics.

It will be appreciated that object implantation may be employed once or several times during the reconstruction process, each time, providing a better starting point for the next iteration.

Object implantation comes to solve the problem that during the first steps of the reconstruction, a blurry radioactive emission image of the overall volume is received, as described above. An organ, such as the heart, can be identified in the blurry radioactive emission image according to a cluster of voxels with expected values in an expected relative position. The value of voxels in such a cluster can be adjusted or changed according to a respective object model. For example, if after a certain number of iterations a cluster of voxels in the upper right section of the overall volume has voxels with a certain average expected value, the cluster can be identified as the heart. As it is known that the number of photons, which are emitted from voxels of the heart is relatively high, the value of voxels in the related cluster are adjusted or changed to have relatively high values, according to the object model. In such a manner, the actual shape of the heart can be reconstructed more efficiently.

Reconstruction Using a Minimal Number of Gray Levels

Strictly speaking, variations in radioactive emission activity between different voxels can be infinite, one voxel showing a photon count of 17,584/for a given time period, and another, a photon count of 18,900/for the given time period. Yet, to a doctor, interested in identifying background muscles, heart muscles, or blood, and further, interested in differentiating between healthy heart muscle, ischemic muscle, and dead tissue, a few levels of gray, for example, between 5 or 10 levels or gradations of gray, may be sufficient. Thus, reconstruction need not be carried out in order to evaluate an accurate photon count per voxel, but merely to determine the level of gray, from amongst 5-10 levels of gray, per voxel.

As described above, the reconstruction of the radioactive emission image is based on datasets that have been acquired from a certain overall volume. The reconstruction is performed by summing up the photons that are emitted from voxels of the overall volume. The sums of the emitted photons are translated to gray level values, which are used to reconstruct the radioactive emissions image. Preferably, in order to determine whether the reconstruction has reached a desired quality, the number of voxels with activity above a predefined threshold is checked. For example, the number of voxels with activity level that is in the range between the maximal voxel intensity value and 20% therefrom is checked. Other criteria may be determined is order to evaluate whether the reconstruction has reached a desired quality. Threshold values are preferably chosen empirically to yield accurate reconstruction of the overall volume. This analysis applies to gated and ungated regions, alike.

Preferably, the values of the voxels are mapped to a limited number of gray level values, such as 5, 7, 8, 9, or 10. By limiting the number of gray level values a radioactive emissions image, which is more coarsened, is generated and the computational load of the reconstruction process is reduced. Though such a limitation reduces the sharpness and the contrast level of radioactive emission image, the coarsened radioactive emission image still depicts enough information that allows a physician to identify ischemic regions in the overall volume. It should be noted that such a mapping may separately be used on one or more volumetric regions of the overall volume, preferably according to the dynamic characteristics thereof.

Image Acquisition Modes

In accordance with embodiments of the present invention, several image acquisition modes are available, as follows:

In a continuous acquisition mode, also referred to as fanning, data is acquired while the array, the assembly, or the block is in continuous motion. Continuous acquisition mode may apply also to oscillatory motions, although strictly speaking there is a momentary pause with each change of direction. This mode leads to some blurring of the data, but it does not require the array, assembly, or block to stabilize between periods of motion and periods of stationary data acquisition.

In a stop and shoot acquisition mode, incremental travels are followed by stationary acquisition intervals. This mode leads to better resolution, yet it requires a damping period, to allow the array, assembly, or block to stabilize between periods of motion and periods of stationary data acquisition, as discussed hereinbelow, under the heading, "Stability and Damping Time".

Interlacing is a fast stop and shoot acquisition mode with oscillatory motion, for example, sweeping oscillatory motion, wherein on rather than stopping at each predetermined locations, with each sweep, the odd locations are visited on a right sweep and the even locations are visited on the left sweep, or vice vera, so that each sweeping direction stops at different locations.

Prescanning relates to a fast prescan of a subject undergoing diagnosis, to identify a region-of-interest, and thereafter collect higher quality data from the region-of-interest. A prescan according to the present invention may be performed by the dynamic SPECT camera 10, preferably, with interlacing, or in a continuous mode, or by any other imaging device, including, for example, ultrasound or MRI.

Stability and Damping Time

Stop and shoot acquisition mode involves discontinuities in motion between travel and shooting modes, and at the beginning of each shooting mode, the assemblies 20 must be allowed to stabilize till vibrations are less than about ±0.25 mm, so as not to interfere with the acquisition.

Prior art SPECT cameras must allow for a damping time of about 5 seconds, but the dynamic SPECT camera 10, according to embodiments of the present invention reaches stability in about 1 second or less.

FIG. 7 schematically illustrate the assembly 20, according to embodiments of the present invention. The damping time for the assembly 20 may be described as:

$$\text{Damping Time}=C\times[(1/12)M(T^2+W^2)+MX_0^2],$$

wherein:

M is the mass of the assembly 20;
T is the thickness of the assembly 20;
W is the width of the assembly 20;
$X_0$ is the axis of rotation; and
C is a constant that depends on the braking force applied to the assembly 20.

The factor 1/12 is calculated assuming the assembly proximal end is tangential to the sweeping path.

As the damping time equation illustrates, the damping time is highly dependent on both the axis of rotation $X_0$ and the mass of the assembly 20.

In the present case, the axis of rotation is that of the sweeping motion described by the arrow 60 (FIG. 1A), which is considerably shorter than an axis of rotation around the body 100.

Similarly, the mass of a single assembly is far less than that of a conventional SPECT camera.

Possible values for the assembly 20, according to embodiments of the present invention may be:

Weight of the assembly 20≈1.5 kg.
Thickness of the assembly 20≈5 cm.
Width of the assembly 20≈7 cm.

As such, the assembly is designed with a damping time constant of under 50 msec during which vibrations amplitude subsides to under 0.25 mm.

It will be appreciated that the present example applies to both extracorporeal and intracorporeal dynamic cameras.

Stationary Dynamic SPECT Camera

It may be desired to perform imaging, especially prescanning with a stationary camera, that is without motion, for the following reasons:

1. in continuous acquisition mode, the blurring produced by the motion is eliminated;
2. in stop and shoot acquisition mode, the time spent in motion is avoided, as are the vibrations, associated with the discontinuities between the motions and the stationary intervals.

In general, a stationary camera does not provide sufficient viewing positions and detecting units, yet the camera may be specifically designed to provide those, to a desired level.

Preferably, the assemblies 20 are positioned at optimal positions prior to imaging, and imaging takes place while the camera is stationary.

Thus, in accordance with embodiments of the present invention, there is provided a stationary dynamic SPECT camera 10, which is described herein with reference to FIGS. 1A-1D. The stationary dynamic SPECT camera 10 comprises:

the overall structure 15, which defines proximal and distal ends with respect to a body;
the first plurality of the assemblies 20, arranged on the overall structure 15, forming an array 25 of the assemblies 20, each assembly 20 comprising:
a second plurality of detecting units 12, each detecting unit 12 including:
a single-pixel detector 14, for detecting radioactive emissions; and
a dedicated collimator 16, attached to the single-pixel detector, at the proximal end thereof, for defining a solid collection angle δ for the detecting unit; and
an assembly motion provider 40, configured for providing the assembly 20 with individual assembly motion with respect to the overall structure, prior to the acquisition of radioactive-emission data;
a position-tracker 50, configured for providing information on the position and orientation of each of the detecting units 12, with respect to the overall structure 15, during the individual motion,
the stationary dynamic SPECT camera 10 being configured for acquiring a tomographic reconstruction image of a region of interest while stationary, for the whole duration of the tomographic image acquisition.

Preferably, the region of interest is about 15×15 ×15 cubic centimeters, and the tomographic image may be acquired during an acquisition time of 60 seconds, at a spatial resolution of at least 20×20×20 cubic millimeter.

Additionally, the tomographic image may be acquired during an acquisition time of 30 seconds, at a spatial resolution of at least 20×20×20 cubic millimeter.

Furthermore, the tomographic image may be acquired during an acquisition time of 60 seconds, at a spatial resolution of at least 10×10×10 cubic millimeter.

Additionally, the tomographic image may be acquired during an acquisition time of 30 seconds, at a spatial resolution of at least 10×10×10 cubic millimeter.

Preferably, the structure 15 conforms to the contours of the body 100, for acquisition with substantial contact or near contact with the body.

Additionally, the assemblies 20 in the array 25 are configured to provide stereo views in a plane and cross views.

Anatomic Construction of Voxels

Anatomic construction of voxels avoids the smearing effect of a rigid voxel grid construction, where different tissue types, for example, blood and muscle, appear in a same voxel. This is important especially for perfusion studies, where the perfusion of blood into the tissue is sought.

Reference is now made to FIGS. 8A and 8B, which schematically illustrate a rigid voxel grid construction and an anatomic construction of voxels, respectively, in accordance with the present invention.

FIGS. 8A and 8B illustrate a heart 200, having atria 202 and 204, chambers 206 and 208, and a muscle 218.

As seen in FIG. 8A, a rigid voxel construction 202 causes smearing of the different tissue types. However, as seen in FIG. 8B, blood and muscle tissues are anatomically divided into different voxels, allowing an accurate study of perfusion. The atria and chambers are divided into an anatomic voxel system 222, or to an anatomic voxel system 224, while the muscle is divided into a relatively coarse voxel system 226, or to a finer voxel system 228, as desired. It will be appreciated that the anatomic voxels may vary in volumetric region. For example, since ischemia is not relevant to the atria and chambers, they may be divided into coarse voxels, while the heart muscle may be divided into fine voxels.

As further seen in FIG. 8B, the rigid voxel construction 202 may still applied to the surrounding chest muscle.

It will be appreciated that parametric equations, such as F(1) and F(2) may be created and used in the construction of the anatomic construction of the voxels.

The following describes methods for obtaining the anatomic construction of voxels.

A first method for the anatomic construction of voxels includes:

providing a structural image of a region of interest, such as a heart;

constructing an anatomic system of voxels, for the region of interest, in which voxel boundaries are aligned with boundaries of structural objects of the region of interest, based on the structural image;

performing radioactive-emission imaging of the region of interest, utilizing the anatomic system of voxels; and performing reconstruction of the radioactive-emission imaging, utilizing the anatomic system of voxels.

Preferably, the structural image is provided by a structural imager, selected from the group consisting of 2-D ultrasound, 3-D ultrasound, planner x-rays, CT x-rays, and MRI.

Additionally, the structural imager is co-registered to a radioactive-emission imaging camera which performs the radioactive-emission imaging.

Moreover, attenuation correction of the radioactive-emission imaging may be performed, based on the structural image.

Furthermore, the structural image and the radioactive-emission image, constructed with the anatomic voxels, may be displayed together.

Alternatively, the structural imager is not co-registered to a radioactive-emission imaging camera which performs the radioactive-emission imaging, and further including corrections for misregistration.

Alternatively still, the structural image is provided from a lookup system, which is preferably corrected for patient's details.

It will be appreciated that the anatomic construction of voxels may be based on fitting the boundaries of the structural objects to parametric equations and utilizing the parametric equations in the constructing of the anatomic system of voxels.

Additionally, the anatomic system of voxels includes voxels of varying volumetric regions, depending on their anatomic position and relevance.

Furthermore, the method includes time binning of the radioactive emissions to time periods not greater than substantially 30 seconds, or not greater than substantially 10 seconds, or not greater than substantially 1 second.

Additionally, the anatomic system of voxels includes voxels of varying volumetric regions, depending on the relevance of their dynamic activity.

An alternative method for the anatomic construction of voxels includes, relates to the use of the radioactive emission imaging itself for the anatomic reconstruction, as follows:

providing a first system of voxels for a region of interest;

obtaining radioactive-emission data from the region of interest;

performing a first reconstruction, based on the radioactive-emission data and the first system of voxels, to obtain a first image;

correcting the first system of voxels, by aligning voxel boundaries with object boundaries, based on the first image; thus obtaining a second system of voxels;

performing a second reconstruction, based on the radioactive-emission data and the second system of voxels, thus obtaining a second image.

Alternatively, a set of radioactive emission data is obtained, possibly with a second injection, in order to concentrate the viewing on the anatomic voxels, as follows:

providing a first system of voxels for a region of interest;

obtaining a first set of radioactive-emission data from the region of interest;

performing a first reconstruction, based on the first set of the radioactive-emission data and the first system of voxels, to obtain a first image;

correcting the first system of voxels, by aligning voxel boundaries with object boundaries, based on the first image; thus obtaining a second system of voxels, which is anatomically based;

obtaining a second set of radioactive-emission data from the region of interest, based on the second system of voxels, which is anatomically based; and performing a second reconstruction, based on the second set of the radioactive-emission data and the second system of voxels, thus obtaining a second image.

Anatomic Modeling

Bull's Eye, or polar map, is a semi-automatic method for the quantification and evaluation of coronary artery disease from SPECT tomograms obtained by marking the myocardium with Tl-201 or MIBI-Tc-99. The polar map is computed from cross-sectional slices of the Left Ventricle (LV). For each slice, the center and a radius of search that contains the LV are determined and the LV is divided into radial sectors. The maximum count value of each sector is computed, generating a profile. Profiles are plotted as concentric circle onto the map. The resulting map is a compression of 3D information (LV perfusion) onto a single 2D image.

Yet the bull's eye or polar map is reconstructed from a rigorous geometry of voxels, for example, of 5×5×5 mm, or 4×4×4 mm, which cuts across tissue types, thus providing smeared information.

A voxel division that is based on an anatomical structure would be highly preferred, as it would allow the measurements of processes within and across anatomical features, substantially without the smearing effect. For example, if specific voxels are used to define blood regions, and others are used to define muscle regions, than diffusion across boundary membranes and other processes may be evaluated, substantially without a smearing effect.

Anatomical model is based on voxels that follow anatomical structures, and may be shaped for example, as a sphere, a tube, or as a shell segment, rather than as a the standard cube.

When combined with a camera of high resolution and sensitivity and with gated measurements, anatomic modeling would be clearly advantageous over standard, rigorous modeling, especially for kinetic studies are meaningful only with respect to specific tissue types.

In accordance with embodiments of the present invention, the polar map may be produced with a reduced number of amplitudes, or levels, for example, 7 levels of severity, or 5 levels of severity, from healthy to severe.

Kinetic Modeling

As part of the imaging and analysis processes, the camera may be able to produce a time series of 2D or 3D images, showing reconstructed intensity in overall volume and its changes over time.

Likewise, it may be desirable not to reconstruct the entire volumetric region but only limited segments of interest. In those segments, resolution of segment definition may be very important in order to minimize partial volumetric region effect, which results in a biased estimate of the kinetic process.

In an exemplary embodiment, the analysis of the kinetic process may be after reconstruction of the intensity in the entire volumetric region or in the selected segments has been done for a series of time points. In that case, each segment or location in overall volume (u) has a list of intensity (I) values in time (t), and the list I(u,t) may be further analyzed to fit parametric kinetic model.

Such a parametric kinetic model may be a variety of kinds, depending on the modeling on the biological process. Examples of such models may be found in PCT/IL2005/001173.

In a simplistic example, the model may be $$I(u,t)=B(t) \cdot (1-e^{-k_1(u) \cdot t}) \cdot e^{-k_2(u) \cdot t}$$

where B(t) is a concentration in the blood, whether obtained from imaging a segment which is pure blood (e.g. major blood vessel, or volumetric region within the heart chamber), or may be known from other sources (by injection profile, other invasive or non invasive measurements from the blood, etc). $k_1(u)$ is the time constant representing a process of uptake into the tissue at segment u, and $k_2(u)$ is the time constant representing a process of washout from the tissue at segment u.

There may be many other models, and for example the equation above may take other forms such as $$I(u,t)=B(t)*F_1(k_1(u),\tau)*F_2(k_2(u),\tau)$$

where * stands for either multiply operation or convolution in most cases, and $F_1$ and $F_2$ represent processes. In an example, the effect of such process on the intensity may be modeled in linear cases by convolution of the intensity in the blood with an impulse response of a linear process $F_1$ ($k_i(u)$, τ). Each of these may include one or more time constants $k_i(u)$, and the time profile is described as a function of time τ. There may be one or more such processes $F_i$, for example 1 (e.g. uptake or decay only), 2 (e.g. simultaneous uptake and clearance processes), 3 (e.g. combination with accumulation or metabolism), 4 or more.

A process of fitting may be used between the reconstructed intensity in overall volume and time and the parametric models mentioned above.

In another example, the parametric model may be incorporated into the reconstruction process. In this case, it is not necessary to perform reconstruction of intensities I(u,t) in overall volume and time and then use that information to extract time constants of biological processes $k_i(u)$.

Instead, the imaging equation $$y_n(t) \sim \text{Poisson}\left(\left[\sum_u \varphi_n(u) I(u,t)\right]\right)$$

may be explicitly replaced with the model of the intensities $$y_n(t) \sim \text{Poisson}\left(\left[\sum_u \varphi_n(u) B(t) * F_1(k_1(u), \tau) * F_2(k_2(u), \tau)\right]\right)$$

(where $y_n(t)$ is the number of photon measured from a viewing position n with a probability function of the view $\phi_n(u)$).

In this case, the reconstruction process (e.g. by Maximum-Likelihood, Expectation maximization, or other equation solving techniques) is used to recover the best fitting values of $k_i(u)$, instead of recovering I(u,t) and then $k_i(u)$.

In some embodiments of the present invention, the use of a camera directly intended to perform dynamic studies, the ability to avoid interim recovery of intensities in 3D-overall volume in various time periods may be a benefit, as the design of the scanning is optimized for the kinetic parameters reconstruction, and not necessarily to image quality in each time point.

Active Vision

The camera of the present invention may further include active vision which relates to a method of radioactive-emission measurements of a body structure, comprising:

performing radioactive-emission measurements of the body structure, at a predetermined set of views;

analyzing the radioactive-emission measurements; and dynamically defining further views for measurements, based on the analyzing.

Active vision may be used, for example, to better define an edge, by changing a view direction, to direct a saturating detecting unit away from a hot spot, to change the duration at a certain location, when a greater number of counts are required, or when sufficient counts have been obtained.

Reconstruction Stabilizer

The method of reconstruction employed by the present invention may further include a method for stabilizing the reconstruction of an imaged volumetric region, comprising:

performing an analysis of the reliability of reconstruction of a radioactive-emission density distribution of said volumetric region from radiation detected over a specified set of views; and defining modifications to at least one of a reconstruction process and a data collection process to improve said reliability of reconstruction, in accordance with said analysis.

Additionally, the method may include calculating a measure of said reliability of reconstruction, said measure of reliability of reconstruction being for determining a necessity of performing said modifications.

Furthermore, the method may include:

providing a detection probability matrix defining a respective detection probability distribution of said volumetric region for each of said views; calculating the singular values of said detection probability matrix;

identifying singular values as destabilizing singular values.

Additionally, the method may include calculating a condition number of said probability matrix as a measure of said reliability of reconstruction.

It will be appreciated that this approach may result in non-uniform voxels, wherein voxel volumetric region may increase or decrease as necessary to increase the reliability of the reconstruction View Selection The present invention further utilizes a method of optimal view selection, as follows:

providing said volumetric region to be imaged;
modeling said volumetric region;
providing a collection of views of said model;
providing a scoring function, by which any set of at least one view from said collection is scorable with a score that rates information obtained from said volumetric region by said set;
forming sets of views and scoring them, by said scoring function; and
selecting a set of views from said collection, based on said scoring function for imaging said volumetric region.

Additionally, zooming in onto a suspected pathology may be performed by a two-step view selection, wherein once the suspected pathology is observed, that region of the volumetric region is modeled anew and a new collection of views is obtained specifically for the suspected pathology.

Experimental Results

Reference is now made to FIGS. 9A-9J, which schematically illustrate cardiac imaging of Tc-99m-Teboroxime, with the dynamic camera 10 in accordance with aspects of the present invention. The significance of the experimental data provided herein is the ability to successfully image Teboroxime, which as FIG. 5B illustrates is washed out of the body very quickly.

Figure 9A:
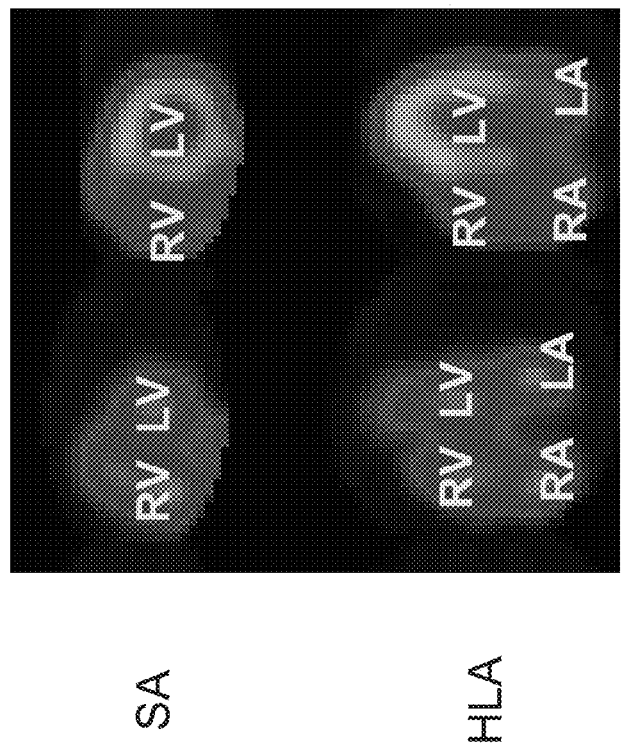

FIG. 9A provides anatomical landmarks, as follows:
Left Ventricle (LV)
Right Ventricle (RV)
Left Atrium (LA)
Right Atrium (RA)

Figure 9B:
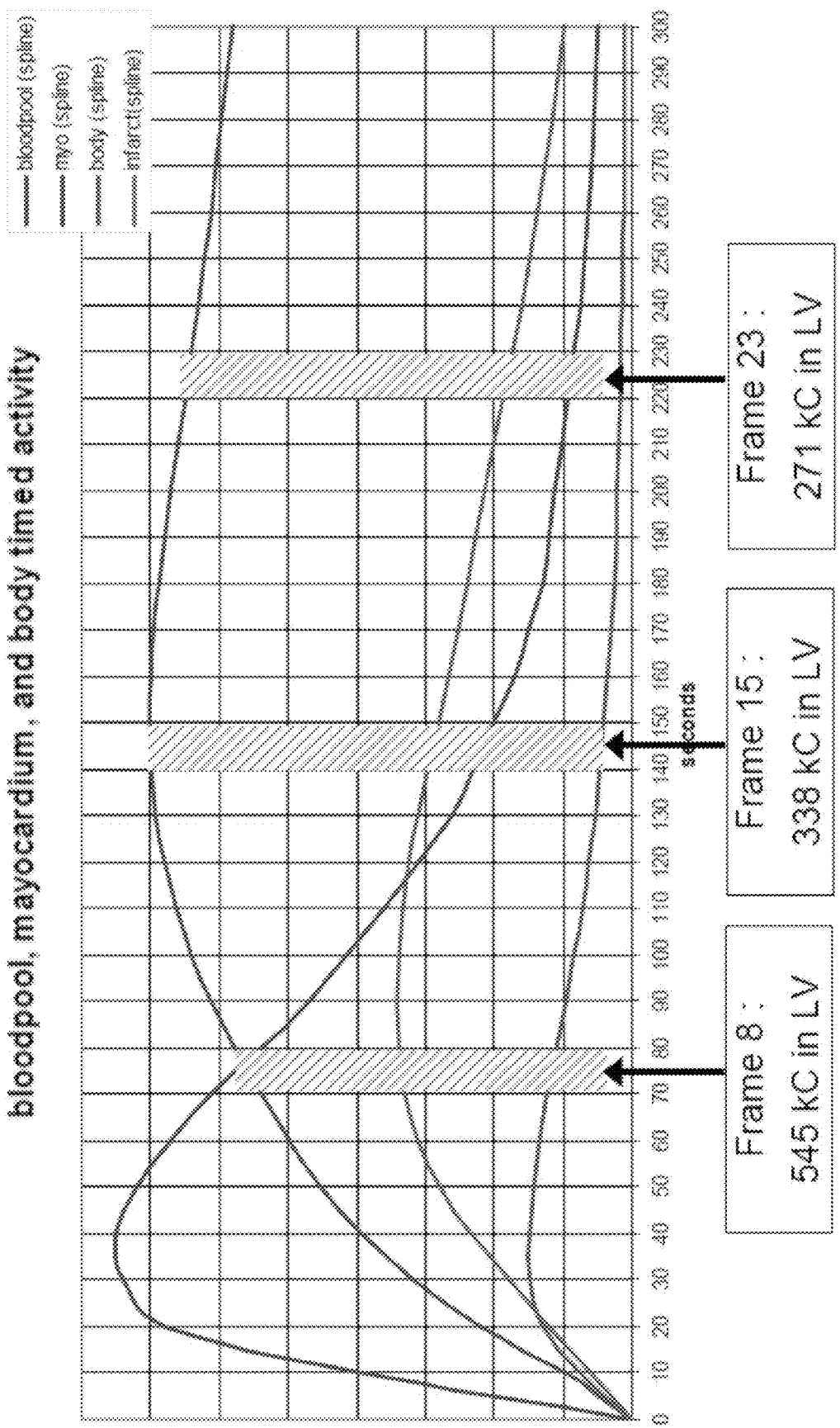

FIG. 9B is a dynamic study input of bloodpool, mayocardium, and body timed activity.

Figure 9C:
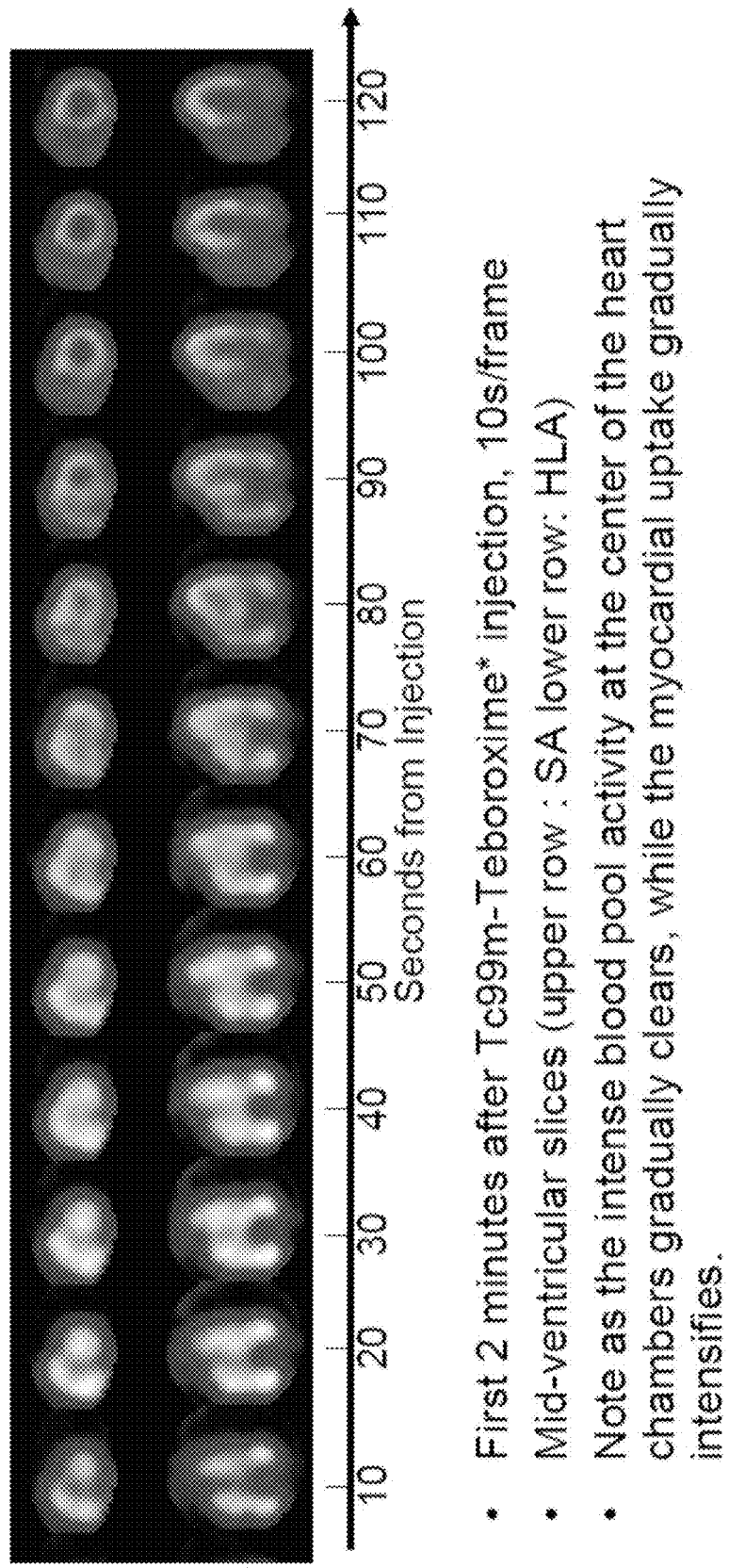

FIG. 9C is a Film-stripe representation of a dynamic SPECT study, as follows:
First 2 minutes after Tc99m-Teboroxime* injection, 10 s/frame
Mid-ventricular slices (upper row: SA lower row: HLA)
Note: as the intense blood pool activity at the center of the heart chambers gradually clears, while the myocardial uptake gradually intensifies.

Figure 9D:
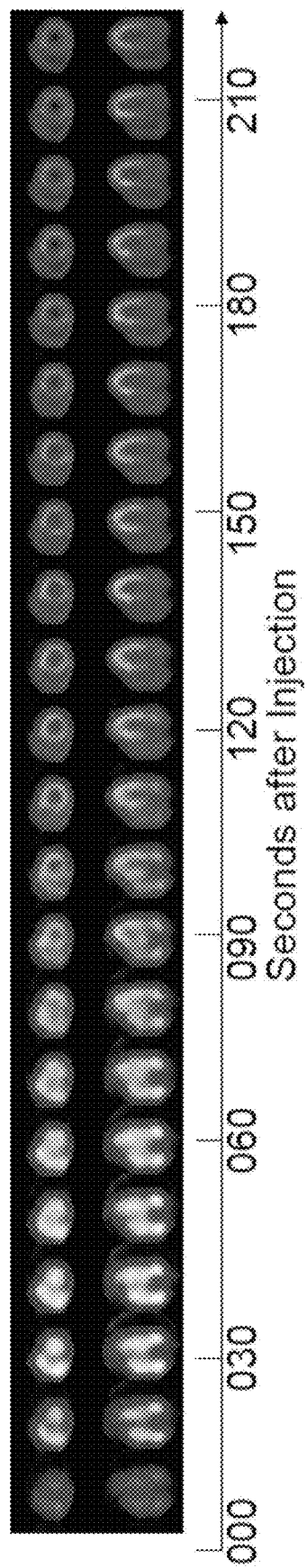
Figure 9E:
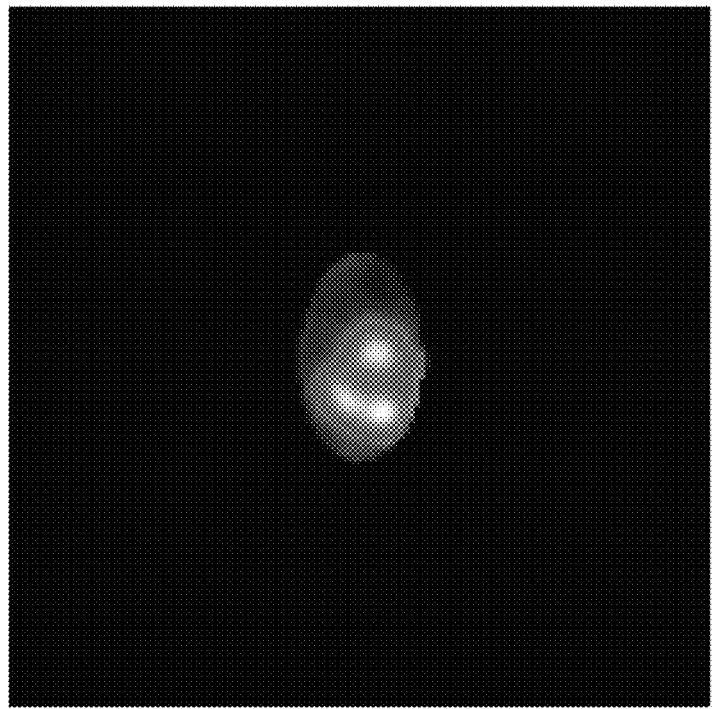

FIG. 9D is a Film-stripe representation of a dynamic SPECT study, as follows:
First 4 minutes after Tc99m-Teboroxime* injection, 10 s/frame
Mid-ventricular slices (upper row: SA lower row: HLA)
Note: as the intense blood pool activity at the center of the heart chambers gradually clears, while the myocardial uptake gradually intensifies FIG. 9E is a Movie representation of a dynamic SPECT study (SA), as follows:
First 4 minutes after Tc99m-Teboroxime* injection, 10 s/frame
Mid-ventricular SA slices.
Note: as the intense blood pool activity gradually clears in LV and RV cavities
Note: Myocardial uptake gradually intensifies, (the thin walled RV is less intense)

Figure 9F:
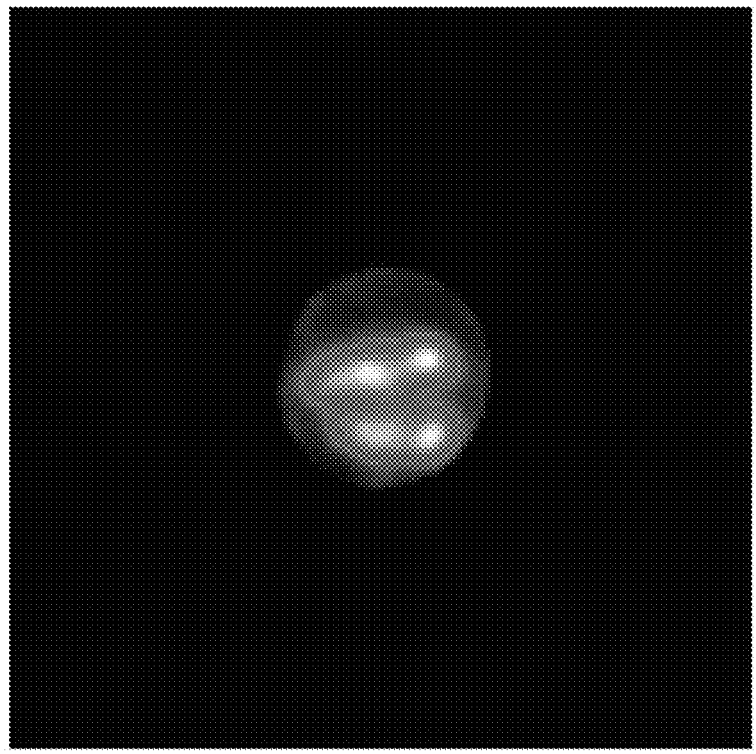

FIG. 9F is a Movie representation of a dynamic SPECT study (SA), as follows:
First 4 minutes after Tc99m-Teboroxime* injection, 10 s/frame
Mid-ventricular SA slices.
Note: as the intense blood pool activity gradually clears in LV, RV, LA and RA cavities
Note: Myocardial uptake gradually intensifies, (the thin walled RV ant atria are less intense)

Figure 9G:
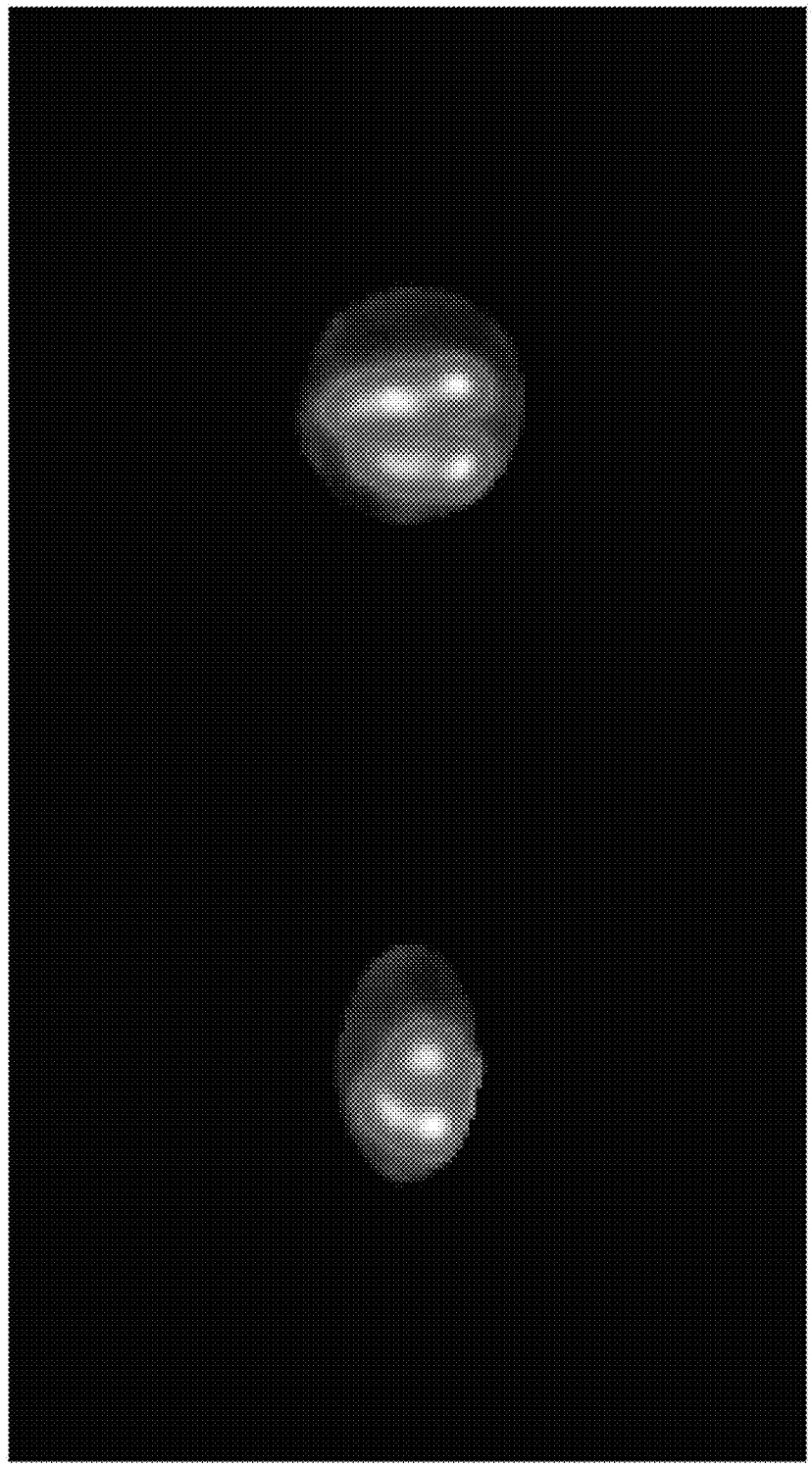

FIG. 9G is a Movie representation of a dynamic SPECT study (fast).

Figure 9H:
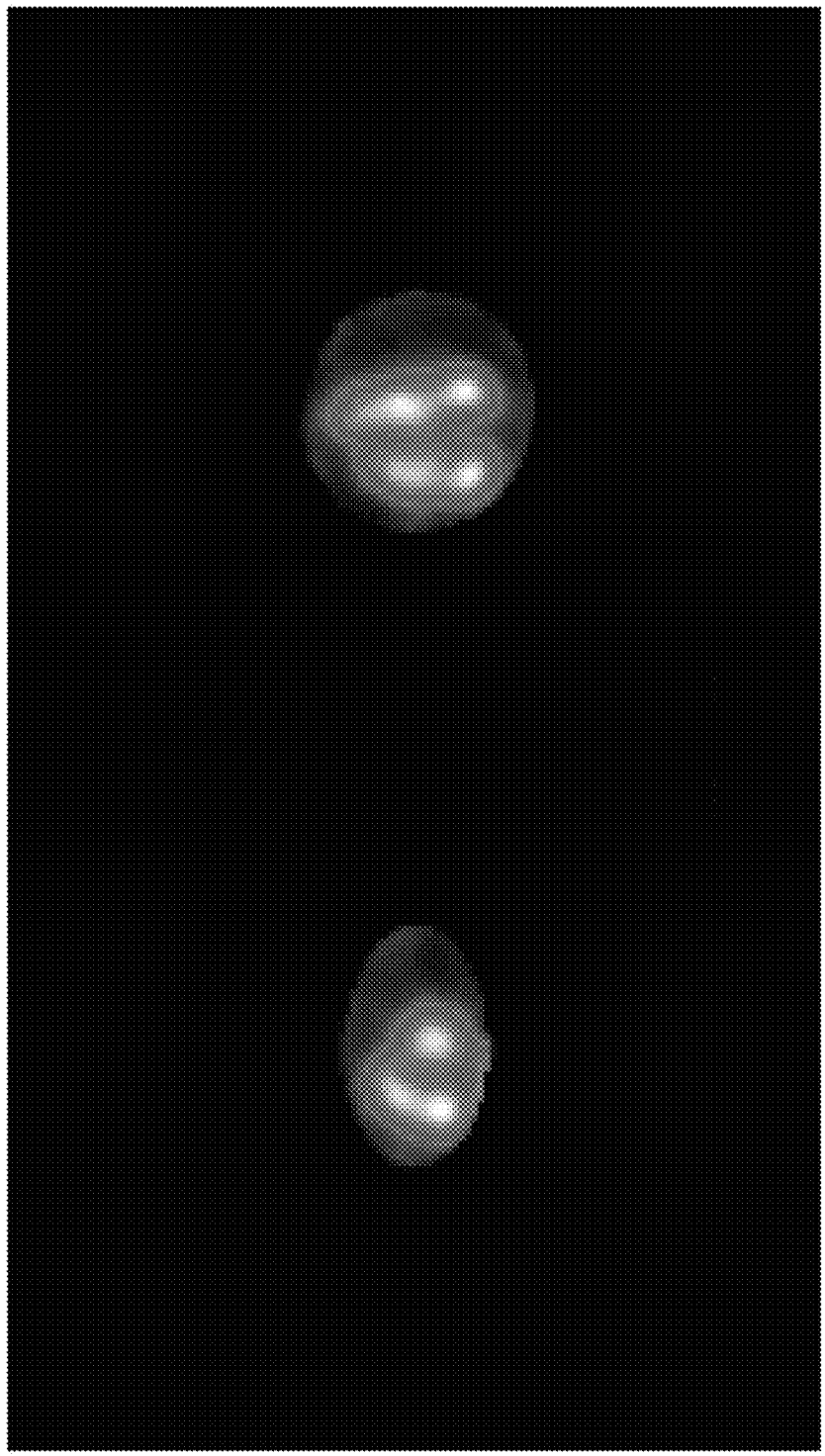

FIG. 9H is a Movie representation of a dynamic SPECT study (slow).

Figure 9I:
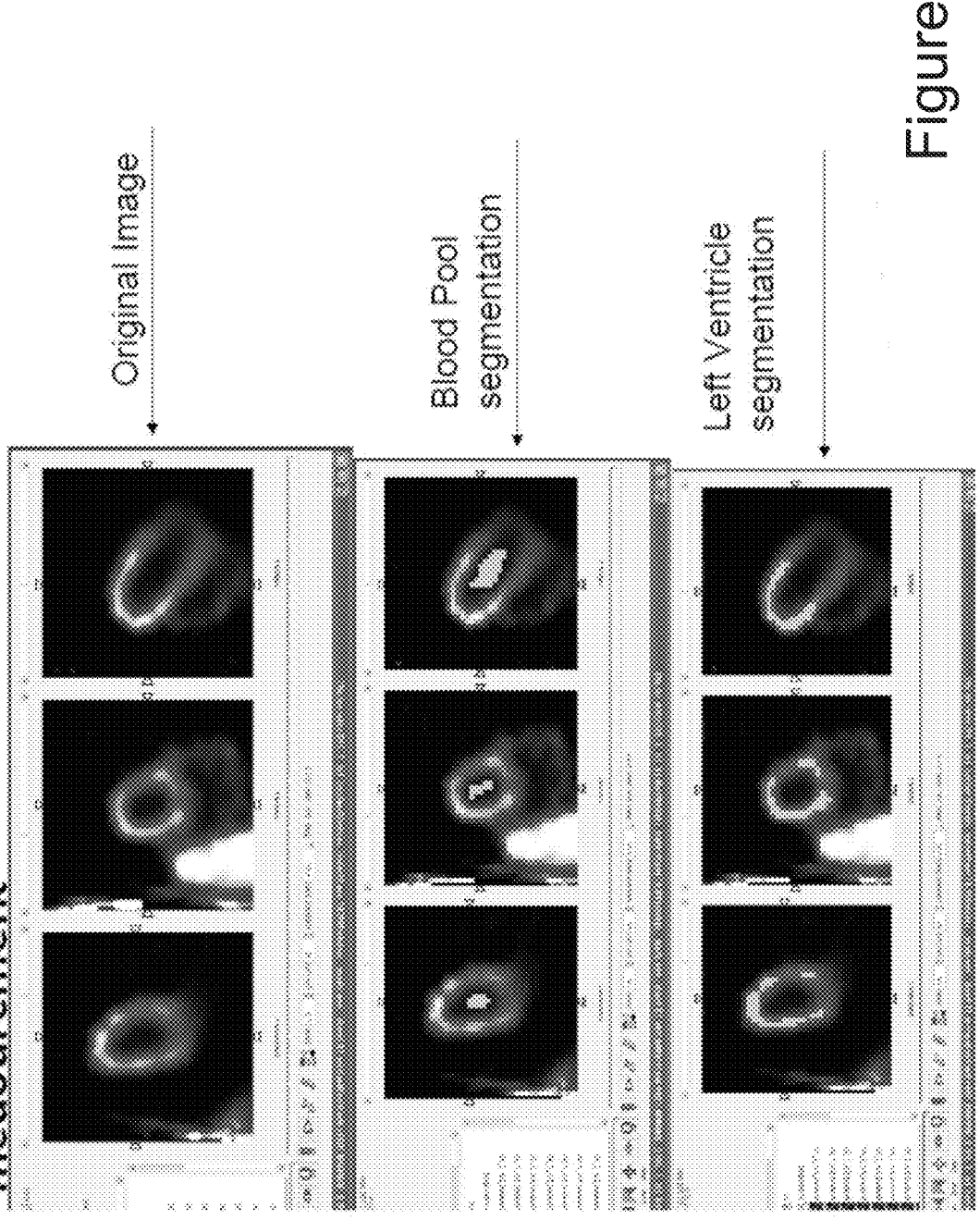
Figure 9J:
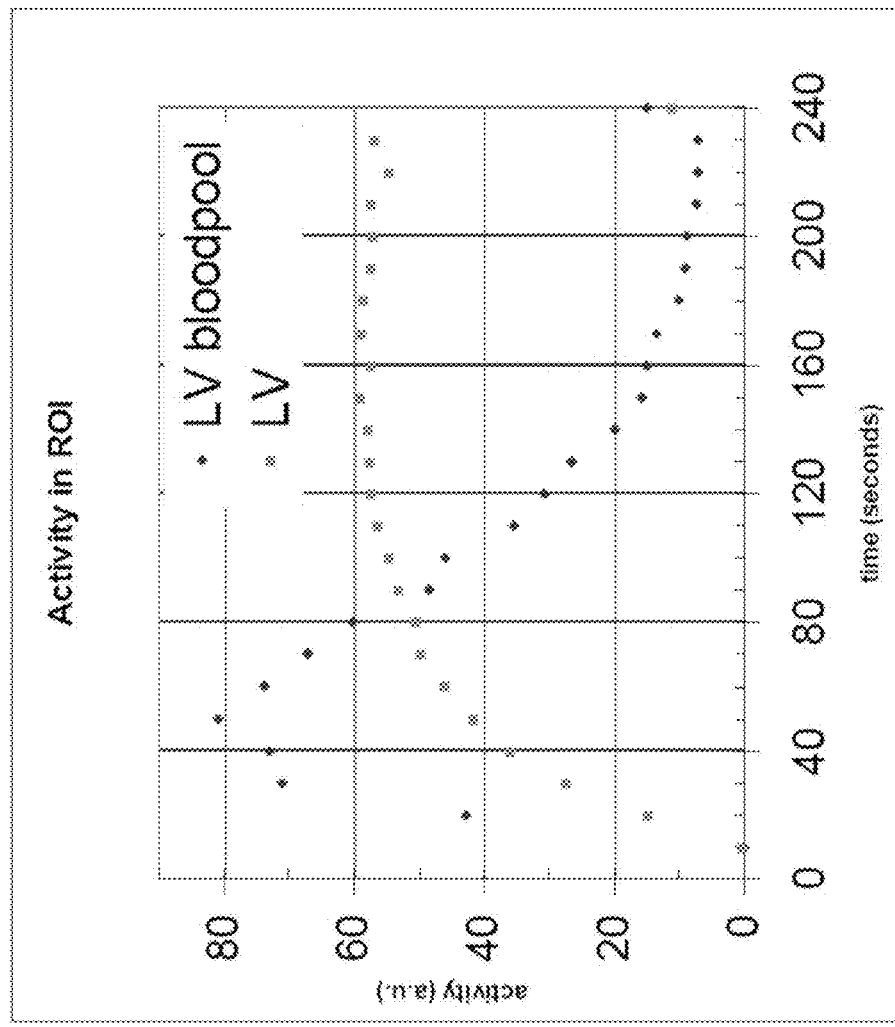

FIG. 9I represents volumetric region segmentation for separate tissue flow dynamics measurement FIG. 9J represents measured kinetic curves.

FIG. 10 is another experiment, illustrating time binning at a rate of 0.001 seconds.

Electronic Scheme for Fast Throughput

High-sensitivity detecting units, such as the room temperature, solid-state CdZnTe (CZT) detectors utilized in the present embodiments, must be discharged frequently, as their high-sensitivity can lead to rapid saturation. When a given detector saturates, the output count for the associated pixel no longer accurately reflects the number of incoming photons, but rather the maximum number that the detector is capable of absorbing. This inaccuracy may lead to errors during reconstruction. It is therefore important to perform readout often enough to avoid detector saturation.

The data channel from the assembly 20 (or the assembly 20 readout circuitry) to the signal processing components must be fast enough to handle the large quantities of data which are obtained from the detecting units 12.

The electronic scheme of the present embodiments preferably includes one or more of the following solutions for performing frequent detector unit readout, while maintaining high data throughput to prevent data channel saturation.

In a preferred embodiment, the dynamic SPECT camera 10 includes a parallel readout unit for performing parallel readout of emission count data. Parallel readout requires less time than serial readout (in which the pixels are read out in sequence), as multiple pixels may be read out in a single cycle without losing the information of the individual pixel counts. The readout rate can thus be increased without loss of data.

Parallel readout may be performed at many levels. Reference is now made to FIG. 11, which illustrates various levels of detector unit organization at which parallel readout may be performed. The present exemplary embodiment shows a single detector array 25, which includes three assemblies 20. Each assembly includes a plurality of blocks 18 of detector units 12. Each detecting unit 12 includes a single-pixel detector (FIG. 1D).

The parallel readout unit preferably performs parallel readout at the level of one or more of:
a) detecting units 12, each of the single-pixel detector 14;
b) blocks 18, which include a plurality of detecting units 12;
c) assemblies 20, which include a plurality of blocks 18
d) array 25, which includes a plurality of assemblies 20.

When the parallel readout unit performs parallel readout at the level of the detecting units 12, count values are read out in parallel from each of the electrically insulated single-pixel detector 14. The single-pixel detector 14 is discharged at readout, and the photon collection process begins anew.

When the parallel readout unit performs parallel readout at the level of the block 18, count values from each of the detecting units 12 are read out serially, however multiple blocks 18 are read out in parallel. This approach is less complex to implement than parallel readout of the detecting units 12, although it results in a certain reduction in readout rate to accommodate the serial readout. Again, the single-pixel detectors 14 are discharged at readout.

Similarly, when the parallel readout unit performs parallel readout at the level of the assembly 20, count values from each of the detecting units 12 in the assembly 20 are read out serially, however multiple assemblies 20 are read out in parallel.

Parallel readout preferably includes multiple detection, amplification and signal processing paths for each of the pixels, thereby avoiding saturation due to a single localized high emission area—"hot spot". This is in contrast with the Anger camera, in which multiple collimators are associated with a single-pixel scintillation detector, and saturation of the scintillation detector may occur even due to a localized hot spot.

FIG. 12 illustrates an exemplary embodiment of parallel readout in the dynamic SPECT camera 10. Radioactive emissions are detected by pixelated CZT crystals, where each crystal is divided into 256 pixels. The crystal is part of a 'CZT MODULE' (B) which also includes two ASICS each receiving events from 128 pixels. The ASIC is an OMS 'XAIM3.4' made by Orbotech Medical Systems, Rehovot, Israel, together with the CZT crystal. The 2 ASICs share a common output and transmit the data to 'ADC PCB' (C) that handles four 'CZT MODULES' (B) in parallel. Thus, a total of 1024 pixels are presently channeled through one ADC board. The system is capable of further increasing the accepted event rate by channeling every two ASICS through a single ADC. The 'ADC PCB' (C) transmits the data to the 'NRG PCB' (D) that handles ten 'ADC PCB's (C) in parallel, but could be further replicated should one want to further decrease "dead time". The 'NRG PCB' (D) transmits the data to the 'PC' (E) where it is stored.

All in all, in the present embodiment, forty CZT MODULEs which contain a total of 10240 pixels transmit in parallel to the PC.

The bottle neck, and hence the only constraint, of the system data flow is the ASICS in the 'CZT MODULE' (B) and the connection to the 'ADC PCB's (C):
1. An ASIC (128 pixels) can process one photon hit within 3.5 uSec, or 285,000 events/sec over 128 pixels, i.e. over 2200 events/px/sec-an exceedingly high rate.
2. Two ASICS share the same output, and hence coincident event output of the two ASICS in a 'CZT MODULE' (B) will cause a collision and information loss. The duration of an event output from the ASIC is 1 uSec.

When the readout is rapid, the rate at which the radiation emission data is read out of the single-pixel detectors 14 may be greater than the rate at which it may be output to the processor. One known solution for managing a difference data arrival and data processing rates is to use a buffer. The buffer provides temporary storage of the incoming data, which is retrieved at a later time.

A buffered readout configuration can result in the loss of timing information, unless active steps are taken to preserve the time information associated with the collected emission data, for example, as taught hereinabove, under the heading, "The Timing Mechanism 30."

In accordance with embodiments of the present invention, timing information is preserved. The electrical scheme may include a buffer which stores emission data along with timing information for each data item or group of data items (in the case where emission data from several detectors was obtained at substantially the same time, for example due to parallel readout), and an identification of the associated detector unit. Utilizing a buffer ensures that emission data may be collected from the detectors frequently enough to avoid saturation, even when the data channel throughput is limited. In stop and shoot mode, for example, the emission count data may be stored in the buffer for retrieval while the detector head is moving to the next location. Accurate reconstruction may thus be performed.

The camera readout circuitry is preferably designed to provide fast readout and detecting unit discharge. Fast readout circuitry may include fast analog and digital circuitry, fast A/D converters, pipelined readout, and so forth. After the emission data has been read out of the single-pixel detectors 14, it may be necessary to convey the data to a processor for reconstruction as a single or limited number of data streams. The camera electronic scheme may include a multiplexer, for combining two or more emission data streams into a single data stream. The emission data may thus be conveyed to the processor over one physical link (or alternately over a reduced number of parallel links). For each radioactive emission event, the multiplexer includes both the timing information and an identification of the single-pixel detector 14 supplying the event. The multiplexed data may later be de-multiplexed by the processor, and reconstruction may be performed with complete information for each data item, including for example, total counts per single-pixel detector 14, per time bin, single-pixel detector location and orientation, and the time bin. Parallel readout may thus be performed, even when the collected data is to be output over a single data link.

Sensitivity Consideration.

It will be appreciated that dynamic imaging with a SPECT camera has been attempted in the past, unsuccessfully, primarily, because prior-art SPECT cameras are not sensitive enough to provide tomographic reconstruction images, for example, of a heart, with sufficient object resolution, for example, 10×10×10 cubic millimeters, in less than a minute.

As a case in point, U.S. Pat. No. 7,026,623, to Oaknin, et al., filed on Jan. 7, 2004, issued on Apr. 11, 2006, and entitled, "Efficient single photon emission imaging," describes a method of diagnostic imaging in a shortened acquisition time for obtaining a reconstructed diagnostic image of a portion of a body of a human patient who was administered with dosage of radiopharmaceutical substance radiating gamma rays, using an Anger Camera and SPECT imaging. The method includes effective acquisition times from less than 14 minutes to less than 8 minutes. Oaknin, et al., do not claim an effective acquisition time of less than 7 minutes. Yet, in view of the section entitled, "Time Scale Considerations," hereinabove, a sampling rate of 8 about minutes is far too slow for myocardial perfusion studies, where a sampling rate of at least two tomographic reconstruction images per heartbeat, that is, about every 30 seconds, is desired, and furthermore, where processes occur at rates of several seconds, and must be sampled at rates of a second or less, as seen in FIG. 5B.

The dynamic SPECT camera 10 in accordance with embodiments of the present invention achieves sensitivity sufficient for the required sampling rates of between every 30 seconds and every half a second, by combining several features, specifically intended to increase sensitivity, as follows:

a collimator 16 with a solid collection angle δ of at least 0.005 steradians or greater, for a fast collection rate, and high sensitivity, wherein the loss in resolution is compensated by one or a combination of the following factors:

i. motion in a stop and shoot acquisition mode, at very small incremental steps, of between about 0.01 degrees and about 0.75 degrees.

ii. simultaneous acquisition by the assemblies 20, each scanning the same region of interest from a different viewing position, thus achieving both shorter acquisition time and better edge definitions.

iii. the structure 15 conforming to the body contours, for acquisition with substantial contact or near contact with the body.

Definition of a Clinically-Valuable Image

In consequence, the dynamic SPECT camera 10 is capable of producing a "clinically-valuable image" of an intra-body region of interest (ROI) containing a radiopharmaceutical, while fulfilling one or more of the following criteria:

1. the dynamic SPECT camera 10 is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the camera is capable of acquiring at least one of 2000 photons emitted from the ROI during the image acquisition procedure;

2. the dynamic SPECT camera 10 is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment, the camera is capable of acquiring at least 1,000,000 photons emitted from a volume of the ROI having a volume of no more than 200 cc;

3. the dynamic SPECT camera 10 is capable of acquiring an image of a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to $10^5$ photons/second/cc, such that the range I is $10^5$ photons/second/cc, and at least 50% of the voxels of the reconstructed three-dimensional intensity image of the ROI have inaccuracies of less than 15% of range I, i.e., less than $1.5 \times 10^4$ photons/second/cc. For some applications, the study produce a parametric image related to a physiological process occurring in each voxel. In one particular embodiment, the image has a resolution of at least 5×5×5 mm, and at least 50% of the voxels have inaccuracies of less than 15% of range I;

4. the dynamic SPECT camera 10 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to $10^5$ photons/second/cc, such that the range I is $10^5$ photons/second/cc, and at least 50% of the voxels of the reconstructed three-dimensional intensity image of the ROI have inaccuracies of less than 15% of range I, i.e., less than $1.5 \times 10^4$ photons/second/cc. For some applications, the study produces a parametric image related to a physiological process occurring in each voxel. In one particular embodiment, the image has a resolution of at least 5×5×5 mm, and at least 50% of the voxels have inaccuracies of less than 15% of range I;

5. the dynamic SPECT camera 10 is capable of acquiring an image, which has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values I, and wherein at least 50% of the voxels of the reconstructed parametric three-dimensional image have inaccuracies less than 100% of range I, such as less than 70%, 50%, 40%, 30%, 25%, 20%, 15%, 10%, 5%, 2%, 1%, or 0.5% of range I. For example, the physiological process may include blood flow, the values of the parameters of the physiological process may have a range from 0 to 100 cc/minute, such that the range I is 100 cc/minute, and at least 50% of the voxels of the reconstructed parametric three-dimensional image have inaccuracies less than 25% of range I, i.e., less than 25 cc/minute. In one particular embodiment, the image has a resolution of at least 5×5×5 mm, and at least 50% of the voxels have inaccuracies of less than 25% of range I; and/or 6. the dynamic SPECT camera 10 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein if the radiopharmaceutical is distributed substantially uniformly within a portion of the ROI with an emission-intensity I+/−10% (which is defined as emitted photons/unit time/volume), and wherein at least 85% of the voxels of the reconstructed three-dimensional emission-intensity image of the portion of the ROI have inaccuracies of less than 30% of intensity I, such as less than 15%, 10%, 5%, 2%, 1%, 0.5%, 20%, or 25% of intensity I. For example, the radiopharmaceutical may be distributed within a volumetric region with a uniform emission-intensity I of 10^5 photons/second/cc, and at least 85% of the voxels of the reconstructed three-dimensional intensity image of the volumetric region have inaccuracies of less than 15% of intensity I, i.e., less than $1.5 \times 10^4$ photons/second/cc. For some applications, the same definition may apply to a study which produces a parametric image related to a physiological process occurring in each voxel. In one particular embodiment, the image has a resolution of at least 5×5×5 mm, and at least 50% of the voxels have inaccuracies of less than 15% of intensity I.

It is expected that during the life of this patent many relevant dynamic SPECT cameras will be developed and the scope of the term dynamic SPECT camera is intended to include all such new technologies a priori.

As used herein the term "substantially" refers to ±10%.

As used herein the term "about" refers to ±30%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It is expected that during the life of this patent many relevant devices and systems will be developed and the scope of the terms herein, particularly of the terms SPECT detectors, processing unit, communication, and images are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for reconstructing a radioactive emission image of an overall volume in a human body having first and second volumetric regions, each volumetric region having respectively independent dynamic characteristics, the method comprising:
   a) obtaining a structural image of the overall volume in the human body, including said volumetric regions;
   b) delineating said structural image of the overall volume including said first and second volumetric regions, to delineate said first and second volumetric regions-;
   c) obtaining radioactive emissions from the overall volume in the human body, including said volumetric regions and including timing data, using a plurality of detectors each performing oscillatory motion;
   d) reconstructing, using said radioactive emissions, a series of 3D images with time by:
   separately reconstructing said first volumetric region and said second volumetric region
   using said timing data, where different gating is employed for said first and said second volumetric regions, said different gating according to said respectively independent dynamic characteristics; and
   using a model for at least one of said volumetric regions, said model describing a relationship, with time, for said at least one volumetric region, between radioactive emission intensities and one or more of: concentration of radioactive tracer in the blood, uptake time constant of the tissue and washout time constant of the tissue.

2. The method of claim, 1 wherein said separately reconstructing is an iterative process including using object implantation for refining reconstruction of at least one of the first and second volumetric regions.

3. The method of claim 2, wherein at least one of the volumetric regions comprises at least a part of a body organ or other body portion; and
   wherein said object implantation includes:
      providing a model of only a part of said overall volume in the human body, said model comprising a general location and shape of, and expected number of photons emitted from, said body organ or said at least part of body portion;
      replacing, at a general location in said initial radioactive emission image corresponding to said model general location, initial radioactive emission image voxels with said model general shape and initial radioactive emission image voxel photon counts, based on said expected number of photons from said model, where said replacing is one or more times during said iterative process, each time for providing a better starting point for performing next iteration of said reconstruction of at least one of the first and second volumetric regions.

4. The method of claim 1, wherein said obtaining radioactive emissions further includes obtaining timing data by a method selected from the group consisting of time stamping, time binning, and a combination thereof.

5. The method of claim 4, wherein said separately reconstructing includes separately reconstructing said first and second volumetric regions according to said respectively independent dynamic characteristics of said timing data.

6. The method of claim 4,
   wherein said timing data comprises first timing data for said first volumetric region and second timing data for said second volumetric region;
   wherein said separately reconstructing comprises: reconstructing said first volumetric region using said first timing data; and reconstructing said second volumetric region using said second timing data.

7. The method of claim 6, including:
obtaining a second set of radioactive emissions from the overall volume in the human body, including said volumetric regions, after the reconstructing the initial radioactive emission image, the second set including timing data,
wherein said separately reconstructing includes separately reconstructing said first and second volumetric regions according to said respectively independent dynamic characteristics, from said second set.

8. The method of claim 7, wherein said first and second volumetric regions have higher dynamic activity than surrounding tissue;
wherein obtaining a second set of radioactive emissions, further includes independently directing detecting resources to said first and second volumetric regions, so as to concentrate detecting resources on the volumetric region of greater dynamic activity.

9. The method of claim 1, wherein separately reconstructing further includes independently carrying reconstruction of said first and second volumetric regions, to different levels of accuracy, so as to concentrate reconstruction resources on a volumetric region of greater dynamic activity.

10. The method of claim 1, wherein said first volumetric region confines a human heart.

11. The method of claim 1, wherein said volumetric regions comprises independent sub-volumetric regions, wherein during said separately reconstructing, each one of said independent sub-volumetric regions is reconstructed separately.

12. The method of claim 1, wherein said radioactive emissions are obtained using a single photon emission computed tomography (SPECT) camera.

13. The method of claim 12, wherein said SPECT camera comprises a plurality of detecting units.

14. The method of claim 13, wherein time binning is independently enabled to each detecting unit from said plurality of detecting units.

15. The method of claim 13, wherein time binning is independently enabled to one or more sub-groups of said plurality of detecting units from said plurality of detecting units.

16. The method of claim 13, wherein each said detecting unit includes:
a single-pixel detector, for detecting radioactive emissions; and
a dedicated collimator, attached to the single-pixel detector, at the proximal end thereof, for defining a solid collection angle δ for the detecting unit.

17. The method of claim 1, wherein said separately reconstructing comprises reconstructing an initial radioactive emission image which is represented by a system of voxels.

18. The method of claim 17, further comprising:
constructing an anatomical construction of voxels, for said system of voxels, in which voxel boundaries are aligned with boundaries of structural objects of said first volumetric region, based on said structural image, said separately reconstructing being based on said anatomical construction of voxels.

19. The method of claim 18, wherein the anatomical construction of voxels includes voxels of varying volumetric regions, depending on their anatomic position and relevance.

20. The method of claim 1, wherein said structural image is provided by a source, selected from the group consisting of 2-D ultrasound, 3-D ultrasound, planner x-rays, CT x-rays, MRI, and an anatomical atlas.

21. The method of claim 1, wherein said obtaining radioactive emissions comprises time binning said radioactive emissions using different time bin lengths for said first and said second volumetric regions.

22. The method of claim 1, wherein said obtaining a structural image of the overall volume includes obtaining the structural image of the overall volume, including the separate volumetric regions, wherein the first volumetric region has a first amount of dynamic activity and the second volumetric region has a second amount of dynamic activity, and wherein the first volumetric region moves in the overall volume relative to the second volumetric region.

23. The method of claim 1 comprising, after said separately reconstructing, repeating said separately reconstructing until a desired quality of reconstruction of the overall volume has been reached.

24. The method of claim 23, wherein it is determined that the desired quality of reconstructions of the overall volume has been reached when a number of gated voxels with activity is above a predefined threshold.

25. The method of claim 1, wherein said separately reconstructing includes separately reconstructing said first volumetric region and reconstructing said second volumetric region according to said respectively independent dynamic characteristics of said respective first and second volumetric regions;
wherein said method further includes combining said first and second reconstructed volumetric regions into a single image.

26. The method of claim 1, wherein said separately reconstructing comprises using at least two different said models for different portions of said at least one of said volumetric regions.

27. The method of claim 1, wherein said structural image is a first reconstruction based on said radioactive emissions of said overall volume.

28. The method of claim 1, wherein said model describes a relationship, between radioactive emission intensities and concentration of radioactive tracer in the blood, uptake time constant of the tissue, and washout time constant of the tissue.

29. The method of claim 1, wherein said using said model comprises generating, for said at least one volumetric region, a three dimensional relationship with time between said radioactive emission intensities and said one or more of: concentration of radioactive tracer in the blood, uptake time constant of the tissue and washout time constant of the tissue.

* * * * *